(12) United States Patent
Vocadlo et al.

(10) Patent No.: US 8,334,310 B2
(45) Date of Patent: Dec. 18, 2012

(54) SELECTIVE GLYCOSIDASE INHIBITORS AND USES THEREOF

(75) Inventors: David Vocadlo, Burnaby (CA); Ernest McEachern, Vancouver (CA); Keith Stubbs, Greenwood (AU); Tong-Shuang Li, Langley (CA); Garrett Whitworth, Surrey (CA); Julia Heinonen, Burnaby (CA); Matthew Macauley, Burnaby (CA)

(73) Assignee: Simon Fraser University, Burnaby, British Columbia (CA)

( * ) Notice: Subject to any disclaimer, the term of this patent is extended or adjusted under 35 U.S.C. 154(b) by 180 days.

(21) Appl. No.: 12/438,882

(22) PCT Filed: Aug. 31, 2007

(86) PCT No.: PCT/CA2007/001554
§ 371 (c)(1),
(2), (4) Date: Sep. 23, 2009

(87) PCT Pub. No.: WO2008/025170
PCT Pub. Date: Mar. 6, 2008

(65) Prior Publication Data
US 2010/0016386 A1     Jan. 21, 2010

Related U.S. Application Data

(60) Provisional application No. 60/841,196, filed on Aug. 31, 2006, provisional application No. 60/895,663, filed on Mar. 19, 2007.

(51) Int. Cl.
*A61K 31/429* (2006.01)
*C07D 513/04* (2006.01)

(52) U.S. Cl. .................................. 514/367; 548/153
(58) Field of Classification Search .................. 548/153; 514/367
See application file for complete search history.

(56) References Cited

U.S. PATENT DOCUMENTS

| | | | |
|---|---|---|---|
| 6,774,140 | B1 | 8/2004 | Wong et al. |
| 2004/0132142 | A1 | 7/2004 | Kobayashi et al. |
| 2004/0198772 | A1 | 10/2004 | Wong et al. |

FOREIGN PATENT DOCUMENTS

| | | |
|---|---|---|
| EP | 1371733 | 12/2003 |
| JP | 42003200 | 2/1967 |
| WO | WO 00/68194 | 11/2000 |
| WO | WO 02/072860 | 9/2002 |
| WO | WO 2004/103368 | 12/2004 |
| WO | WO 2004103386 | 12/2004 |
| WO | WO 2005/072268 | 8/2005 |
| WO | WO 2006/016904 | 2/2006 |
| WO | WO 2006/092049 | 9/2006 |

OTHER PUBLICATIONS

Document No. 127:66053, CAPLUS, retrieved on Sep. 2, 2010.*
WO 2006092049, Document No. 145:293295 retrieved from CAPLUS (2006).*
Knapp, et al. Document No. 127:66053, retrieved from CAPLUS. Entered in STN on Jun. 5, 1997.*
Noto, et al. Clin. Chem. 29/10, 1713-17-16 (1983).*
Alonso et al., "Promotion of Hyperphosphorylation by Frontotemporal Dementia Tau Mutations," J Biol Chem., 279:34873-3488 2004.
Arias et al., "Prolonged Incubation in PUGNAc Results in Increased Protein O-Linked Glycosylation and Insulin Resistance in Rat Skeletal Muscle," Diabetes 53:921-930 2004.
Arnold et al., "The Microtubule-Associated Protein Tau is Extensively Modified with O-linked N-acetylglucosamine," J. Biol. Chem. 271:28741-28744 1996.
Avalos et al., "Condensation of 2-Amin0-2-Deoxysugars with Isothiocyantes Synthesis of cis-1,2-Fused Glycopyrano Heterocycles," Tetrahedron 50:3273-3296 1994.
Avalos et al., "Sintesis de Hidrobromros de Glucopirano [2,1-d]-2-Tiazo-Linas," Anales de Quimica, Serie C: Quimica Organica y Bioquimica, 84:3-9 1988.
Avalos et al., "Synthesis of 1,3,4,6-Tetra-O-Acetyl-2-[Alkyl(aryl)-Thioureido]-2-Deoxy-α-D-Glucopyranoses and their Transformation into 2-Alkyl(aryl)amino-(1,2-Dideoxy-α-D-Glucopyrano)[2,1-*d* ]-2-Thiazolines," Carbohydrate Res. 154:49-62 1986.
Bedi et al., "A Convenient Synthesis of P-Nitrophenyl 2-deoxy-2-(thioacetamido)-beta-D-Glucopyranoside, -Galactopyranoside, and their 1-thio Analogs as Inhibitors of 2-acetamido-2-deoxy-beta-D-glucosidase," Carbohydrate Research, 62:253-259 1978.
Bennett and Pegg, "Alkylation of DNA in rat tissues following administration of streptozotocin," Cancer Res. 41:2786-2790 1981.
Bergmann et al., "Anchimeric Assistance in Hexosaminidases," Ber. Dtsch. Chem. Ges, 64B, 975-980 1999. *Article in German with English translation.
Bertram et al., "Evidence for Genetic Linkage of Alzheimer's disease to Chromosome 10q," *Science* 290:2302-2303 2000.
Boullanger et al., "The Use of N-alkoxycarbonyl Derivatives of 2-amino-2-deoxy-D-glucose as Donors in Gycosylation Reactions" Carbohydr Res., 202:151-164 1990.
Bounelis et al., "Glucosamine Provides Protection from Ischemial Reperfusion Injury and Calcium Overload In Isolated Hearts and Leads to an Increase in O-Linked Glycosylation," Shock, 21 170 Suppl. 2, 58 (67) 2004. Bovin et al., "Synthesis and Study of Thiazoline Derivatives of D-glucose," Izvestiya Akademii Nauk SSSR, Seriya Khimicheskaya, 2: 441-443, 1981.
Braidman et al., "Separation and Properties of Human Brain Hexosaminidase C," *Biochem J.*, 143:295-301 1974.
Bramblett et al., "Abnormal Tau Phosphorylation at Ser396 in Alzheimer's Disease Recapitulates Development and Contributes to Reduced Microtubule Binding," Neuron 10:1089-1099 1993.
Brickley et al., "GRIF-1 and OIP106, Members of a Novel Gene Family of Coiled-Coil Domain Proteins: Association In Vivo and In Vitro with Kinesin," J. Biol. Chem. 280:14723-14732 2005.
Burkart et al., "Mice lacking the poly(ADP-ribose) polymerase gene are resistant to pancreatic beta-cell destruction and diabetes development induced by streptozocin," Nat Med., 5:314-319 1999.
Hansch and Leo, "Substituent Constants for Correlation Analysis in Chemistry and Biology," Wiley, New York, 1979.

(Continued)

Primary Examiner — Shawquia Young
(74) Attorney, Agent, or Firm — Clark & Elbing LLP

(57) ABSTRACT

The invention provides compounds of formula (I) for selectively inhibiting glycosidases, prodrugs of the compounds, and pharmaceutical compositions including the compounds or prodrugs of the compounds The invention also provides methods of treating diseases and disorders related to deficiency or overexpression of O-GlcNAcase, accumulation or deficiency of O-GlcNAc

4 Claims, 7 Drawing Sheets

OTHER PUBLICATIONS

Champattanachai et al., "Glucosamine protects Neonatal Cardiomyocytes *from* Ischemia-reperfusion Injury Via Increased Protein-associated O-GlcNAc," Am J Physiol Cell Physiol. 292:C178-187 2007.

Cheng et al., "Alternative O-glycosylation/O-phosphorylation of Serine-16 in Murine Estrogen Receptor Beta: Post-translational Regulation of Turnover and Transactivation Activity," J Biol Chem., 276:10570-10575 2001.

Cheng et al., "Alternative O-glycosylation/O-phosphorylation of the Murine Estrogen Receptor beta," Biochemistry, 39:11609-11620 2000.

Chou et al., "c-Myc is Glycosylated at Threonine 58, a Known Phosphorylation Site and a Mutational Hot Spot in Lymphomas," J Biol Chem., 270:18961-18965 1995.

Chou et al., "O-linked N-acetylglucosamine and Cancer: Messages from the Glycosylation of c-Myc," Adv Exp Med Biol., 491:413-418 2001.

Cole et al., "Glycosylation Sites Flank Phosphorylation Sites on Synapsin I: O-linked N-acetylglucosamine Residues are Localized within Domains Mediating Synapsin I Interactions," J. Neurochem., 73:418-428 1999.

Cunha et al., "Use of Protecting Groups in Carbohydrate Chemistry An Advanced Organic Synthesis Experiment," J. Chem. Ed., 76:79-80 1999.

De la Monte and Wands, "Review of insulin and insulin-like growth factor expression, signaling, and malfunction in the central nervous system: relevance to Alzheimer's disease," J. Alzheimers Dis. 7:45-61 2005.

De la Torre, "Alzheimer's Disease is a Vasocognopathy: a New Term to Describe its Nature," Neurol. Res., 26:517-524 2004.

Deng et al., "Regulation Between O-GlcNAcylation and phosphorylation of Neurofilament-M and their Dysregulation in Alzheimer Disease," FASEB J. 22:138-145 2008.

Dennis et al., "Structure and Mechanism of a Bacterial Beta-glucosaminidase Having O-GlcNAcase Activity," Nature Structural & Molecular Biology, 13:365-371 2006.

Dong et al., "Purification and Characterization of an O-GlcNAc Selective N-acetyl-beta-D-Glucosaminidase from Rat Spleen Cytosol," J Biol Chem, 269:19321-19330 1994.

Drouillard et al., "Serratia Marcescens Chitobiase is a Retaining Glycosidase Utilizing Substrate Acetamido Group Participation," Biochemical Journal, 328:945-949 1997.

European Search Report for PCT/CA20060003000.

Fulop et al., "Role of Protein O-linked N-acetyl-glucosamine in Mediating Cell Function and Survival in the Cardiovascular System," *Cardiovasc. Res.*, 78:288-297 2007.

Fulop et al., "Effects of Glucosamine on the isolated rat heart," Faseb Journal, 19 A689:72 2005.

Fulop et al., "Diabetes, the hexosamine biosynthesis pathway and protein O-glycsoylation in the heart," Journal of Molecular and Cellular Cardiology, 37:286(71) 2004.

Fulop et al., "Glucosamine-Induced Cardioprotection mediated by the Hexosamine Biosynthesis Pathway and Increased Levels of O-Linked N-Acetylglucosamine on Nucleocytoplasmic Proteins," Circulation Research, 97:E28 2005.

Gao et al., "Dynamic O-glycosylation of nuclear and cytosolic proteins: cloning and characterization of a neutral, cytosolic beta-N-acetylglucosaminidase from human brain," J Biol Chem., 276:9838-9845 2001.

Gao et al., "Streptozotocin-induced beta-cell death is independent of its inhibition of O-GlcNAcase in pancreatic Min6 cells," Arch Biochem Biophys., 383:296-302 2000.

Garneau et al., "Synthesis of Mono- and Disaccharide Analogs of Moenomycin and Lipid II for Inhibition of Transglycosylase Activity of Penicillin-binding Protein 1b," Bioorganic & Medicinal Chemistry, 12:6473-6494 2004.

Goedert et al., "Multiple Isoforms of Human Microtubule-associated Protein tau: Sequences and Localization in Neurofibrillary tangles of Alzheimer's disease," Neuron 3:519-526 1989.

Goedert et al., "Tau Proteins of Alzheimer Paired Helical Filaments: Abnormal Phosphorylation of all Six Brain Isoforms," Neuron 8:159-168 1992.

Gong et al., "Impaired Brain Glucose Metabolism Leads to Alzheimer Neurofibrillary Degeneration Through a Decrease in Tau O-GlcNAcylation," Journal of Alzheimers Disease 9:1 2006.

Gong et al., "Post-translational Modifications of Tau Protein in Alzheimer's Disease," J Neural Transm. 112:813 2005.

Griffith et al., "O-linked N-acetylglucosamine is Upregulated in Alzheimer Brains," Biochem Biophys Res Commun., 213:424-431 1995.

Griffith et al., "O-linked N-acetylglucosamine Levels in Cerebellar Neurons Respond Reciprocally to Pertubations of Phosphorylation," Eur J Biochem., 262:824-831 1999.

Haltiwanger et al. "Modulation of O-linked N-acetylglucosamine levels on Nuclear and Cytoplasmic Proteins In Vivo using the Peptide O-GlcNAc-beta-N-acetylglucosaminidase Inhibitor O-(2-Acetamido-2-deoxy-D-glucopyranosylidene)amino-N-phenylcarbamate" J Biol Chem., 273:3611-3617 1998.

Haltiwanger et al., "Enzymatic Addition of O-GlcNAc to Nuclear and Cytoplasmic Proteins. Identification of a Uridine Diphospho-N-acetylglucosamine: Peptide beta-N-acetylglucosaminyltransferase," J Biol Chem., 265:2563-2568 1990.

Hanover et al., "Elevated O-linked N-acetylglucosamine Metabolism in Pancreatic Beta-cells," Arch Biochem Biophys., 362:38-45 1999.

Hanover, "Glycan-dependent Signaling: O-linked N-acetylglucosamine," FASEB J. 15:1865-1876 2001.

Heightman et al., "Recent Insights into Inhibition, Structure, and Mechanism of Configuration-Retaining Glycosidases," Angew Chem Int Edit., 38:750-770 1999.

Henrissat et al., "New families in the Classification of Glycosyl hydrolases Based on Amino Acid Sequence Similarities," Biochem J., 293:781-788 1993.

Henrissat et al., "Updating the Sequence-based Classification of Glycosyl Hydrolases," Biochem J., 316:695-696 1996.

Horsch et al., "N-acetylglucosaminono-1,5-Lactone Oxime and the Corresponding (phenylcarbamoyl)oxime. Novel and Potent Inhibitors of Beta-N-acetylglucosaminidase," Eur. J. Biochem., 197:815-818 1991.

Hoyer et al., "Brain Insulin and Insulin Receptors in aging and Sporadic Alzheimer's Disease," Journal of Neural Transmission, 105:423 1998.

Hoyer, "Brain glucose and energy metabolism abnormalities in sporadic Alzheimer disease. Causes and consequences: an update," Exp. Gerontol., 35:1363-1372 2000.

Hoyer, "Causes and consequences of disturbances of cerebral glucose metabolism in sporadic Alzheimer disease: therapeutic implications," Adv, Exp. Med. Biol., 541:135-152 2004.

Huang et al. "The hexosamine biosynthesis pathway negatively regulates IL-2 production by Jurkat T cells" Cell Immunol., 245:1 2007.

Iqbal et al., "Alzheimer Neurofibrillary Degeneration: Therapeutic Targets and High-Throughput Assays," J Mol Neurosci., 20:425 2003.

Iqbal et al., "Pharmacological Targets to Inhibit Alzheimer Neurofibrillary Degeneration," J Neural Transm Suppl., 309 2002.

Isac-Garca et al., "Reactivity of 2-deoxy-2-iodoglycosol Isothiocyanates with O-, S-, and N-nucleophiles. Synthesis of Glycopyranoso-fused Thiazoles," Journal of Org. Chem., Universidad de Granada, 69:202-205 2004.

Ito, "Synthesis and Nuclear Magnetic Resonance Spectrum of 3',4',6'-Tri-O-Acetyl-2-(Methylthio)-D-Glucopyrano[2',1': 4,5]-2-Thiazoline," Can. J. Chem., 44:94-97 1966.

Iyer and Hart, "Roles of the tetratricopeptide repeat domain in O-GlcNAc transferase targeting and protein substrate specificity," J. Biol. Chem., 278:24608-24616 2003.

Iyer et al., "Identification and cloning of a novel family of coiled-coil domain proteins that interact with O-GlcNAc transferase," J. Biol. Chem., 278:5399-5409 2003.

Jochims and Seeliger, "Isocyanato-UND Isothiocyanato-Derivate Des $_D$-Glucosamines," Tetrahedron, 21:2611 1965.

Jackson et al., "O-Glycosylation of Eukaryotic Transcription Factors: Implications for Mechanisms of Transcriptional Regulation," Cell 55:125-133 1988.

Jagust et al., "Diminished glucose transport in Alzheimer's disease: dynamic PET studies," J. Cereb. Blood Flow Metab., 11:323-330 1991.

Jeyakumar et al. "Storage solutions: treating lysosomal disorders of the brain," Nat Rev Neurosci.; 6(9):713-725 2005.

Jinek et al., "The superhelical TPR-repeat domain of O-linked GlcNAc transferase exhibits structural similarities to importin alpha," Nat. Struct. Mol. Biol., 11:1001-1007, 2004.

Jones et al., "Purification, properties, kinetics, and mechanism of beta-N-acetylglucosamidase from *Aspergillus niger*," J Biol Chem., 255:11861-11569 1980.

Junod et al., "Studies of the diabetogenic action of streptozotocin," Proc. Soc. Exp. Biol. Med., 126:201-205 1967.

Kalaria and Harik, "Reduced glucose transporter at the blood-brain barrier and in cerebral cortex in Alzheimer disease," J. Neurochem., 53:1083-1088 1989.

Kamemura et al., "Dynamic interplay between O-glycosylation and O-phosphorylation of nucleocytoplasmic proteins: alternative glycosylation/phosphorylation of THR-58, a known mutational hot spot of c-Myc in lymphomas, is regulated by mitogens," J. Biol. Chem., 277:19229-19235 2002.

Kamemura et al., "Dynamic Interplay Between O-glycosylation and O-phosphorylation of Nucleocytoplasmic Proteins: a new Paradigm for Metabolic Control of Signal Transduction and Transcription," Prog Nucleic Acid Res Mol Biol., 73:107-136 2003.

Kelly et al., "RNA Polymerase II is a Glycoprotein. Modification of the CO OH-Terminal Domain by O-GlcNAc" J Biol Chem., 268:10416-10424 1993.

Knapp et al., "Tautomeric modification of GlcNAc-thiazoline" Organic Letters, 9:2321-2324 2007.

Knapp et al., "New Glycomimetics: Anomeric Sulfonates, Sulfenamides, and Sulfonamides," Journal of Organic Chemistry, 71:1380-1389 2006.

Knapp et al., "Shortcut to Mycothiol Analogues," Organic Letters, 4:4337-4339 2002.

Knapp et al., "The Surprise Synthesis of Alpha-GlcNAc 1-C-Sulfonates," Tetrahedron Letters, 43:6075-6078 2002.

Knapp et al., "Alpha -GlcNAc Thioconjugates," Journal of Organic Chemistry, 66:3636-3638 2001.

Knapp et al., "An Allosamizoline/Glucosamine Hybrid NAGase Inhibitor," SYNLETT, 435-436 1997.

Knapp et al., "NAG-thiazoline, an N-acetyl-β-hexosaminidase inhibitor that implicates acetamido participation," J. Am. Chem. Soc., 118:6804-6805 1996.

Knapp et al., "Addition of trialkylaluminum reagents to glyconolactones. Synthesis of 1-C-methyl GlcNAc oxazoline and thiazoline," Tetrahedron Letters, 43:7101 2002.

Kobayashi et al., "Enzymatic Synthesis of Chondroitin and Its Derivatives Catalyzed by Hyaluronidase", J. Am. Chem. Soc., 125:14357-14369 2003.

Konrad et al., "The potential mechanism of the diabetogenic action of streptozotocin: inhibition of pancreatic beta-cell O-GlcNAc-selective N-acetyl-beta-D-glucosaminidase," Biochem. J. 356:31-41 2001.

Kopke et al., "Microtubule-associated Protein Tau Abnormal phosphorylation of a Non-paired Helical Filament Pool in Alzheimer Disease," J Biol Chem. 268:24374-24384 1993.

Kreppel et al., "Regulation of a cytosolic and nuclear O-GlcNAc transferase. Role of the tetratricopeptide repeats," J Biol Chem. 274:32015-32022 1999.

Kreppel, "Dynamic Glycosylation of Nuclear and Cytosolic Proteins Cloning and Characterization of a unique O-GlcNAc Transferase with Multiple Tetratricopeptide Repeats" *J. Biol Chem.* 2729308-9315 1997.

Kroncke et al., "Nitric oxide generation during cellular metabolization of the diabetogenic N-methyl-N-nitroso-urea streptozotozin contributes to islet cell DNA damage," Biol Chem Hoppe Seyler. 376:179-185 1995.

Ksiezak-Reding et al., "Phosphate Analysis and Dephosphorylation of Modified Tau Associated with Paired Helical Filaments," Brain Res., 597:209-219 1992.

Kuroki et al., "Structural basis of the conversion of T4 lysozyme into a transglycosidase by reengineering the active site," Proc Natl Acad Sci U S A. 96(16):8949-8954 1999.

Lamarre-Vincent et al., "Dynamic glycosylation of the transcription factor CREB: a Potential Role in Gene Regulation," J Am Chem Soc., 125:6612-6613 2003.

Lau et al., "Tau protein phosphorylation as a therapeutic target in Alzheimer's disease," Curr. Top. Med. Chem., 2:395-415 2002.

Le Corre et al., "An Inhibitor of Tau Hyperphosphorylation Prevents Severe Motor Impairments in Tau Transgenic Mice," Proc Natl Acad Sci USA 103:9673 2006.

Lefebvre et al., "Does O-GlcNAc play a role in neurodegenerative diseases?" Expert Rev. Proteomics 2:265-275 2005.

Legler et al., "Bovine N-acetyl-beta-D-glucosaminidase: affinity purification and characterization of its active site with nitrogen containing analogs of N-acetylglucosamine," Biochim. Biophys. Acta., 1080:89-95 1991.

Lemieux et al. "Crystallographic Structure of Human Beta-Hexosaminidase A: Interpretation of TaySachs Mutations and, Loss of GM2 Ganglioside Hydrolysis," Journal of Molecular Biology, 359:913-929 2006.

Li et al., "Casein Kinase 1 Delta Phosphorylates Tau and Disrupts Its Binding to Microtubules," J Biol Chem., 279:15938-15945 2004.

Lillelund et al., "Recent developments of transition-state analogue glycosidase inhibitors of non-natural product origin," Chem. Rev. 102:515-553 2002.

Liu et al., "Streptozotocin, an O-GlcNAcase inhibitor, blunts insulin and growth hormone secretion," Mol Cell Endocrinol., 194:135-146 2002.

Liu et al., "C-2-amido-glycosylation Scope and Mechanism of Nitrogen Transfer," J. Am. Chem. Soc. 33:9789-9797 2002.

Liu et al., "Accumulation of protein O-GlcNAc modification inhibits proteasomes in the brain and coincides with neuronal apoptosis in brain areas with high O-GlcNAc metabolism," J. Neurochem., 89:1044-1055 2004.

Liu et al., "Glutamine-induced protection of isolated rat heart from ischemia/reperfusion injury is mediated via the hexosamine biosynthesis pathway and increased protein O-GlcNAc levels," J. Mol. Cell. Cardiol. 42:177-185 2007.

Liu et al., "Hexosaminidase inhibitors as new drug candidates for the therapy of osteoarthritis," Chem. Biol., 8:701-711 2001.

Liu et al., "Increased hexosamine biosynthesis and protein O-GlcNAc levels associated with myocardial protection against calcium paradox and ischemia," J. Mol. Cell. Cardiol., 40:303-312 2006.

Liu et al., "O-GlcNAcylation regulates phosphorylation of tau: a mechanism involved in Alzheimer's disease," Proc Natl Acad Sci USA.,101:10804-10809 2004.

Liu et al., "O-linked N-Acetylglucosamine Modification of Proteins Protect Isolated Perfused Rat Heart from Ischemial Reperfusion injury," Faseb Journal, 19:A691 2005.

Liu et al., "Glutamine protects isolated rat heart from ischemia/reperfusion injury through the hexosamine biosynthesis pathway," Faseb Journal, 20:A317 2006.

Lubas et al., "Analysis of Nuclear Pore Protein p62 Glycosylation," Biochemistry, 34:1686-1694 1995.

Lubas et al., "Functional Expression of O-linked GlcNAc transferase. Domain Structure and Substrate Specificity," J Biol Chem., 275:10983-10988 2000.

Lubas et al., "O-Linked GlcNAc transferase is a Conserved Nucleocytoplasmic Protein Containing Tetratricopeptide Repeats," J Biol Chem 272:9316-9324 1997.

Macauley et al., "O-GlcNAcase uses substrate-assisted catalysis: kinetic analysis and development of highly selective mechanism-inspired inhibitors," J Biol. Chem., 280:25313-25322 2005.

Maier et al., "The X-ray crystal structure of human beta-hexosaminidase B provides new insights into Sandhoff disease," J Mol. Biol.; 328:669-681 2003.

Marchase et al., "Protection from Ischemis and Hypocolemic Injury by Hyperglycemia is Transduced by Hexosamine Biosynthesis and O-Linked N-Acetylglucosamine on Cytoplasmic Proteins," Circulation, 110:1099 2004.

Mark et al., "Anchimeric assistance in hexosaminidases," Can. J. Chem., 80:1064-1074 2002.

Mark et al., "Crystal structure of human beta-hexosaminidase B: understanding the molecular basis of Sandhoff and Tay-Sachs disease," J Mol Biol.; 327:1093-1109 2003.

Mark et al., "Crystallographic evidence for substrate-assisted catalysis in a bacterial beta-hexosaminidase," J Biol Chem.; 276:10330-10337 2001.

Markovic-Housley et al., "Crystal structure of hyaluronidase, a major allergen of bee venom," Structure; 8:1025-1035, 2000.

Marshall et al., "New insights into the metabolic regulation of insulin action and insulin resistance: role of glucose and amino acids," FASEB J., 5:3031-3036 1991.

McClain et al., "Altered glycan-dependent signaling induces insulin resistance and hyperleptinemia," Proc. Natl. Acad. Sci. U.S.A. 99:10695-10699, 2002.

Miller et al., "Sperm require beta-N-acetylglucosaminidase to penetrate through the egg zona pellucid," Development; 118(4):1279-1289 1993.

Mohan et al., "An Improved Synthesis of 2-Acetamido-2-deoxy-d-gluconohydroximolactone (PUGNAc), A Strong Inhibitor of b-N-Acetylglucosaminidases," Helv Chim Acta, 83:114-118 2000.

Nagy et al., "Glucosamine inhibits angiotensin II-induced cytoplasmic Ca2+ elevation in neonatal cardiomyocytes via protein-associated O-linked N-acetylglucosamine," Am. J. Physiol. Cell. Physiol., 290:C57-65 2006.

Noble et al., "Inhibition of Glycogen Synthase Kinase-3 by lithium Correlates with Reduced Tauopathy and Degeneration In Vivo," Proc Natl Acad Sci. USA., 102:6990 2005.

Not et al., "Glucosamine administration improves survival following trauma-hemorrhage in rats," Faseb Journal, 20:A1471 2006.

Okuyama et al., "Cytosolic O-GlcNAc accumulation is not involved in beta-cell death in HIT-T15 or Min6," Biochem Biophys Res Commun.; 287(2):366-371 2001.

Parker et al., "Hyperglycemia and inhibition of glycogen synthase in streptozotocin-treated mice: role of O-linked N-acetylglucosamine," J. Biol. Chem., 279:20636-20642 2004.

Reid et al., "Inhibition of Membrane Bound Lytic Transglycosylase B by NAG-thiazoline," FEBS Letters, 574:73-79 2004.

Ritter et al., "Synthesis of N-acetylglucosamine Thiazoline/lipid II Hybrids," Tetrahedron Letters, 42:615-618 2001.

Roeser et al., "Role of sugar hydroxyl groups in glycoside hydrolysis. Cleavage mechanism of deoxyglucosides and related substrates by beta-glucosidase A3 from *Aspergillus wentii*," Biochim Biophys Acta.; 657(2):321-333 1981.

Roos et al., "Streptozotocin, an analog of N-acetylglucosamine, blocks the removal of O-GlcNAc from intracellular proteins," Proc Assoc Am Physicians., 110:422-432 1998.

Roos et al., "O glycosylation of an Sp1-derived Peptide Blocks Known Sp1 Protein Interactions," Mol Cell Biol 17:6472-6480, 1997.

Roquemore, "Dynamic O-GlcNAcylation of the Small Heat Shock Protein Alpha B-crystallin," Biochemistry 35: 3578-3586 1996.

Sheldon et al., "Functional Analysis of a Group A Streptococcal Glycoside Hydrolase Spy1600 from Family 84 Reveals it is a Beta-N-Acetylglucosaminidase and not a Hyaluronidase," Biochemical Journal, 399:241-247 2006.

Shitara et al., "A facile synthesis of D-glucose-type gem-diamine 1-N-iminosugars: a new family of glucosidase inhibitors," Bioorg Med Chem. 7:1241-1246 1997.

Simpson et al., "Decreased concentrations of GLUT1 and GLUT3 glucose transporters in the brains of patients with Alzheimer's disease," Ann. Neurol. 35:546-551, 1994.

Stubbs et al., "A Divergent Synthesis of 2-acyl Derivatives of PUGNAc Yields Selective inhibitors of O-GlcNAcase," Organic and Bimolecular Chemistry, 4:839-845 2006.

Terwisscha et al., "Stereochemistry of chitin hydrolysis by a plant chitinase/lysozyme and X-ray structure of a complex with allosamidin: evidence for substrate assisted catalysis," Biochemistry. ; 34(48):15619-15623 1995.

Tews et al., "Bacterial chitobiase structure provides insight into catalytic mechanism and the basis of Tay-Sachs disease," Nat Struct Biol.; 3(7):638-648, 1996.

Toleman et al., "Characterization of the Histone Acetyltransferase (HAT) Domain of a Bifunctional Protein with Activable O-GlcNAcase and HAT Activities," J Biol Chem., 2004.

Torres et al., "Topography and Polypeptide Distribution of Terminal N-acetylglucosamine residues on the Surfaces of Intact Lymphocytes. Evidence for O-linked GlcNAc," J Biol Chem. 259:3308-3317 1984.

Triggs-Raine et al., "Naturally occurring mutations in GM2 gangliosidosis: a compendium," Adv. Genet., 44:199-224 2001.

Tropak et al., "Pharmacological enhancement of beta-hexosaminidase activity in fibroblasts from adult Tay-Sachs and Sandhoff Patients," J Biol Chem., 279:13478-13487, 2004..

U. J. G. Conference, In *US/Japan Glyco 2004 Conference*, Honolulu, Hawaii, 2004.

Ueno et al., "Purification and Properties of Neutral Beta-N-acetylglucosaminidase from Carp Blood," Biochim Biophys Acta., 1074:79-84 1991.

van den Berg et al., "Design and synthesis of 2-acetamidomethyl derivatives of isofagomine as potential inhibitors of human lysosomal beta-hexosaminidases" Bioorg Med Chem, 12:891-902, 2004.

Vocadlo et al., "Catalysis by hen egg-white lysozyme proceeds via a covalent intermediate" Nature, 412:835-838 2001.

Vocadlo et al., "Detailed comparative analysis of the catalytic mechanisms of beta-N-acetylglucosaminidases from families 3 and 20 of glycoside hydrolases," Biochemistry.; 44(38):12809-12818 2005.

Vocadlo et al. "Mechanism of action and identification of Asp242 as the catalytic nucleophile of Vibrio furnisii Nacetyl-beta-D-glucosaminidase using 2-acetamido-2-deoxy-5-fluoro-alpha-L-idopyranosyl fluoride" Biochemistry. Jan. 11, 2000;39(1):117-126.

Vocadlo, "Pharmacological Elevation of O-GlcNAc Levels In Vivo Using Potent and Selective O-GLcNAcase Inhibitors," XXIIIrd International Carbohydrate Symposium, Whistler, B.C. Jul. 23-28, 2006.

Vosseller et al., "Elevated Nucleocytoplasmic Glycosylation by O-GlcNAc Results in Insulin Resistance Associated with Defects in Akt Activation in 3T3-L1 Adipocytes," Proc Natl Acad Sci., USA 99: 5313-5318 2002.

Wells et al., "Glycosylation of nucleocytoplasmic proteins: signal transduction and O-GlcNAc," Science 291:2376-2378 2001.

Wells et al., "O-GlcNAc Transferase is in a Functional Complex with Protein Phosphatase 1 Catalytic Subunits," J Biol Chem 279 :38466-38470 2004.

Whitworth et al., "Analysis of PUGNAc and NAG-thiazoline as Transition State Analogues for Human O-GlcNAcase: Mechanistic and Structural Insights into Inhibitor Selectivity and Transition State Poise," J. Am. Chem. Soc., 129:635-644 2007.

Yamada et al., "Preventive and therapeutic effects of large-dose nicotinamide injections on diabetes associated with insulitis. An observation in nonobese diabetic (NOD) mice", Diabetes 31:749-753 1982.

Yamamoto et al., "Streptozotocin and alloxan induce DNA strand breaks and poly(ADP-ribose) synthetase in pancreatic islets" Nature, 294:284-286 1981.

Yang et al., "Recruitment of O-GlcNAc transferase to promoters by corepressor mSin3A: coupling protein O-GlcNAcylation to transcriptional repression," Cell, 110:69-80 2002.

Yang et al., "Glucosamine administration during resuscitation improves organ function after trauma hemorrhage," Shock, 25:600-607 2006.

Yang et al., "Modification of p53 with O-linked N-acetylglucosamine regulates p53 activity and stability," Nat. Cell Biol., 8:1074-1083 2006.

Yao and Coleman, "Reduction of O-linked N-acetylglucosamine-modified assembly protein-3 in Alzheimer's disease," J. Neurosci., 18:2399-2411 1998.

Zachara et al., "Dynamic O-GlcNAc modification of nucleocytoplasmic proteins in response to stress. A survival response of mammalian cells," J Biol Chem., 279:30133-30142 2004.

Zachara et al., "O-GlcNAc a sensor of cellular state: the role of nucleocytoplasmic glycosylation in modulating cellular function in response to nutrition and stress," Biochim Biophys Acta., 1673(1-2):13-28 2004.

Zechel et al., "Glycosidase mechanisms: anatomy of a finely tuned catalyst," Acc Chem Res.; 33(1):11-18 2000.

Zhang, "O-GlcNAc Modification is an Endogenous Inhibitor of the Proteasome," Cell 115:715-725 2003.

Zhou et al., "Lysosomal glycosphingolipid recognition by NKT cells," Science 306:1786-1789 2004.

Zhu et al., "Insulin signaling, diabetes mellitus and risk of Alzheimer disease," J. Alzheimers Dis., 7:81-84 2005.

Zou et al., "Increasing protein O-GlcNAc levels by inhibition of O-GlcNAcase improves cardiac function following trauma hemorrhage and resuscitation in rat," FASEB J.:A1471 2006.

Zou et al., "The protective effects of PUGNAc on cardiac function after trauma-hemorrhage are mediated via increased protein O-GlcNAc levels," Shock, 27(4):402-408 2007.

Zou et al., "Glucosamine improves recovery following trauma hemorrhage in rat," Faseb Journal, 19:A1224 2005.

* cited by examiner

SELECTIVE GLYCOSIDASE INHIBITORS AND USES THEREOF

CROSS REFERENCE TO RELATED APPLICATIONS

This application is the U.S. National Stage of International Application No. PCT/CA2007/001554, filed Aug. 31, 2007, which in turn claims the benefit of U.S. Provisional application Ser. Nos. 60/841,196, filed on Aug. 31, 2006, and 60/895,663, filed Mar. 19, 2007, which are hereby incorporated by reference.

FIELD OF THE INVENTION

This application relates to compounds which selectively inhibit glycosidases and uses thereof.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage.[1] This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase).[2-5] A second enzyme, known as O-GlcNAcase[6,7] removes this post-translational modification to liberate proteins making the O-GlcNAc-modification a dynamic cycle occurring several times during the lifetime of a protein.[8]

O-GlcNAc-modified proteins regulate a wide range of vital cellular functions including, for example, transcription,[9-12] proteasomal degradation,[13] and cellular signaling.[14] O-GlcNAc is also found on many structural proteins.[15-17] For example, it has been found on a number of cytoskeletal proteins, including neurofilamnent proteins,[18,19] synapsins,[6,20] synapsin-specific clatrin assembly protein AP-3,[7] and ankyrinG.[14] O-GlcNAc modification has been found to be abundant in the brain.[21,22] It has also been found on proteins clearly implicated in the etiology of several diseases including Alzheimer's disease (AD) and cancer.

For example, it is well established that AD and a number of related tauopathies including Downs' syndrome, Pick's disease, Niemrann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated.[23,24] Tau in healthy brain tissue bears only 2 or 3 phosphate groups, whereas those found in the brains of AD patients bear, on average, 8 phosphate groups.[25,26] A clear parallel between NFT levels in the brains of AD patients and the severity of dementia strongly supports a key role for tau dysfunction in AD.[27,28] The precise causes of this hyperphosphorylation of tau remain elusive. Accordingly, considerable effort has been dedicated toward: a) elucidating the molecular physiological basis of tau hyperphosphorylation;[29] and b) identifying strategies that could limit tau hyperphosphorylation in the hope that these might halt, or even reverse, the progression of Alzheimer's disease[30-33] Thus far, several lines of evidence suggest that up-regulation of a number of kinases may be involved in hyperphosphorylation of tau,[21,34,35] although very recently, an alternative basis for this hyperphosphorylation has been advanced.[21]

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated.[36-38] Consistent with this observation, it has been found that increases in phosphorylation levels result in decreased O-GlcNAc levels and conversely, increased O-GlcNAc levels correlate with decreased phosphorylation levels.[39] This reciprocal relationship between O-GlcNAc and phosphorylation has been teamed the "Yin-Yang hypothesis"[40] and has gained strong biochemical support by the recent discovery that the enzyme OGTase[4] forms a functional complex with phosphatases that act to remove phosphate groups from proteins.[41] Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD.[7,42] Hyperphosphorylated tau in human AD brains has markedly lower levels of O-GlcNAc than are found in healthy human brains.[21] Very recently, it has been shown that O-GlcNAc levels of soluble tau protein from human brains affected with AD are markedly lower than those from healthy brain.[21] Furthermore, PHF from diseased brain was suggested to lack completely any O-GlcNAc modification whatsoever.[21] The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosaminidases inhibitor was used to increase tau O-GlcNAc levels, whereupon it was observed that phosphorylation levels decreased.[21] The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging.[43] Within the brains of AD patients marked decreases in glucose utilization occur and are thought to be a potential cause of neurodegeneration.[44] The basis for this decreased glucose supply in AD brain[45-47] is thought to stem from any of decreased glucose transport,[48,49] impaired insulin signaling,[50,51] and decreased blood flow.[52]

In light of this impaired glucose metabolism, it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc).[53] UDP-GlcNAc is a substrate of the nucleocytoplasmic enzyme O-GlcNAc transferase (OGTase),[2-5] which acts to post-translationally add GlcNAc to specific serine and threonine residues of numerous nucleocytoplasmic proteins. OGTase recognizes many of its substrates[54,55] and binding partners[41,56] through its tetratiicopeptide repeat (TPR) domains.[57,58] As described above, O-GlcNAcase[6,7] removes this post-translational modification to liberate proteins making the O-GlcNAc-modification a dynamic cycle occurring several times during the lifetime of a protein.[8] O-GlcNAc has been found in several proteins on known phosphorylation Sites,[10,37,38,59] including tau and neurofilaments.[60] Additionally, OGTase shows unusual kinetic behaviour making it exquisitely sensitive to intracellular UDP-GlcNAc substrate concentrations and therefore glucose supply.[41]

Consistent with the known properties of the hexosamine biosynthetic pathway, the enzymatic properties of OGTase, and the reciprocal relationship between O-GlcNAc and phosphorylation, it has been shown that decreased glucose availability in brain leads to tau hyperphosphorylation.[44] Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention[61] comes from recent studies showing that when transgenic mice harbouring human tau are treated with kinase inhibitors, they do not develop typical motor defects[33] and, in another case,[32] show decreased levels of insoluble tau. These studies provide a clear link between lowering tau phosphorylation levels and alleviating AD-like behavioural symptoms in a murine model of this disease.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischernialreperfusion,[62-68] trauma hemorrhage,[69-71] hypervolemic shock,[72] and calcium paradox.[62,73] Moreover, strong evidence indicates that these cardioprotective effects are mediated by elevated levels of protein O-GlcNAc modification.[62,63,65,68,70,73-76] There is also evidence that the O-GlcNAc modification plays a role in a variety of neurodegenerative diseases, including Parkinson's disease and Huntington's disease.[77]

Humans have three genes encoding enzymes that cleave terminal β-N-acetyl-glucosamine residues from glycoconjugates. The first of these encodes the enzyme O-glycoprotein 2-acetamido-2-deoxy-β-D-glucopyranosidase (O-GlcNAcase). O-GlcNAcase is a member of family 84 of glycoside hydrolases that includes enzymes from organisms as diverse as prokaryotic pathogens to humans (for the family classification of glycoside hydrolases see Coutinho, P. M. & Henrissat, B. (1999) Carbohydrate-Active Enzymes server at URL: http://afmb.cnrs-mrs.fr/CAZY/.[27,28] O-GlcNAcase acts to hydrolyse O-GlcNAc off of serine and threonine residues of post-translationally modified proteins.[1,6,7,78,79] Consistent with the presence of O-GlcNAc on many intracellular proteins, the enzyme O-GlcNAcase appears to have a role in the etiology of several diseases including type 11 diabetes,[14,80] AD,[16,21,81] and cancer.[22,82] Although O-GlcNAcase was likely isolated earlier on,[18,19] about 20 years elapsed before its biochemical role in acting to cleave O-GlcNAc from serine and threonine residues of proteins was understood.[6] More recently O-GlcNAcase has been cloned,[7] partially characterized,[20] and suggested to have additional activity as a histone acetyltransferase.[20] However, little was known about the catalytic mechanism of this enzyme.

The other two genes, HEXA and HEXB, encode enzymes catalyzing the hydrolytic cleavage of terminal β-N-acetylglucosamine residues from glycoconjugates. The gene products of HEXA and HEXB predominantly yield two dimeric isozymes, hexosaminidase A and hexosaminidase B, respectively. Hexosaminidase A (αβ), a heterodimeric isozyme, is composed of an α- and a β-subunit. Hexosaminidase B (ββ), a homodimeric isozyme, is composed of two β-subunits. The two subunits, α- and β-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B.[83] These enzymatic deficiencies cause an accumulation of glycolipids and glycoconjugates in the lysosomes resulting in neurological impairment and deformation. The deleterious effects of accumulation of gangliosides at the organismal level are still being uncovered.[84]

As a result of the biological importance of these β-N-acetyl-glucosaminidases, small molecule inhibitors of glycosidases[85-88] have received a great deal of attentions,[89] both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

A few of the better characterized inhibitors of β-N-acetyl-glucosaminidases which have been used in studies of O-GlcNAc post-translational modification within both cells and tissues are streptozotocin (STZ), 2'-methyl-α-D-glucopyrano-[2,1-d]-Δ2'-thiazoline (NAG-thiazoline) and O-(2-acetamido-2-deoxy-D-glucopyranosylidene)amino N-phenylcarbamate (PUGNAc).[14,90-93]

STZ has long been used as a diabetogenic compound because it has a particularly detrimental effect on β-islet cells.[94] STZ exerts its cytotoxic effects through both the alkylation of cellular DNA[94,95] as well as the generation of radical species including nitric oxide.[96] The resulting DNA strand breakage promotes the activation of poly(ADP-ribose) polymerase (PARP)[97] with the net effect of depleting cellular NAD+ levels and, ultimately, leading to cell death.[98,99] Other investigators have proposed instead that STZ toxicity is a consequence of the irreversible inhibition of O-GlcNAcase, which is highly expressed within β-islet cells.[90,100] This hypothesis has, however, been brought into question by two independent research groups.[101,102] Because cellular O-GlcNAc levels on proteins increase in response to many forms of cellular stress103 it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase[104] and although it has been proposed by others that STZ acts to irreversibly inhibit O-GlcNAcase,[105] there has been no clear demonstration of this mode of action Recently, it has been shown that STZ does not irreversibly inhibit O-GlcNAcase.[106]

NAG-thiazoline has been found to be a potent inhibitor of family 20 hexosaminidases,[88,107] and more recently, the family 84 O-GlcNAcases.[106] Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase[6,108] and the family 20 human β-hexosaminidases.[109] This molecule, developed by Vasella and coworkers, was found to be a potent competitive inhibitor of the β-N-acetyl-glucosaminidases from *Canavalia ensiformis, Mucor rouxii*, and the β-hexosaminidase from bovine kidney.[86] It has been demonstrated that administration of PUGNAc in a rat model of trauma hemorrhage decreases circulating levels of the pro-inflammatory cytokines TNF-α and IL-6.[110] It has also been shown that administration of PUGNAc in a cell-based model of lymphocyte activation decreases production of the cytokine IL-2.[111] Recent studies have indicated that PUGNAc can be used in an animal model to reduce myocardial infarct size after left coronary artery occlusions.[112] Of particular significance is the fact that elevation of O-GlcNAc levels by administration of PUGNAc, an inhibitor of O-GlcNAcase, in a rat model of trauma hemorrhage improves cardiac function.[110,113] In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells.[114]

International patent application PCT/CA20061000300, filed 1 Mar. 2006, published under No. WO 2006/092049 on 8 Sep. 2006, which is hereby incorporated by reference, describe some more selective inhibitors of O-GlcNAcase, compared to NAG-thiazoline or PUGNAc.

SUMMARY OF THE INVENTION

The invention provides, in part, compounds for selectively inhibiting glycosidases, prodrugs of the compounds, uses of the compounds and the prodrugs, pharmaceutical compositions including the compounds or prodrugs of the compounds, and methods of treating diseases and disorders related to deficiency or overexpression of O-GlcNAcase, accumulation or deficiency of O-GlcNAc.

In one aspect, the invention provides a compound of Formula (I) or a pharmaceutically acceptable salt thereof:

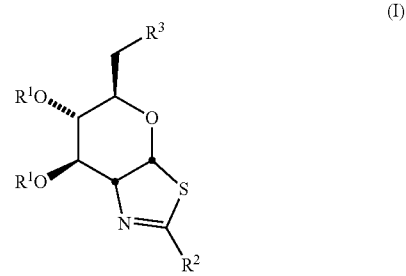

(I)

where each $R^1$ is independently a non-interfering substituent; $R^2$ is alkyl, aryl, heteroaryl, $OR^4$, $NR^4_2$, and $NR^4OR^4$, each of which may be optionally substituted with a non-interfering substituent; $R^3$ is $OR^4$, N3, or $NR^4_2$; and each $R^4$ is independently a non-interfering substituent, with the proviso that when each $R^1$ is H and $R^3$ is OH, $R^2$ excludes $CH_3$, $CH_2CH_3$, $(CH_2)_2CH_3$, $(CH_2)_3CH_3$, $(CH_2)_4CH_3$, $(CH_2)_6CH_3$, $CH(CH_3)_2$, $CH_2CH(CH_3)_2$, NH(phenyl), NH(4-methoxyphenyl), $N(CH_3)_2$, $(CH_2)_2P(O)(OH)(OCH_3)$, and $(CH_2)_2P(O)(OH)(O(CH_2)_7CH_3)$; and with the proviso that when each $R^1$ is $COCH_3$ and $R^3$ is $OC(O)CH_3$, $R^2$ excludes $CH_3$, $CH_2CH_3$, $(CH_2)_2CH_3$, $(CH_2)_3CH_3$, $(CH_2)_4CH_3$, $(CH_2)_6CH_3$, $CH(CH_3)_2$, $CH_2CH(CH_3)_2$, NH(phenyl), NH(4-methoxyphenyl), $N(CH_3)_2$, $(CH_2)_2P(O)(OH)(OCH_3)$, and $(CH_2)_2P(O)(OH)(O(CH_2)_7CH_3)$, $NHCH_3$, $NH(CH_2)_2CH_3$, $NHCH(CH_3)_2$, $NH(CH_2)_3CH_3$, NH(cyclohexyl), NH(benzyl), $CH_2Br$, $CHBr_2$, $CH_2P(O)(OCH_2CH_3)_2$, $(CH_2)_2P(O)(OCH_3)(O(CH_2)_7CH_3)$, $(CH_2)_2P(O)(OCH_3)_2$, $(CH_2)_2P(O)(OCH_3)_2$, $N(COCH_3)(phenyl)$, and $N(COCH_3)(4\text{-methoxyphenyl})$; and with the proviso that Formula (I) excludes compounds 74 to 85 described in Table 2.

In alternative embodiments, each $R^1$ may be connected to form an additional ring structure; or when $R^3$ is $OR^4$, $R^4$ may be connected to either $R^1$ to form an additional ring structure.

In alternative embodiments, the non-interfering substituent may be alkyl, alkenyl, alkynyl, aryl, arylalkyl, arylalkenyl, or arylalkynyl, or may include one or more heteroatoms selected from P, O, S, and N. The non-interfering substituent may be optionally substituted.

In alternative embodiments, $R^1$ may be H or $C(O)CH_3$; $R^2$ may be $CH_2F$, $CHF_2$, $CF_3$, $(CH_2)_2CH=CH_2$, $(CH_2)CH=CHCH_3$, $CH_2OCH_3$, $(CH_2)_2CF_3$, cyclopropylmethyl, phenyl, benzyl, $NH_2$, $NHCH_3$, $NH_1CH_2CH_3$, $NH(CH_2>CH_3$, $NH(CH_2)_3CH_3$, $NHCH_2CH=CH_2$, NHcyclopropyl, $NHCH_2CH_2F$, $NHCH_2CHF_2$, $NHCH_2CF_3$, $NHCH_2CH_2OH$, $NHCH_2CH_2OC(O)CH_3$, $N(CH_3)_2$, $N(CH_3)(CH_2CH_3)$, $NHOCH_3$, $OCH_3$, or $(CH_2)_2CH_3$; $R^3$ may be OH, $OC(O)CH_3$, $N_3$, or $NH_2$.

In alternative embodiments, the compound may be a compound described in Table 1; the compound may exclude one or more of the compounds described in Table 2 or Table 3; the compound may be a prodrug; the compound may selectively inhibit an O-glycoprotein 2-acetamido-2-deoxy-β-D-glucopyranosidase (O-GlcNAcase); the compound may selectively bind an O-GlcNAcase (e.g., a mammalian O-GlcNAcase); the compound may selectively inhibit the cleavage of a 2-acetamido-2-deoxy-β-D-glucopyranoside (O-GlcNAc); the compound may not substantially inhibit a mammalian β-hexosaminidase.

In alternative aspects, the invention provides a pharmaceutical composition including a compound according to the invention, in combination with a pharmaceutically acceptable carrier.

In alternative aspects, the invention provides methods of selectively inhibiting an O-GlcNAcase, or of inhibiting an O-GlcNAcase in a subject in need thereof, or of increasing the level of O-GlcNAc, or of treating a neurodegenerative disease, a tauopathy, cancer or stress, in a subject in need thereof, by administering to the subject an effective amount of a compound of Formula (I) or a pharmaceutically acceptable salt thereof:

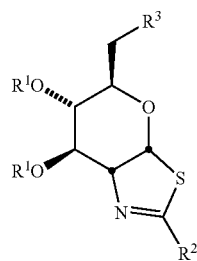

(I)

wherein each $R^1$ may be independently a non-interfering substituent; $R^2$ may be allyl, aryl, heteroaryl, $OR^4$, $NR^4{}_2$, and $NR^4OR^4$, each of which may be optionally substituted with a non-interfering substituent; $R^3$ may be $OR^4$, $N_3$, or $NR^4{}_2$; and each $R^4$ may be independently a non-interfering substituent, with the proviso that when each $R^1$ is H and $R^3$ is OH, $R^2$ excludes $CH_2CH_3$, $(CH_2)_2CH_3$, $(CH_2)_3CH_3$, $(CH_2)_4CH_3$, $CH(CH_3)_2$, and $CH_2CH(CH_3)_2$; and with the proviso that when each $R^1$ is $COCH_3$ and $R^3$ is $OC(O)CH_3$, $R^2$ excludes $CH_2CH_3$, $(CH_2)_2CH_3$, $(CH_2)_3CH_3$, $(CH_2)_4CH_3$, $CH(CH_3)_2$, and $CH_2CH(CH_3)_2$. The condition may be Alzheimer's disease, Amylotrophic lateral sclerosis (ALS), Amylotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegenenition with brain iron accumulation type 1), Multiple system atrophy, Myotonic dystrophy, Niemann-Pick disease (type C), Pallido-ponto-nigral degeneration, Parkinsonism-dementia complex of Guam, Pickes disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, or Parkinson's disease. The stress may be a cardiac disorder, e.g., ischemia; hemorrhage; hypovolemic shock; myocardial infarction; an interventional cardiology procedure; cardiac bypass surgery; fibrinolytic therapy; angioplasty; or stent placement.

In alternative aspects, the invention provides a method of treating an O-GlcNAcase mediated condition that excludes a neurodegenerative disease, a tauopathy, cancer or stress, in a subject in need thereof, by administering to the subject an effective amount of a compound of Formula (I) or a pharmaceutically acceptable salt thereof:

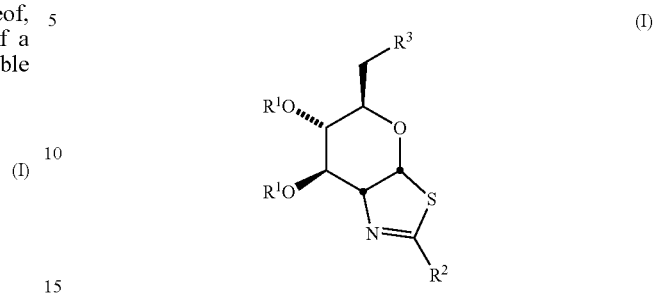

(I)

wherein each $R^1$ may be independently a non-interfering substituent; $R^2$ may be alkyl, aryl, heteroaryl, $OR^4$, $NR^4{}_2$, and $NR^4OR^4$, each of which may be optionally substituted with a non-interfering substituent; $R^3$ may be $OR^4$, $N_3$, or $NR^4{}_2$; and each $R^4$ may be independently a non-interfering substituent. In some embodiments, the condition may be inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, systemic lupus erythematosus, myasthenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinophilic myotis, and eosinophilic fascitis; graft rejection, in particular but not limited to solid organ transplants, such as heart, lung, liver, kidney, and pancreas transplants (e.g. kidney and lung allografts); epilepsy; pain; stroke, e.g., neuroprotection following a stroke.

In alternative embodiments, $R^1$ may be H or $C(O)CH_3$; $R^2$ may be $CH_2F$, $CHF_2$, $CF_3$, $(CH_2)_2CH=CH_2$, $(CH_2)_2CH=CHCH_3$, $CH_2OCH_3$, $(CH_2)_2CF_3$, cyclopropylmethyl, phenyl, benzyl, $NH_2$, $NHCH_3$, $NHCH_2CH_3$, $NH(CH_2)_2CH_3$, $NH(CH_2)_3CH_3$, $NHCH_2CH=CH_2$, NHcyclopropyl, $NHCH_2CH_2F$, $NHCH_2CHF_2$, $NHCH_2CF_3$, $NHCH_2CH_2OH$, $NHCH_2CH_2OC(O)CH_3$, $N(CH_3)_2$, $N(CH_3)(CH_2CH_3)$, $NHOCH_3$, $OCH_3$, or $(CH_2)_2CH_3$; $R^3$ may be OH, $OC(O)CH_3$, $N_3$, or bed; the compound may be selected from the group consisting of one or more of the compounds described in Table 2 and Table 3. The administering may increase the level of O-GlcNAc in the subject. The subject may be a human.

In alternative aspects, the invention provides use of a compound of an effective amount of a compound of Formula (I) or a pharmaceutically acceptable salt thereof:

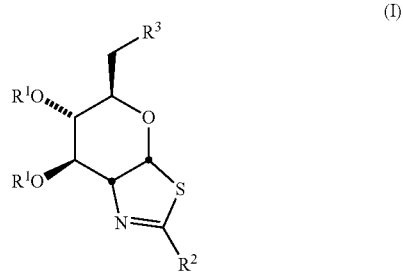

(I)

where each $R^1$ may be independently a non-interfering substituent; $R^2$ may be alkyl, aryl, heteroaryl, $OR^4$, $NR^4_2$, and $NR^4OR^4$, each of which may be optionally substituted with a non-interfering substituent; $R^3$ may be $OR^4$, $N_3$, or $NR^4_2$; and each $R^4$ may be independently a non-interfering substituent, with the proviso that the compound of Formula (I) excludes the compounds described in Tables 2 and 3, in the preparation of a medicament. The medicament may be for selectively inhibiting an O-GlcNAcase, for increasing the level of O-GlcNAc, for treating a condition modulated by an O-GlcNAcase, for treating a neurodegenerative disease, a tauopathy, a cancer, or stress.

In alternative aspects, the invention provides a method for screening for a selective inhibitor of an O-GlcNAcase, by a) contacting a first sample with a test compound; b) contacting a second sample with a compound of Formula (I)

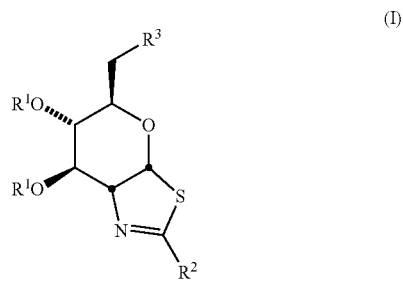

(I)

where each $R^1$ may be independently a non-interfering substituent; $R^2$ may be alkyl, aryl, heteroaryl, $OR^4$, $NR^4_2$, and $NR^4OR^4$, each of which may be optionally substituted with a non-interfering substituent; $R^3$ may be $OR^4$, $N_3$, or $NR^4_2$; and each $R^4$ may be independently a non-interfering substituent, c) determining the level of inhibition of the O-GlcNAcase in the first and second samples, where the test compound is a selective inhibitor of a O-GlcNAcase if the test compound exhibits the same or greater inhibition of the O-GlcNAcase when compared to the compound of Formula (I).

This summary of the invention does not necessarily describe all features of the invention.

BRIEF DESCRIPTION OF THE DRAWINGS

These and other features of the invention will become more apparent from the following description in which reference is made to the appended drawings wherein:

FIGS. 1C (muscle) and 1D (Grain) show Western blots of samples loaded in FIGS. 1A-B and probed using anti-β-actin mAb clone AC-40 followed by an anti-mouse IgG-HRP conjugate. FIGS. 1E (muscle) and 1F (brain) are graphs showing the analysis of the Western blot results by densitometry.

FIG. 3B shows a Western blot of samples loaded in FIG. 3A and probed using an anti-β-actin mAb clone AC-40 followed by an anti-mouse IgG-HRP conjugate.

FIG. 7A shows the Western blot of samples probed with Tau-5 (a phospho-independent tau antibody), and demonstrates equal loading of tau protein. FIGS. 7B-D show Western blots of the same samples probed with specific anti-phospho-tau antibodies, while FIG. 7E shows analysis of the Western blot results by densitometry. FIG. 7F shows a Western blot of whole brain lysates from these animals probed with the primary α-O-GlcNAc antibody, showing increases the global levels of O-GlcNAc in the brains of animals receiving NAG-AB. FIG. 7G shows the same samples as in FIG. 7F, probed using an anti-β-actin antibody and demonstrates equal sample loading.

DETAILED DESCRIPTION

Figure 1:
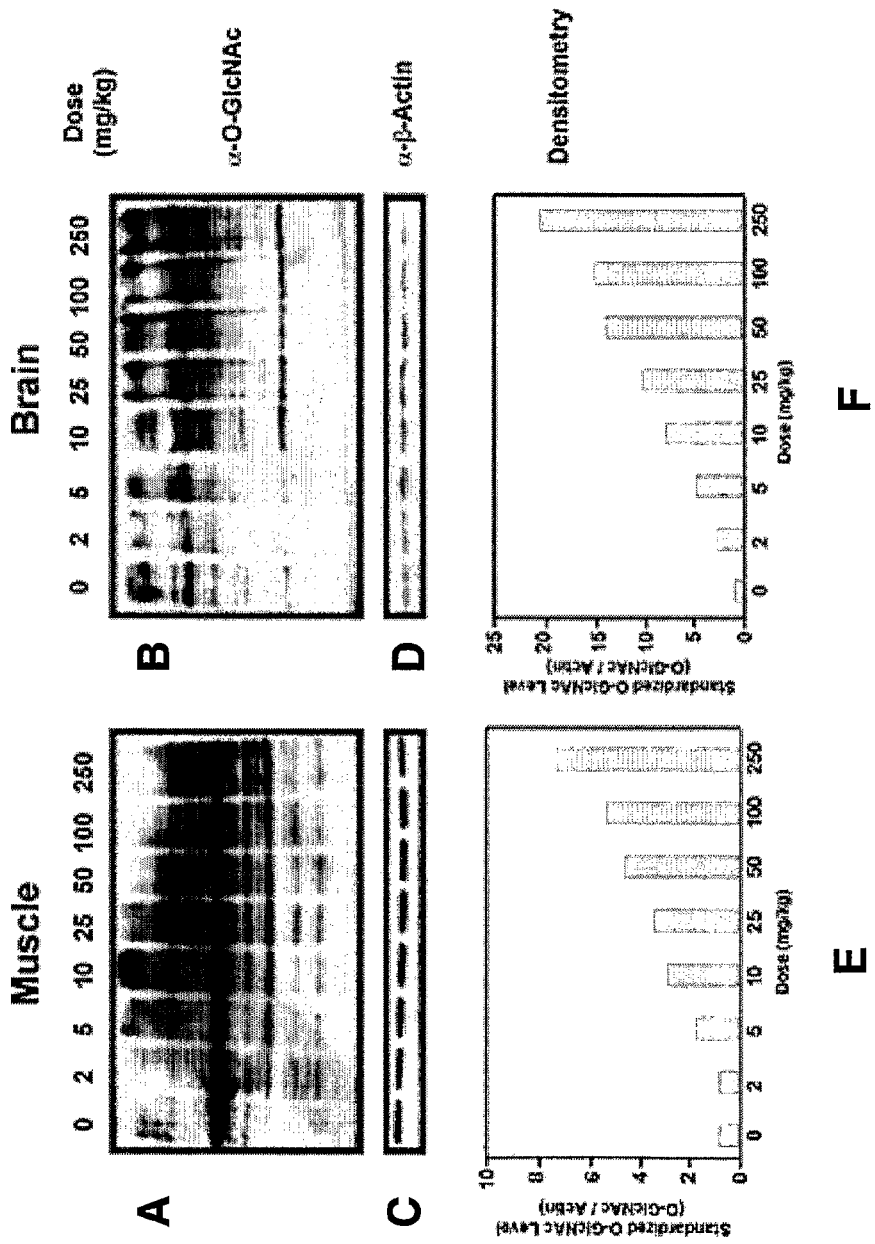
FIGS. 1A-F show Western blots of proteins from muscle and brain tissue of rats injected with various doses of (3aR, 5R,6S,7R,7aR)-5-(hydroxymethyl)-2-propyl-5,6,7,7a-tetrahydro-3aH-pyrano[3,2-d]thiazole-6,7-diol (NAG-Bt) or vehicle alone (PBS). Equal amounts of homogenized muscle (A) and brain (B) tissue from animals treated with the indicated doses of NAG-Bt or vehicle alone (PBS; 0 mg/kg) were separated by SDS-PAGE followed by probing with the primary α-O-GlcNAc antibody and an anti-IgM-mouse IgG-HRP conjugate.
Figure 2:
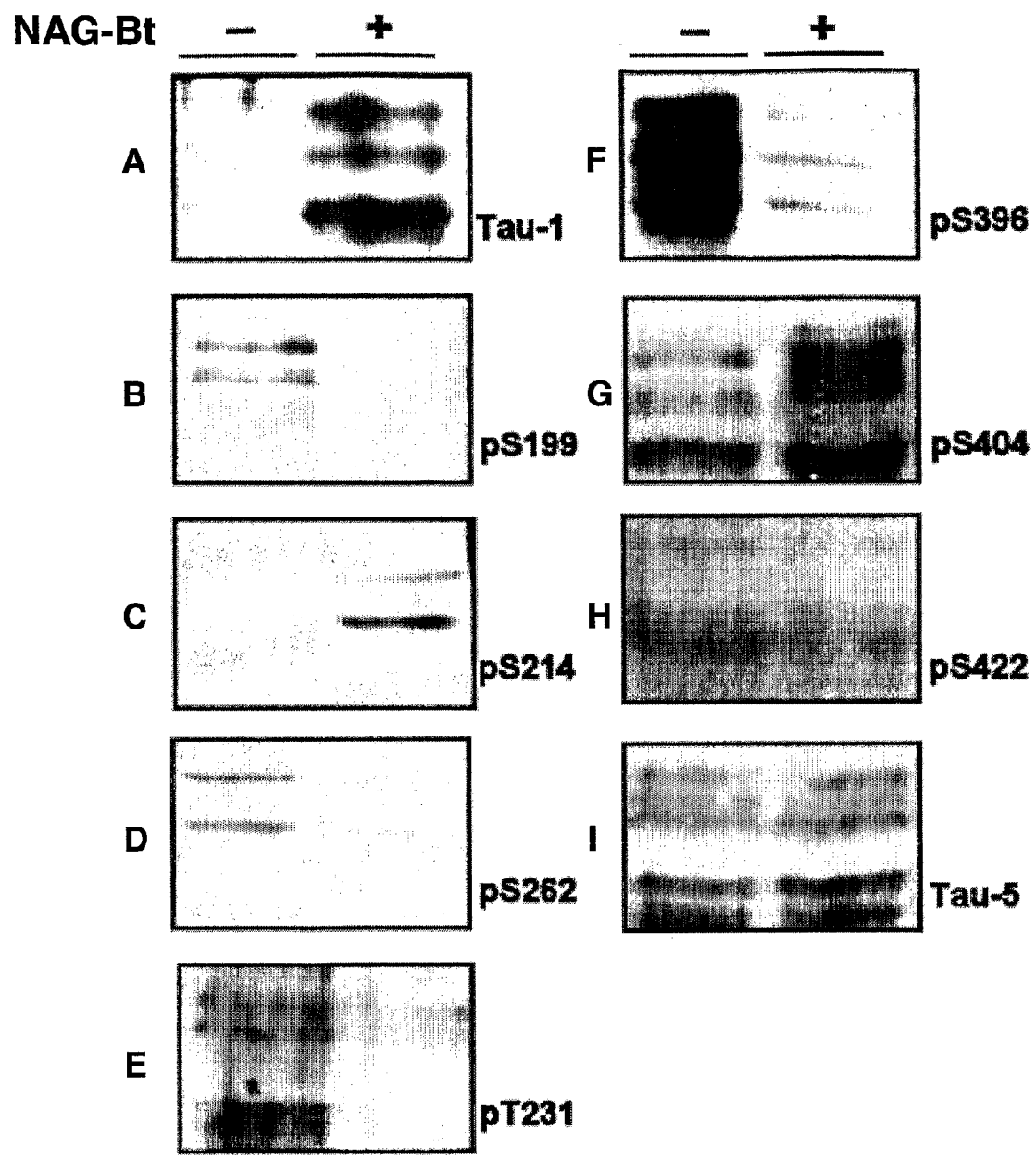
FIGS. 2A-I show Western blots of proteins from brain tissue of rats treated with or without NAG-Bt showing changes in brain tau phosphorylation at multiple sites following treatment. Equal amounts of homogenized brain tissue from an animal treated with and without NAG-Bt were separated by SDS-PAGE followed by probing with each of the primary antibodies, as indicated, and an appropriate secondary antibody (either an anti-mouse or anti-rabbit IGG-HRP conjugate, as appropriate). The lanes labeled "+" indicate samples Thom animals receiving NAG-Bt, while lanes labeled "−" indicate samples from animals receiving vehicle alone.

The invention provides, in part, novel compounds that are capable of inhibiting an O-glycoprotein 2-acetamido-2-deoxy-β-D-glucopyranosidase (O-GlcNAcase). In some embodiments, the O-GlcNAcase is a mammalian O-lcNAcase, such as a rat, mouse or human O-GlcNAcase. In some embodiments, the β-hexosaminidase is a mammalian β-hexosaminidase, such as a rat, mouse or human β-hexosaminidase.

In some embodiments, compounds according to the invention exhibit a surprising and unexpected selectivity in inhibiting an O-GlcNAcase. For example, when compared to the compounds described in Table 3 herein, the compounds according to the invention are surprisingly effective inhibitors of an O-GlcNAcase. In some embodiments, the compounds according to the invention are surprisingly more selective for an O-GlcNAcase over a β-hexosaminidase. In some embodiments, the compounds selectively inhibit the activity of a mammalian O-GlcNAcase over a mammalian β-hexosaminidase. In some embodiments, a selective inhibitor of an O-GlcNAcase does not substantially inhibit a β-hexosaminidase. A compound that "selectively" inhibits an O-GlcNAcase is a compound that inhibits the activity or biological function of an O-GlcNAcase, but does not substantially inhibit the activity or biological function of a β-hexosaminidase. For example, in some embodiments, a selective inhibitor of an O-GlcNAcase selectively inhibits the cleavage of 2-acetamido-2-deoxy-β-D-glucopyranoside (O-GlcNAc) from polypeptides. In some embodiments, a selective inhibitor of an O-GlcNAcase selectively binds to an O-GlcNAcase. In some embodiments, a selective inhibitor of an O-GlcNAcase inhibits hyperphosphorylation of a tau protein and/or inhibits formations of NFTs. By "inhibits," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase elevates or enhances O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, S-fold, 10-fold, 15-fold, 25-fold, 50-fold, 100-fold or more. In some embodiments, a selective inhibitor of an O-GlcNAcase exhibits a selectivity ratio, as described herein, in the range 100 to 100000, or in the range 1000 to 100000, or at least 100, 200, 500, 1000, 1500, 2000, 2500, 3000, 3500, 4000, 4500, 5000, 6000, 7000, 10,000, 25,000, 50,000, 75,000, or any value within or about the described range.

The compounds of the present invention elevate O-GlcNAc levels on O-GlcNAc-modified polypeptides or proteins in vivo specifically via interaction with an O-GlcNAcase enzyme, and are effective in treating conditions which require or respond to inhibition of O-GlcNAcase activity.

In some embodiments, the compounds of the present invention are useful as agents that produce a decrease in tau phosphorylation and NFT formation. In some embodiments, the compounds are therefore useful to treat Alzheimer's disease and related tauopathies. In some embodiments, the compounds are thus capable of treating Alzheimer's disease and related tauopathies by lowering tau phosphorylation and reducing NFT formation as a result of increasing tau O-GlcNAc levels. In some embodiments, the compounds produce an increase in levels of O-GlcNAc modification on O-GlcNAc-modified polypeptides or proteins, and are therefore useful for treatment of disorders responsive to such increases in O-GlcNAc modification; these disorders include without limitation neurodegenerative, inflammatory, cardiovascular, and immunoregulatory diseases. In some embodiments, the compounds are also useful as a result of other biological activities related to their ability to inhibit the activity of glycosidase enzymes. In alternative embodiments, the compounds of the invention are valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

In specific embodiments, the invention provides compounds described generally by Formula (I) and the salts, prodrugs, and stereoisomeric forms thereof:

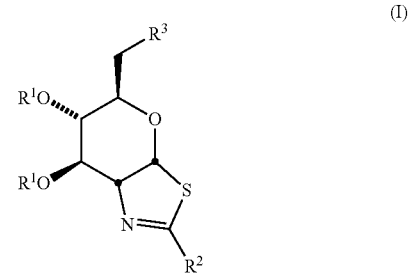

(I)

As set forth in Formula (I): each $R^1$ can be independently a non-interfering substituent; $R^2$ can be alkyl, aryl, heteroaryl, $OR^4$, $NR^4_2$, or $NR^4OR^4$, each of which may be optionally substituted with a non-interfering substituent, and where each $R^4$ may be independently a non-interfering substituent; $R^3$ can be $OR^4$, $N_3$, or $NR^4_2$, where each $R^4$ may be independently a non-interfering substituent. In some embodiments, each $R^1$ may be connected to form an additional ring structure. In alternative embodiments, when $R^3$ is $OR^4$, the $OR^4$ group may be connected to either $R^1$ to form an additional ring structure.

In the above Formula (I), each optionally substituted moiety may be substituted with one or more non-interfering substituents. For example, each optionally substituted moiety may be substituted with one or more inorganic substituents; phosphoryl; halo; =O; =$NR^5$; OR; $C_{1-10}$ alkyl or $C_{2-10}$ alkenyl optionally containing one or more P, N, O, or S, and optionally substituted with halo; CN; optionally substituted carbonyl; $NR^5_2$; C=$NR^5$; an optionally substituted carbocyclic or heterocyclic ring; or an optionally substituted aryl or heteroaryl. $R^5$ may be alkyl, branched alkyl, cycloalkyl, aryl, or heteroaryl.

In some embodiments, $R^1$ as set forth in Formula (I), may be either hydrogen or a substituent that includes 1-20 atoms that are other than hydrogen. In some embodiments, $R^1$ may be H, alkyl, or $C(O)R^5$, where $R^5$ may be alkyl, branched alkyl, cycloalkyl, aryl, or heteroaryl. In some embodiments, $R^1$ may be H or $C(O)CH_3$.

In some embodiments, $R^2$ as set forth in Formula (I), may be optionally substituted alkyl, OR, $NR_2$, or $NR^6OR^6$, where $R^6$ may be H, alkyl, branched alkyl, cycloalkyl, aryl, or heteroaryl. In some embodiments, $R^2$ may be $CH_2F$, $CHF_2$, $CF_3$, $(CH_2)_2CH=CH_2$, $(CH_2)_2CH=CHCH_3$, $CH_2OCH_3$, $(CH_2)_2CF_3$, cyclopropylmethyl, phenyl, benzyl, $NH_2$, $NHCH_3$, $NHCH_2CH_3$, $NH(CH_2)_2CH_3$, $NH(CH_2)_3CH_3$, $NHCH_2CH=CH_2$, NHcyclopropyl, $NHCH_2CH_2F$, $NHCH_2CHF_2$, $NHCH_2CF_3$, $NHCH_2CH_2OH$, $NHCH_2CH_2OC(O)CH_3$, $N(CH_3)_2$, $N(CH_3)(CH_2CH_3)$, $NHOCH_3$, $OCH_3$, or $(CH_2)_2CH_3$.

In some embodiments, $R^3$ as set forth in Formula (I), may be OR, $N_3$, or $NR^7_2$, where $R^7$ may be H, alkyl, branched alkyl, cycloalkyl, aryl, or heteroaryl. In some embodiments, $R^3$ may be OH, $OC(O)CH_3$, $N_3$, or $NH_2$.

In specific embodiments of the invention, compounds according to Formula (I) include one or more of the compounds described in Table 1.

TABLE 1

| Compound | Name | Structure |
|---|---|---|
| 1 | (3aR,5R,6S,7R,7aR)-5-(acetoxymethyl)-2-(fluoromethyl)-5,6,7,7a-tetrahydro-3aH-pyrano[3,2-d]thiazole-6,7-diyl diacetate | 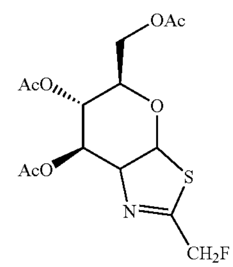 |
| 2 | (3aR,5R,6S,7R,7aR)-2-(fluoromethyl)-5-(hydroxymethyl)-5,6,7,7a-tetrahydro-3aH-pyrano[3,2-d]thiazole-6,7-diol | 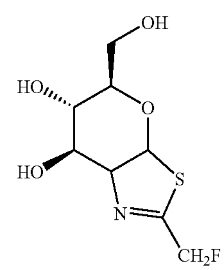 |
| 3 | (3aR,5R,6S,7R,7aR)-5-(acetoxymethyl)-2-(difluoromethyl)-5,6,7,7a-tetrahydro-3aH-pyrano[3,2-d]thiazole-6,7-diyl diacetate | 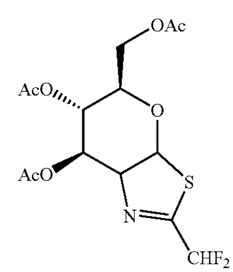 |

TABLE 1-continued

| Compound | Name | Structure |
|---|---|---|
| 4 | (3aR,5R,6S,7R,7aR)-2-(difluoromethyl)-5-(hydroxymethyl)-5,6,7,7a-tetrahydro-3aH-pyrano[3,2-d]thiazole-6,7-diol | 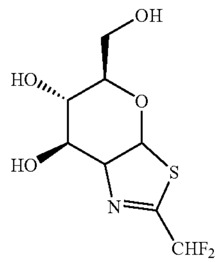 |
| 5 | (3aR,5R,6S,7R,7aR)-5-(acetoxymethyl)-2-(trifluoromethyl)-5,6,7,7a-tetrahydro-3aH-pyrano[3,2-d]thiazole-6,7-diyl diacetate | 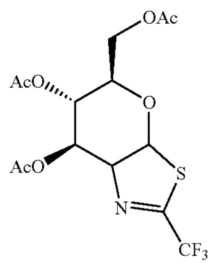 |
| 6 | (3aR,5R,6S,7R,7aR)-5-(hydroxymethyl)-2-(trifluoromethyl)-5,6,7,7a-tetrahydro-3aH-pyrano[3,2-d]thiazole-6,7-diol | 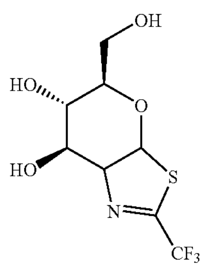 |
| 7 | (3aR,5R,6S,7R,7aR)-5-(acetoxymethyl)-2-(but-3-enyl)-5,6,7,7a-tetrahydro-3aH-pyrano[3,2-d]thiazole-6,7-diyl diacetate | 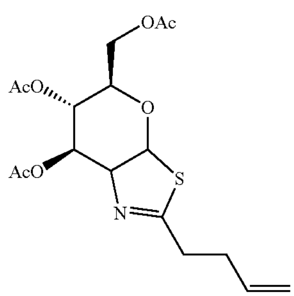 |
| 8 | (3aR,5R,6S,7R,7aR)-2-(but-3-enyl)-5-(hydroxymethyl)-5,6,7,7a-tetrahydro-3aH-pyrano[3,2-d]thiazole-6,7-diol | 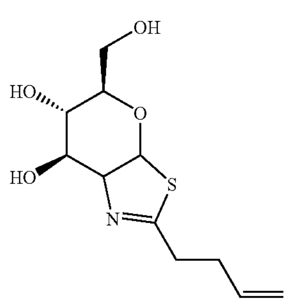 |

TABLE 1-continued

| Compound | Name | Structure |
|---|---|---|
| 9 | (3aR,5R,6S,7R,7aR)-5-(acetoxymethyl)-2-(E,Z)-(pent-3-enyl)-5,6,7,7a-tetrahydro-3aH-pyrano[3,2-d]thiazole-6,7-diyl diacetate | 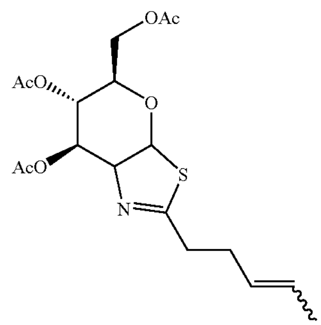 |
| 10 | (3aR,5R,6S,7R,7aR)-5-(hydroxymethyl)-2-(E,Z)-(pent-3-enyl)-5,6,7,7a-tetrahydro-3aH-pyrano[3,2-d]thiazole-6,7-diol | 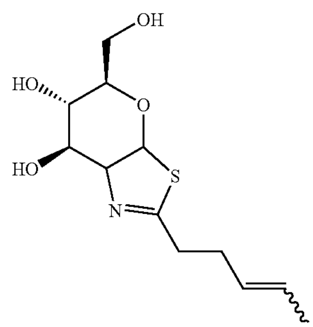 |
| 11 | (3aR,5R,6S,7R,7aR)-5-(acetoxymethyl)-2-(methoxymethyl)-5,6,7,7a-tetrahydro-3aH-pyrano[3,2-d]thiazole-6,7-diyl diacetate | 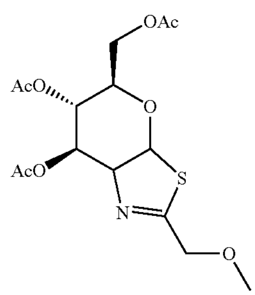 |
| 12 | (3aR,5R,6S,7R,7aR)-5-(hydroxymethyl)-2-(methoxymethyl)-5,6,7,7a-tetrahydro-3aH-pyrano[3,2-d]thiazole-6,7-diol | 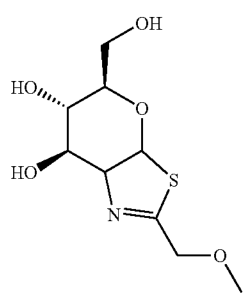 |
| 13 | (3aR,5R,6S,7R,7aR)-5-(acetoxymethyl)-2-(3,3,3-trifluoropropyl)-5,6,7,7a-tetrahydro-3aH-pyrano[3,2-d]thiazole-6,7-diyl diacetate | 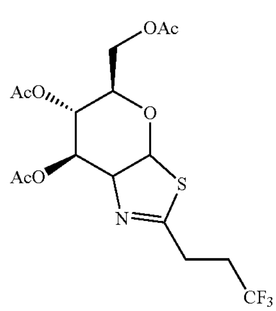 |

TABLE 1-continued

| Compound | Name | Structure |
|---|---|---|
| 14 | (3aR,5R,6S,7R,7aR)-5-(hydroxymethyl)-2-(3,3,3-trifluoropropyl)-5,6,7,7a-tetrahydro-3aH-pyrano[3,2-d]thiazole-6,7-diol | 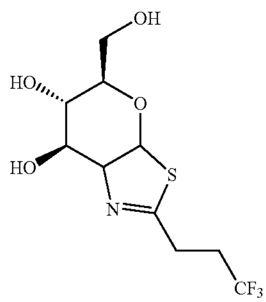 |
| 15 | (3aR,5R,6S,7R,7aR)-5-(acetoxymethyl)-2-(cyclopropylmethyl)-5,6,7,7a-tetrahydro-3aH-pyrano[3,2-d]thiazole-6,7-diyl diacetate | 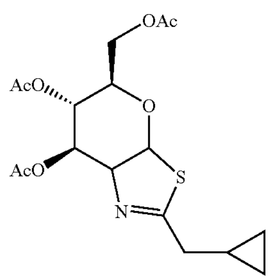 |
| 16 | (3aR,5R,6S,7R,7aR)-2-(cyclopropylmethyl)-5-(hydroxymethyl)-5,6,7,7a-tetrahydro-3aH-pyrano[3,2-d]thiazole-6,7-diol | 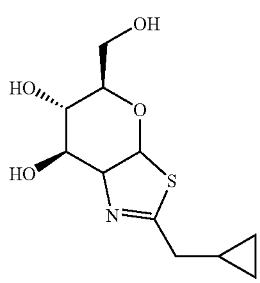 |
| 17 | (3aR,5R,6S,7R,7aR)-5-(acetoxymethyl)-2-phenyl-5,6,7,7a-tetrahydro-3aH-pyrano[3,2-d]thiazole-6,7-diyl diacetate | 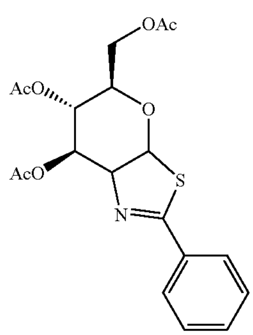 |
| 18 | (3aR,5R,6S,7R,7aR)-5-(hydroxymethyl)-2-phenyl-5,6,7,7a-tetrahydro-3aH-pyrano[3,2-d]thiazole-6,7-diol | 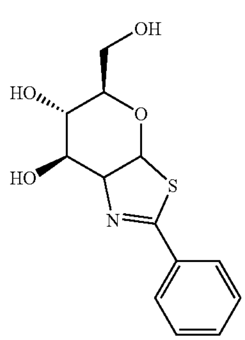 |

TABLE 1-continued

| Compound | Name | Structure |
|---|---|---|
| 19 | (3aR,5R,6S,7R,7aR)-5-(acetoxymethyl)-2-benzyl-5,6,7,7a-tetrahydro-3aH-pyrano[3,2-d]thiazole-6,7-diyl diacetate | 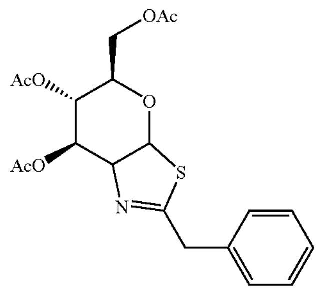 |
| 20 | (3aR,5R,6S,7R,7aR)-2-benzyl-5-(hydroxymethyl)-5,6,7,7a-tetrahydro-3aH-pyrano[3,2-d]thiazole-6,7-diol | 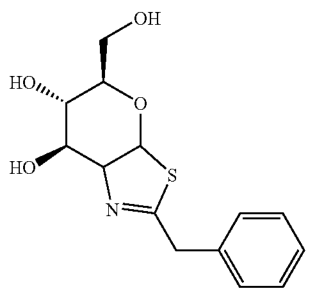 |
| 21 | (3aR,5R,6S,7R,7aR)-2-amino-5-(hydroxymethyl)-5,6,7,7a-tetrahydro-3aH-pyrano[3,2-d]thiazole-6,7-diol | 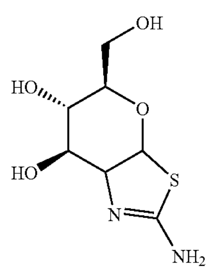 |
| 23 | (3aR,5R,6S,7R,7aR)-5-(hydroxymethyl)-2-(methylamino)-5,6,7,7a-tetrahydro-3aH-pyrano[3,2-d]thiazole-6,7-diol | 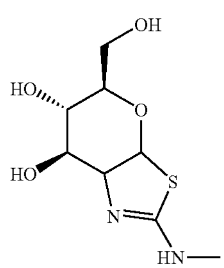 |
| 24 | (3aR,5R,6S,7R,7aR)-5-(acetoxymethyl)-2-(ethylamino)-5,6,7,7a-tetrahydro-3aH-pyrano[3,2-d]thiazole-6,7-diyl diacetate | 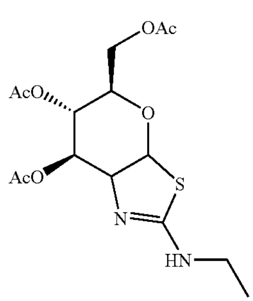 |

TABLE 1-continued

| Compound | Name | Structure |
|---|---|---|
| 25 | (3aR,5R,6S,7R,7aR)-2-(ethylamino)-5-(hydroxymethyl)-5,6,7,7a-tetrahydro-3aH-pyrano[3,2-d]thiazole-6,7-diol | 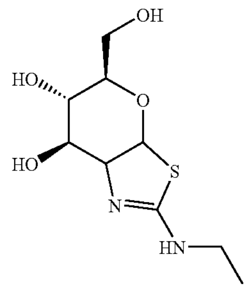 |
| 27 | (3aR,5R,6S,7R,7aR)-5-(hydroxymethyl)-2-(propylamino)-5,6,7,7a-tetrahydro-3aH-pyrano[3,2-d]thiazole-6,7-diol | 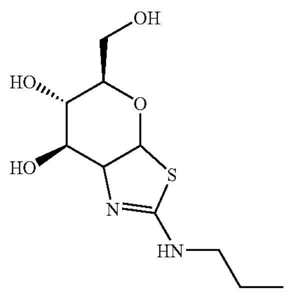 |
| 29 | (3aR,5R,6S,7R,7aR)-2-(butylamino)-5-(hydroxymethyl)-5,6,7,7a-tetrahydro-3aH-pyrano[3,2-d]thaizole-6,7-diol | 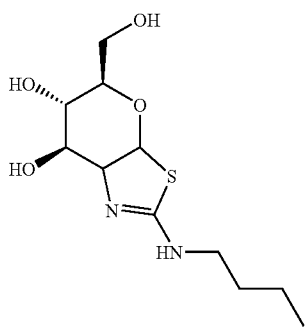 |
| 30 | (3aR,5R,6S,7R,7aR)-5-(acetoxymethyl)-2-(allylamino)-5,6,7,7a-tetrahydro-3aH-pyrano[3,2-d]thiazole-6,7-diyl diacetate | 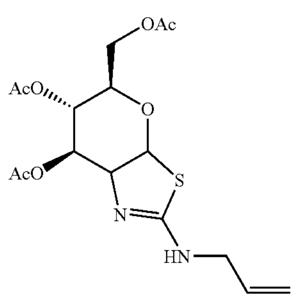 |
| 31 | (3aR,5R,6S,7R,7aR)-2-(allylamino)-5-(hydroxymethyl)-5,6,7,7a-tetrahydro-3aH-pyrano[3,2-d]thiazole-6,7-diol | 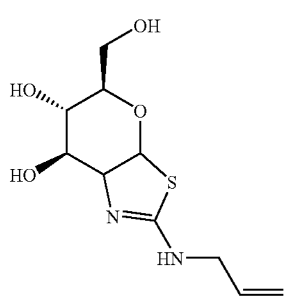 |

TABLE 1-continued

| Compound | Name | Structure |
|---|---|---|
| 32 | (3aR,5R,6S,7R,7aR)-5-(acetoxymethyl)-2-(cyclopropylamino)-5,6,7,7a-tetrahydro-3aH-pyrano[3,2-d]thiazole-6,7-diyl diacetate | 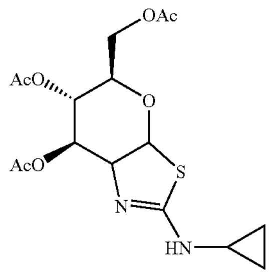 |
| 33 | (3aR,5R,6S,7R,7aR)-2-(cyclopropylamino)-5-(hydroxymethyl)-5,6,7,7a-tetrahydro-3aH-pyrano[3,2-d]thiazole-6,7-diol | 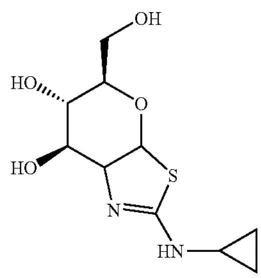 |
| 34 | (3aR,5R,6S,7R,7aR)-5-(acetoxymethyl)-2-(2-fluoroethylamino)-5,6,7,7a-tetrahydro-3aH-pyrano[3,2-d]thiazole-6,7-diyl diacetate | 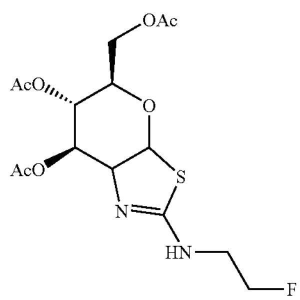 |
| 35 | (3aR,5R,6S,7R,7aR)-2-(2-fluoroethylamino)-5-(hydroxymethyl)-5,6,7,7a-tetrahydro-3aH-pyrano[3,2-d]thiazole-6,7-diol | 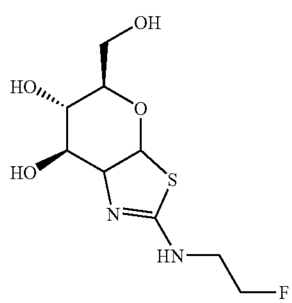 |
| 36 | (3aR,5R,6S,7R,7aR)-5-(acetoxymethyl)-2-(2,2-difluoroethylamino)-5,6,7,7a-tetrahydro-3aH-pyrano[3,2-d]thiazole-6,7-diyl diacetate | 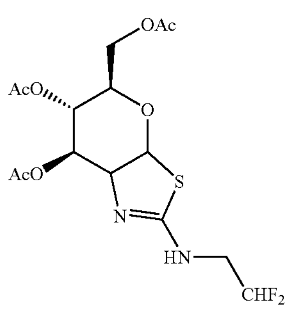 |

TABLE 1-continued

| Compound | Name | Structure |
|---|---|---|
| 37 | (3aR,5R,6S,7R,7aR)-2-(2,2-difluoroethylamino)-5-(hydroxymethyl)-5,6,7,7a-tetrahydro-3aH-pyrano[3,2-d]thiazole-6,7-diol | 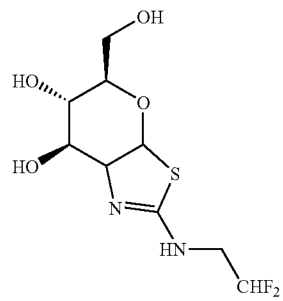 |
| 38 | (3aR,5R,6S,7R,7aR)-5-(acetoxymethyl)-2-(2,2,2-trifluoroethylamino)-5,6,7,7a-tetrahydro-3aH-pyrano[3,2-d]thiazole-6,7-diyl diacetate | 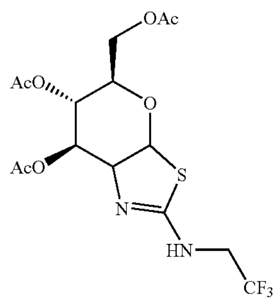 |
| 39 | (3aR,5R,6S,7R,7aR)-5-(hydroxymethyl)-2-(2,2,2-trifluoroethylamino)-5,6,7,7a-tetrahydro-3aH-pyrano[3,2-d]thiazole-6,7-diol | 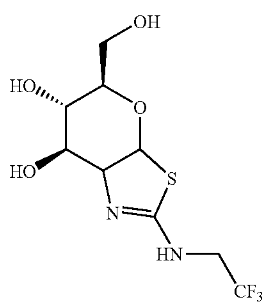 |
| 40 | (3aR,5R,6S,7R,7aR)-2-(2-acetoxyethylamino)-5-(acetoxymethyl)-5,6,7,7a-tetrahydro-3aH-pyrano[3,2-d]thiazole-6,7-diyl diacetate | 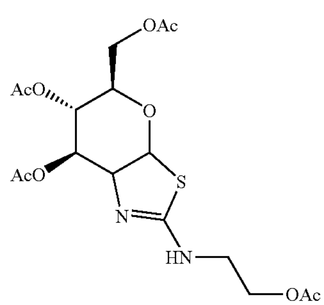 |
| 41 | (3aR,5R,6S,7R,7aR)-2-(2-hydroxyethylamino)-5-(hydroxymethyl)-5,6,7,7a-tetrahydro-3aH-pyrano[3,2-d]thiazole-6,7-diol | 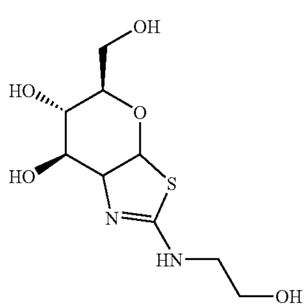 |

TABLE 1-continued

| Compound | Name | Structure |
|---|---|---|
| 44 | (3aR,5R,6S,7R,7aR)-5-(acetoxymethyl)-2-(ethyl(methyl)amino)-5,6,7,7a-tetrahydro-3aH-pyrano[3,2-d]thiazole-6,7-diyl diacetate | 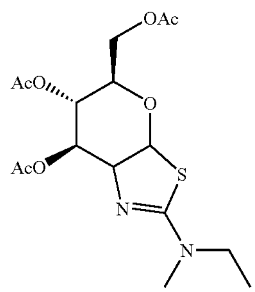 |
| 45 | (3aR,5R,6S,7R,7aR)-2-(ethyl(methyl)amino)-5-(hydroxymethyl)-5,6,7,7a-tetrahydro-3aH-pyrano[3,2-d]thiazole-6,7-diol | 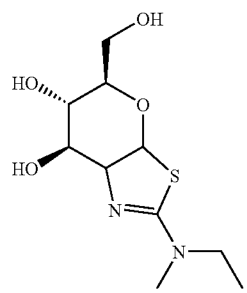 |
| 46 | (3aR,5R,6S,7R,7aR)-5-(acetoxymethyl)-2-(methoxyamino)-5,6,7,7a-tetrahydro-3aH-pyrano[3,2-d]thiazole-6,7-diyl diacetate | 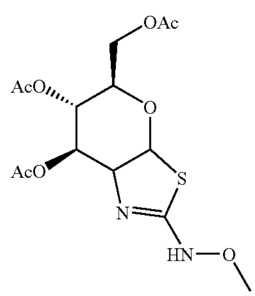 |
| 47 | (3aR,5R,6S,7R,7aR)-5-(hydroxymethyl)-2-(methoxyamino)-5,6,7,7a-tetrahydro-3aH-pyrano[3,2-d]thiazole-6,7-diol | 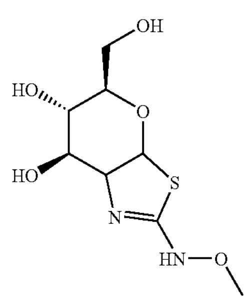 |
| 48 | (3aR,5R,6S,7R,7aR)-5-(acetoxymethyl)-2-methoxy-5,6,7,7a-tetrahydro-3aH-pyrano[3,2-d]thiazole-6,7-diyl diacetate | 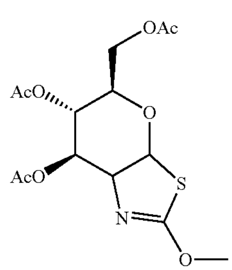 |

TABLE 1-continued

| Compound | Name | Structure |
|---|---|---|
| 49 | (3aR,5R,6S,7R,7aR)-5-(hydroxymethyl)-2-methoxy-5,6,7,7a-tetrahydro-3aH-pyrano[3,2-d]thiazole-6,7-diol | 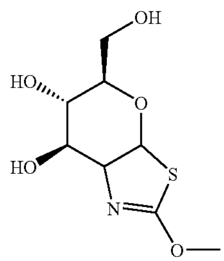 |
| 50 | (3aR,5R,6S,7R,7aR)-5-(azidomethyl)-2-propyl-5,6,7,7a-tetrahydro-3aH-pyrano[3,2-d]thiazole-6,7-diol | 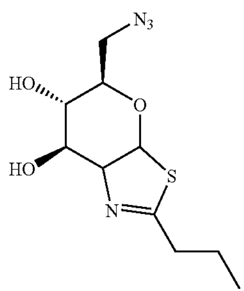 |
| 51 | (3aR,5R,6S,7R,7aR)-5-(aminomethyl)-2-propyl-5,6,7,7a-tetrahydro-3aH-pyrano[3,2-d]thiazole-6,7-diol | 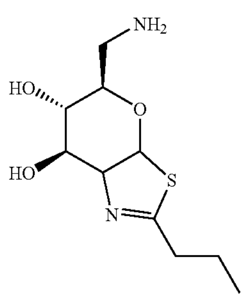 |

In alternative embodiments of the invention, compounds according to Formula (I) include one or more of the compounds described in Table 2.

TABLE 2

| Compound | Name | Structure |
|---|---|---|
| 22 | (3aR,5R,6S,7R,7aR)-5-(acetoxymethyl)-2-(methylamino)-5,6,7,7a-tetrahydro-3aH-pyrano[3,2-d]thiazole-6,7-diyl diacetate | 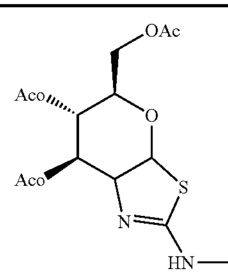 |

TABLE 2-continued

| Compound | Name | Structure |
|---|---|---|
| 26 | (3aR,5R,6S,7R,7aR)-5-(acetoxymethyl)-2-(propylamino)-5,6,7,7a-tetrahydro-3aH-pyrano[3,2-d]thiazole-6,7-diyl diacetate | 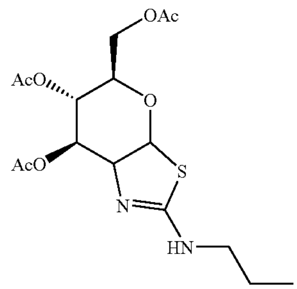 |
| 28 | (3aR,5R,6S,7R,7aR)-5-(acetoxymethyl)-2-(butylamino)-5,6,7,7a-tetrahydro-3aH-pyrano[3,2-d]thiazole-6,7-diyl diacetate | 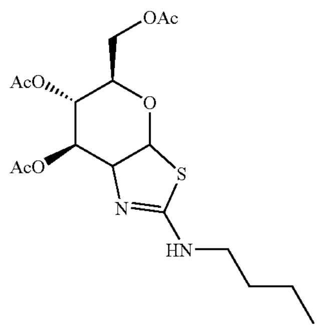 |
| 42 | (3aR,5R,6S,7R,7aR)-5-(acetoxymethyl)-2-(dimethylamino)-5,6,7,7a-tetrahydro-3aH-pyrano[3,2-d]thiazole-6,7-diyl diacetate | 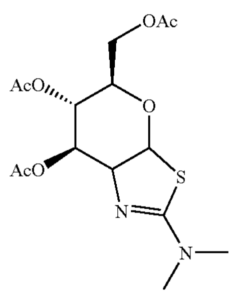 |
| 43 | (3aR,5R,6S,7R,7aR)-2-(dimethylamino)-5-(hydroxymethyl)-5,6,7,7a-tetrahydro-3aH-pyrano[3,2-d]thiazole-6,7-diol | 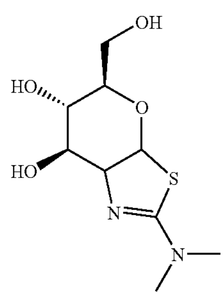 |
| 52 | (3aR,5R,6R,7R,7aR)-5-(hydroxymethyl)-2-methyl-5,6,7,7a-tetrahydro-3aH-pyrano[3,2-d]thiazole-6,7-diol | 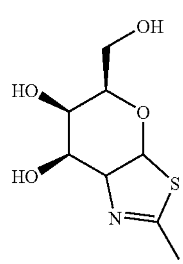 |

TABLE 2-continued

| Compound | Name | Structure |
|---|---|---|
| 53 | (3aR,5R,6R,7R,7aR)-5-(acetoxymethyl)-2-methyl-5,6,7,7a-tetrahydro-3aH-pyrano[3,2-d]thiazole-6,7-diyl diacetate | 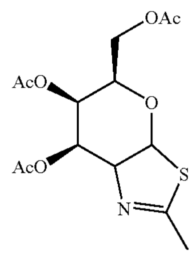 |
| 54 | (3aR,5R,6S,7R,7aR)-5-(hydroxymethyl)-2-methyl-5,6,7,7a-tetrahydro-3aH-pyrano[3,2-d]thiazole-6,7-diol | 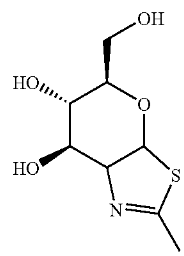 |
| 55 | (3aR,5R,6S,7R,7aR)-5-(acetoxymethyl)-2-methyl-5,6,7,7a-tetrahydro-3aH-pyrano[3,2-d]thiazole-6,7-diyl diacetate | 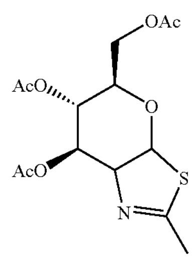 |
| 56 | (3aR,5R,6S,7R,7aR)-2-heptyl-5-(hydroxymethyl)-5,6,7,7a-tetrahydro-3aH-pyrano[3,2-d]thiazole-6,7-diol | 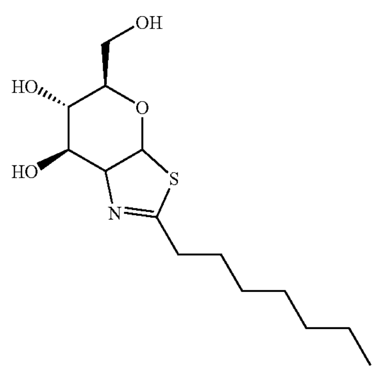 |
| 57 | (3aR,5R,6S,7R,7aR)-5-(acetoxymethyl)-2-heptyl-5,6,7,7a-tetrahydro-3aH-pyrano[3,2-d]thiazole-6,7-diyl diacetate | 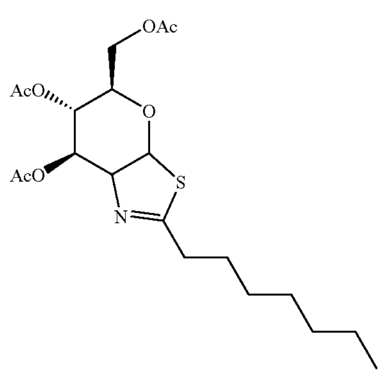 |

TABLE 2-continued

| Compound | Name | Structure |
|---|---|---|
| 58 | (3aR,5R,6S,7R,7aR)-5-(acetoxymethyl)-2-(bromomethyl)-5,6,7,7a-tetrahydro-3aH-pyrano[3,2-d]thiazole-6,7-diyl diacetate | 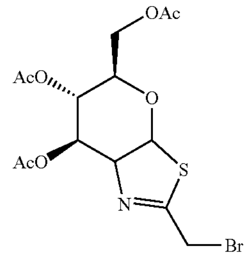 |
| 59 | (3aR,5R,6S,7R,7aR)-5-(acetoxymethyl)-2-(dibromomethyl)-5,6,7,7a-tetrahydro-3aH-pyrano[3,2-d]thiazole-6,7-diyl diacetate | 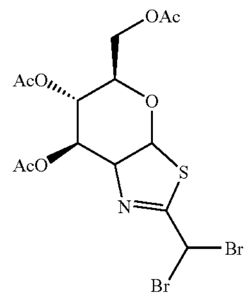 |
| 60 | methyl hydrogen 2-((3aR,5R,6S,7R,7aR)-6,7-dihydroxy-5-(hydroxymethyl)-5,6,7,7a-tetrahydro-3aH-pyrano[3,2-d]thiazol-2-yl)ethylphosphonate | 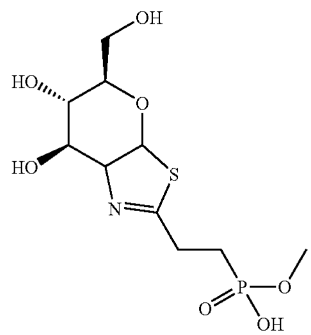 |
| 61 | (3aR,5R,6S,7R,7aR)-5-(acetoxymethyl)-2-(2-(hydroxy(methoxy)phosphoryl)ethyl)-5,6,7,7a-tetrahydro-3aH-pyrano[3,2-d]thiazole-6,7-diyl diacetate | 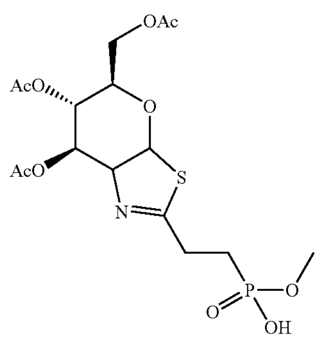 |
| 62 | (3aR,5R,6S,7R,7aR)-5-(acetoxymethyl)-2-(2-(dimethoxyphosphoryl)ethyl)-5,6,7,7a-tetrahydro-3aH-pyrano[3,2-d]thiazole-6,7-diyl diacetate | 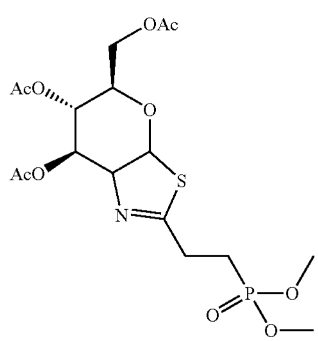 |

TABLE 2-continued

| Compound | Name | Structure |
|---|---|---|
| 63 | (3aR,5R,6S,7R,7aR)-5-(acetoxymethyl)-2-((diethoxyphosphoryl)methyl)-5,6,7,7a-tetrahydro-3aH-pyrano[3,2-d]thiazole-6,7-diyl diacetate | 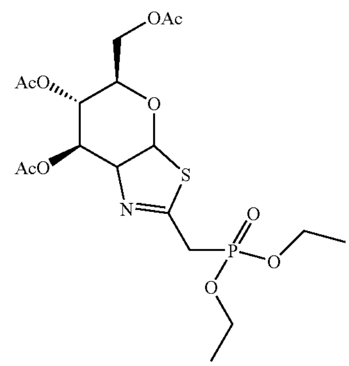 |
| 64 | octyl hydrogen-2-((3aR,5R,6S,7R,7aR)-6,7-dihydroxy-5-(hydroxymethyl)-5,6,7,7a-tetrahydro-3aH-pyrano[3,2-d]thiazol-2-yl)ethylphosphonate | 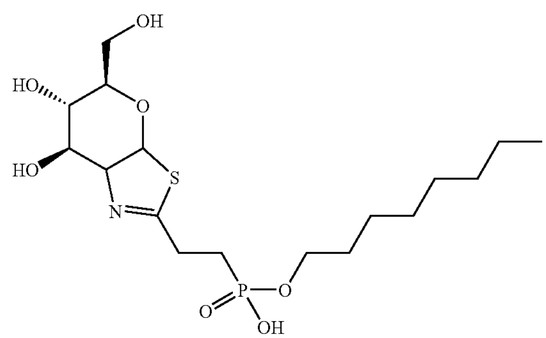 |
| 65 | (3aR,5R,6S,7R,7aR)-5-(acetoxymethyl)-2-(2-(hydroxy(octyloxy)phosphoryl)ethyl)-5,6,7,7a-tetrahydro-3aH-pyrano[3,2-d]thiazole-6,7-diyl diacetate | 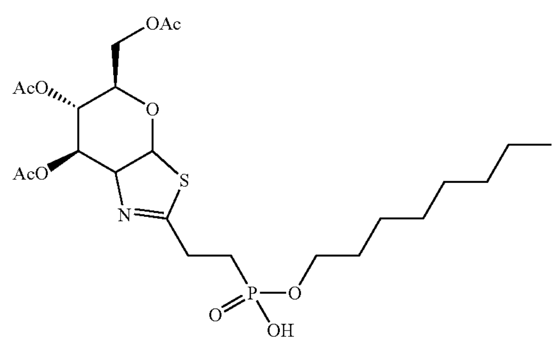 |
| 66 | (3aR,5R,6S,7R,7aR)-5-(acetoxymethyl)-2-(2-(methoxy(octyloxy)phosphoryl)ethyl)-5,6,7,7a-tetrahydro-3aH-pyrano[3,2-d]thiazole-6,7-diyl diacetate | 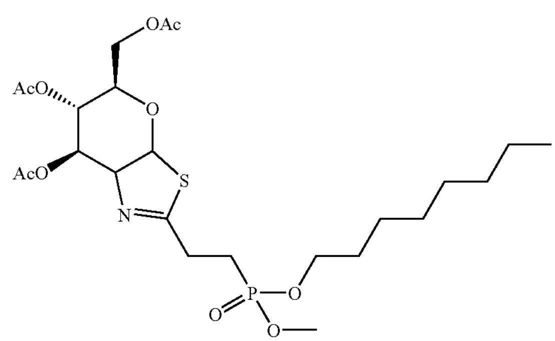 |

TABLE 2-continued

| Compound | Name | Structure |
|---|---|---|
| 67 | (3aR,5R,6S,7R,7aR)-5-(acetoxymethyl)-2-(isopropylamino)-5,6,7,7a-tetrahydro-3aH-pyrano[3,2-d]thiazole-6,7-diyl diacetate | 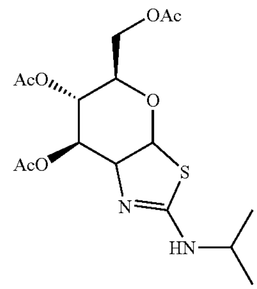 |
| 68 | (3aR,5R,6S,7R,7aR)-5-(acetoxymethyl)-2-(cyclohexylamino)-5,6,7,7a-tetrahydro-3aH-pyrano[3,2-d]thiazole-6,7-diyl diacetate | 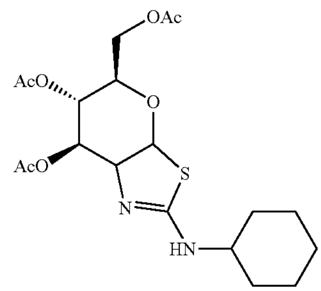 |
| 69 | (3aR,5R,6S,7R,7aR)-5-(acetoxymethyl)-2-(benzylamino)-5,6,7,7a-tetrahydro-3aH-pyrano[3,2-d]thiazole-6,7-diyl diacetate | 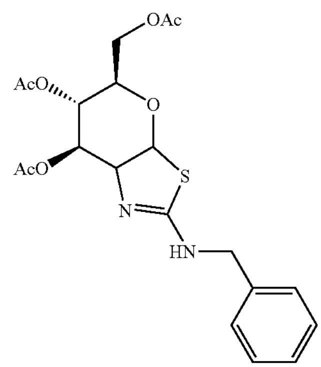 |
| 70 | (3aR,5R,6S,7R,7aR)-5-(hydroxymethyl)-2-(phenylamino)-5,6,7,7a-tetrahydro-3aH-pyrano[3,2-d]thiazole-6,7-diol | 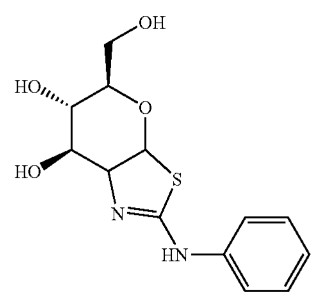 |
| 71 | (3aR,5R,6S,7R,7aR)-5-(acetoxymethyl)-2-(phenylamino)-5,6,7,7a-tetrahydro-3aH-pyrano[3,2-d]thiazole-6,7-diyl diacetate | 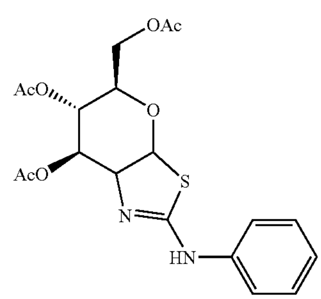 |

TABLE 2-continued

| Compound | Name | Structure |
|---|---|---|
| 72 | (3aR,5R,6S,7R,7aR)-5-(hydroxymethyl)-2-(4-methoxyphenylamino)-5,6,7,7a-tetrahydro-3aH-pyrano[3,2-d]thiazole-6,7-diol | 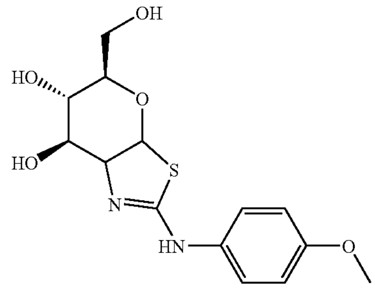 |
| 73 | (3aR,5R,6S,7R,7aR)-5-(acetoxymethyl)-2-(4-methoxyphenylamino)-5,6,7,7a-tetrahydro-3aH-pyrano[3,2d]thiazole-6,7-diyl diazetate | 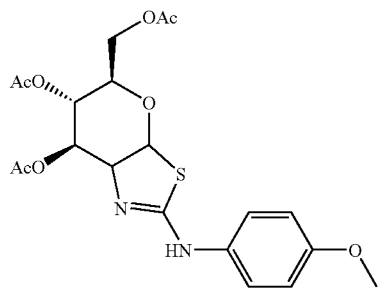 |
| 74 | (3aR,5R,6S,7R,7aR)-5-(acetoxymethyl)-2-(N-phenylacetamido)-5,6,7,7a-tetrahydro-3aH-pyrano[3,2-d]thiazole-6,7-diyl diacetate | 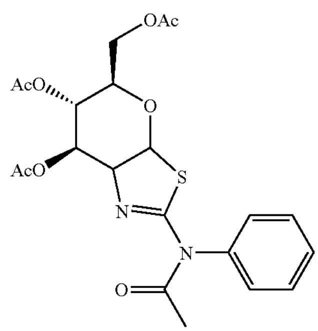 |
| 75 | (3aR,5R,6S,7R,7aR)-5-(acetoxymethyl)-2-(N-(4-methxoyphenyl)acetamido)-5,6,7,7a-tetrahydro-3aH-pyrano[3,2-d]thiazole-6,7-diyl diacetate | 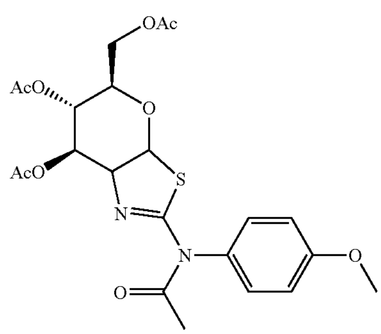 |
| 76 | ((3aR,5R,6S,7R,7aR)-6,7-dihydroxy-2-methyl-5,6,7,7a-tetrahydro-3aH-pyrano[3,2-d]thiazol-5-yl)methyl hydrogen sulfate | 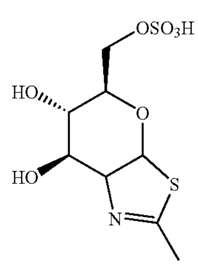 |

TABLE 2-continued

| Compound | Name | Structure |
|---|---|---|
| 77 | (3aR,5R,6S,7R,7aR)-6,7-bis(benzyloxy)-5-(benzyloxymethyl)-2-methyl-5,6,7,7a-tetrahydro-3aH-pyrano[3,2-d]thiazole | 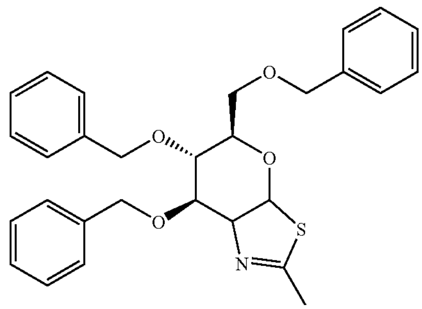 |
| 78 | (2R)-2-[[(3aR,4aR,7R,8aS,9R,9aR)-3a,4a,5,8a,9,9a-hexahydro-7-[(4-methoxyphenyl)methyl]-2-methyl[1,3]dioxino[4',5':5,6]pyrano[3,2-d]thiazol-9-yl]oxy]-propanoic acid | 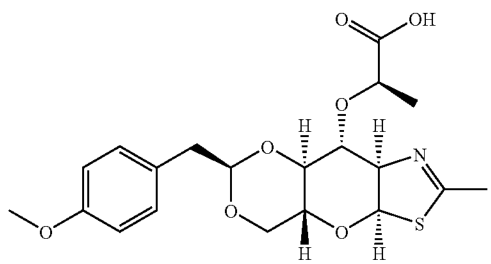 |
| 79 | N-[(2R)-2-[[(3aR,4aR,7R,8aS,9R,9aR)-3a,4a,5,8a,9,9a-hexahydro-7-[(4-methoxyphenyl)methyl]-2-methyl[1,3]dioxino[4',5':5,6]pyrano[3,2-d]thiazol-9-yl]oxy]-1-oxopropyl]-L-alanyl-D-Glutamic acid | 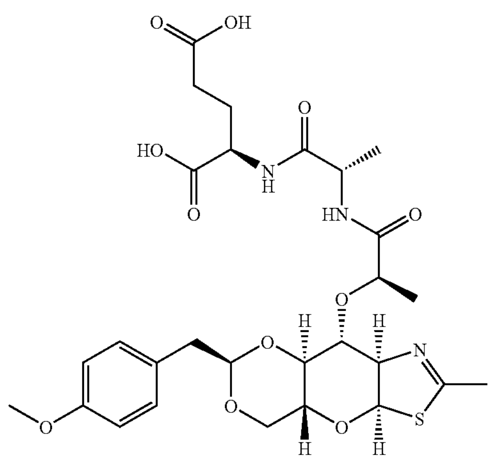 |
| 80 | N-[(2R)-1-oxo-2-[[(3aR,5R,6S,7R,7aR)-3a,6,7,7a-tetrahydro-6-hydroxy-5-(hydroxymethyl)-2-methyl-5H-pyrano[3,2-d]thiazol-7-yl]oxy]propyl]-L-alanyl-D-Glutamic acid | 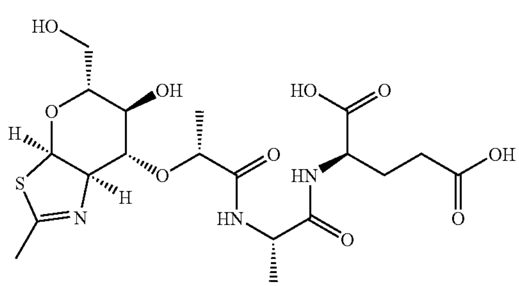 |

TABLE 2-continued

| Compound | Name | Structure |
|---|---|---|
| 81 | (2R)-2-[[(3aR,4aR,7R,8aS,9R,9aR)-2-heptyl-3a,4a,5,8a,9,9a-hexahydro-7-[(4-methoxyphenyl)methyl][1,3]dioxino[4',5':5,6]pyrano[3,2-d]thiazol-9-yl]oxy]-Propanoic acid | 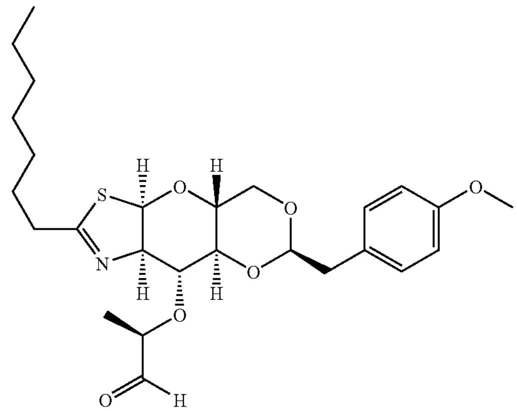 |
| 82 | N-[(2R)-2-[[(3aR,4aR,7R,8aS,9R,9aR)-2-heptyl-3a,4a,5,8a,9,9a-hexahydro-7-[(4-methoxyphenyl)methyl][1,3]dioxino[4',5':5,6]pyrano[3,2-d]thiazol-9-yl]oxy]-1-oxopropyl]-L-alanyl-D-Glutamic acid | 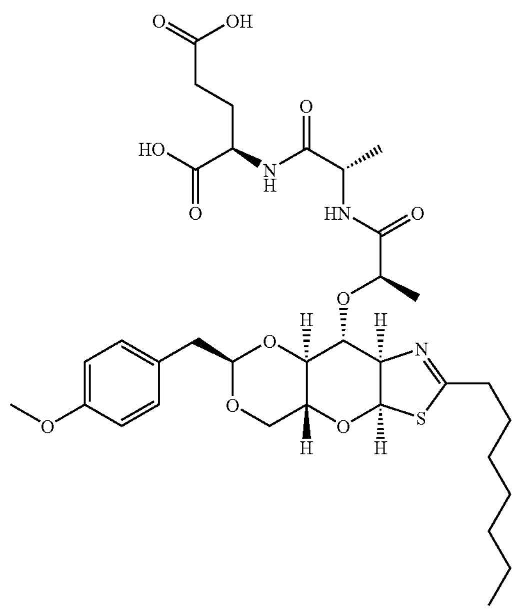 |
| 83 | N-[(2R)-2-[[(3aR,5R,6S,7R,7aR)-2-heptyl-3a,6,7,7a-tetrahydro-6-hydroxy-5-(hydroxymethyl)-5H-pyrano[3,2-d]thiazol-7-yl]oxy]-1-oxopropyl]-L-alanyl-D-Glutamic acid | 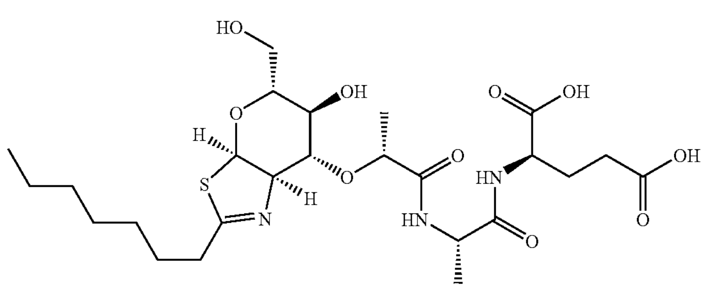 |

TABLE 2-continued

| Compound | Name | Structure |
|---|---|---|
| 84 | N-acetyl-2-O-[[(3aR,5R,6R,7R,7aR)-6,7-bis(acetyloxy)-3a,6,7,7a-tetrahydro-2-methyl-5H-pyrano[3,2-d]thiazol-5-yl]methyl]-α-Neuraminic acid, 4,7,8,9-tetraacetate | 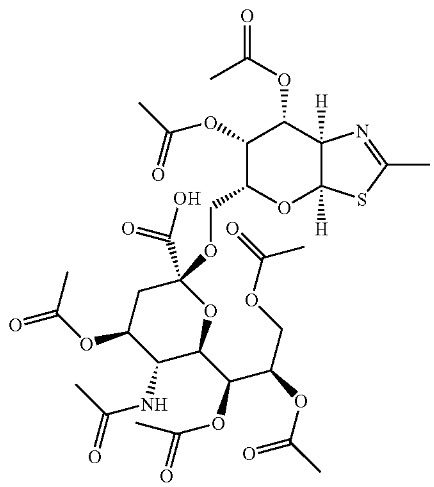 |
| 85 | N-acetyl-2-O-[[(3aR,5R,6R,7R,7aR)-6-(acetyloxy)-3a,6,7,7a-tetrahydro-2-methyl-7-[(2,3,4,6-tetra-O-acetyl-β-D-galactopyranosyl)oxy]-5H-pyrano[3,2-d]thiazol-5-yl]methyl]-α-Neuraminic acid, 4,7,8,9-tetraacetate | 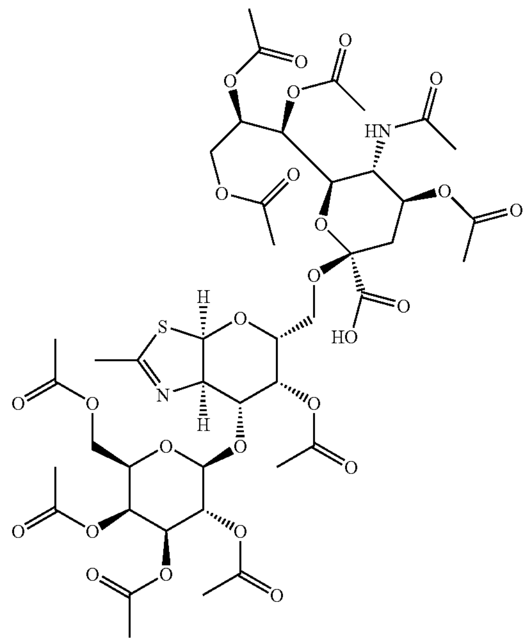 |

In alternative embodiments of the invention, compounds according to Formula (I) include one or more of the compounds described in Table 3.

TABLE 3

| Compound | Name | Structure |
|---|---|---|
| 86 | (3aR,5R,6S,7R,7aR)-2-ethyl-5-(hydroxymethyl)-5,6,7,7a-tetrahydro-3aH-pyrano[3,2-d]thiazole-6,7-diol | 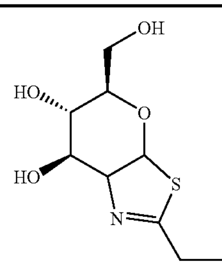 |

TABLE 3-continued

| Compound | Name | Structure |
|---|---|---|
| 87 | (3aR,5R,6S,7R,7aR)-5-(hydroxymethyl)-2-propyl-5,6,7,7a-tetrahydro-3aH-pyrano[3,2-d]thiazole-6,7-diol | 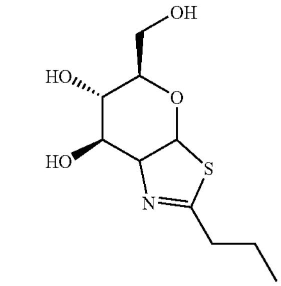 |
| 88 | (3aR,5R,6S,7R,7aR)-2-butyl-5-(hydroxymethyl)-5,6,7,7a-tetrahydro-3aH-pyrano[3,2-d]thiazole-6,7-diol | 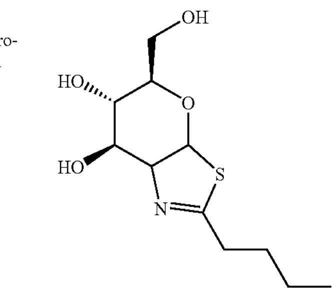 |
| 89 | (3aR,5R,6S,7R,7aR)-5-(hydroxymethyl)-2-pentyl-5,6,7,7a-tetrahydro-3aH-pyrano[3,2-d]thiazole-6,7-diol | 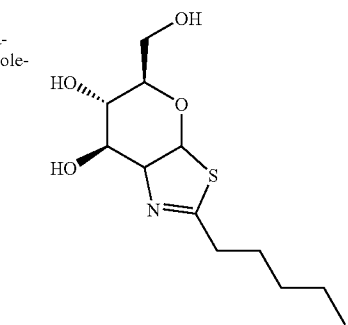 |
| 90 | (3aR,5R,6S,7R,7aR)-5-(hydroxymethyl)-2-isopropyl-5,6,7,7a-tetrahydro-3aH-pyrano[3,2-d]thiazole-6,7-diol | 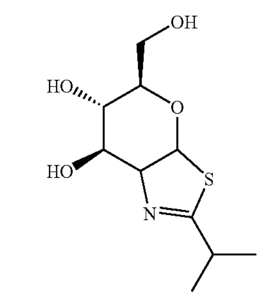 |
| 91 | (3aR,5R,6S,7R,7aR)-5-(hydroxymethyl)-2-isobutyl-5,6,7,7a-tetrahydro-3aH-pyrano[3,2-d]thiazole-6,7-diol | 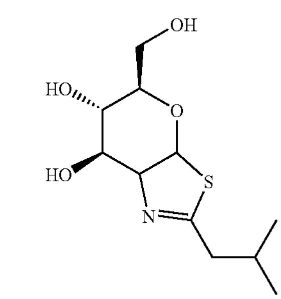 |

TABLE 3-continued

| Compound | Name | Structure |
|---|---|---|
| 92 | (3aR,5R,6S,7R,7aR)-5-(acetoxymethyl)-2-ethyl-5,6,7,7a-tetrahydro-3aH-pyrano[3,2-d]thiazole-6,7-diyl diacetate | 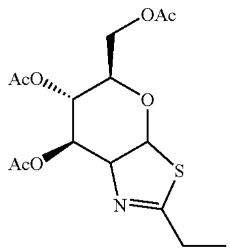 |
| 93 | (3aR,5R,6S,7R,7aR)-5-(acetoxymethyl)-2-propyl-5,6,7,7a-tetrahydro-3aH-pyrano[3,2-d]thiazole-6,7-diyl diacetate | 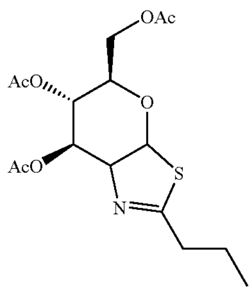 |
| 94 | (3aR,5R,6S,7R,7aR)-5-(acetoxymethyl)-2-butyl-5,6,7,7a-tetrahydro-3aH-pyrano[3,2-d]thiazole-6,7-diyl diacetate | 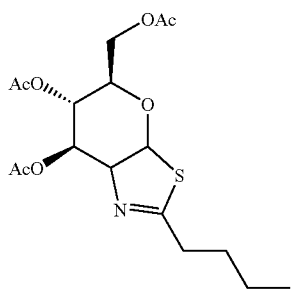 |
| 95 | (3aR,5R,6S,7R,7aR)-5-(acetoxymethyl)-2-pentyl-5,6,7,7a-tetrahydro-3aH-pyrano[3,2-d]thiazole-6,7-diyl diacetate | 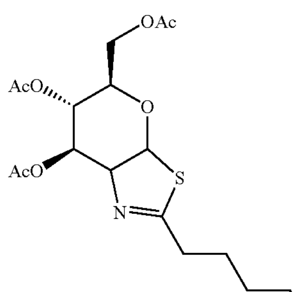 |
| 96 | (3aR,5R,6S,7R,7aR)-5-(acetoxymethyl)-2-isopropyl-5,6,7,7a-tetrahydro-3aH-pyrano[3,2-d]thiazole-6,7-diyl diacetate | 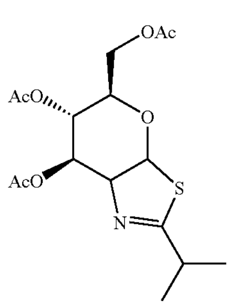 |

TABLE 3-continued

| Compound | Name | Structure |
|---|---|---|
| 97 | (3aR,5R,6S,7R,7aR)-5-(acetoxymethyl)-2-isobutyl-5,6,7,7a-tetrahydro-3aH-pyrano[3,2-d]thiazole-6,7-diyl diacetate | 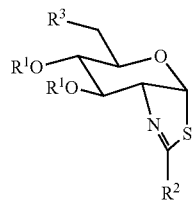 |

In alternative embodiments of the invention, one or more of the compounds described in Tables 1, 2 or 3 are specifically excluded from the compounds described in Formula (I). In alternative embodiments of the invention, specific stereoisomers or enantiomers of one or more of the compounds described in Tables 1, 2 or 3 are specifically excluded from the compounds described in Formula (I). In alternative embodiments of the invention, specific precursors of one or more of the compounds described in Tables 1, 2 or 3 are specifically excluded from the compounds described in Formula (I).

In some embodiments, when each $R^1$ is H and $R^3$ is OH, $R^2$ is not $CH_3$, $CH_2CH_3$, $(CH_2)_2CH_3$, $(CH_2)_3CH_3$, $(CH_2)_4CH_3$, $(CH_2)_6CH_3$, $CH(CH_3)_2$, $CH_2CH(CH_3)_2$, NH(phenyl), NH(4-methoxyphenyl), $N(CH_3)_2$, $(CH_2)_2P(O)(OH)(OCH_3)$, or $(CH_2)_2P(O)(OH)(O(CH_2)_7CH_3)$.

In alternative embodiments, when each $R^1$ is $COCH_3$ and $R^3$ is $OC(O)CH_3$, $R^2$ excludes $CH_3$, $CH_2CH_3$, $(CH_2)_2CH_3$, $(CH_2)_3CH_3$, $(CH_2)_4CH_3$, $(CH_2)_6CH_3$, $CH(CH_3)_2$, $CH_2CH(CH_3)_2$, NH(phenyl), NH(4-methoxyphenyl), $N(CH_3)_2$, $(CH_2)_2P(O)(OH)(OCH_3)$, and $(CH_2)_2P(O)(OH)(O(CH_2)_7CH_3)$, $NHCH_3$, $NH(CH_2)_2CH_3$, $NHCH(CH_3)_2$, $NH(CH_2)_3CH_3$, NH(cyclohexyl), NH(benzyl), $CH_2Br$, $CHBr_2$, $CH_2P(O)(OCH_2CH_3)_2$, $(CH_2)_2P(O)(OCH_3)(O(CH_2)_7CH_3)$, $(CHz)_2$ $P(O)(OCH_3)_2$; $(CH_2)_2P(O)(OCH_3)_2$, $N(COCH_3)$(phenyl), and $N(COCH_3)$(4-methoxyphenyl).

As will be appreciated by a person skilled in the art, Formula (I) above may also be represented alternatively as follows:

$R^1O$, $R^1O$, $R^3$, O, N, S, $R^2$

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

In some embodiments, all of the compounds of the invention contain at least one chiral center. In some embodiments, the formulations, preparation, and compositions including compounds according to the invention include mixtures of stereoisomers, individual stereoisomers, and enantiomeric mixtures, and mixtures of multiple stereoisomers. In general, the compound may be supplied in any desired degree of chiral purity.

In general, a "non-interfering substituent" is a substituent whose presence does not destroy the ability of the compound of Formula (I) to modulate the activity of the O-GlcNAcase enzyme. Specifically, the presence of the substituent does not destroy the effectiveness of the compound as a modulator of the activity of the O-GlcNAcase enzyme.

Suitable non-interfering substituents include: H, alkyl ($C_{1-10}$), alkenyl ($C_{2-10}$), alkynyl ($C_{2-10}$), aryl (5-12 members), arylalkyl, arylalkenyl, or arylalkynyl, each of which may optionally contain one or more heteroatoms selected from O, S, P, and N, and each of which may be further substituted, for example, by =O; or optionally substituted forms of acyl, arylacyl, alkyl alkenyl-, alkynyl- or arylsulfonyl and forms thereof which contain heteroatoms in the alkyl, alkenyl, alkynyl or aryl moieties. Other noninterfering substituents include =O, =NR, halo, CN, $CF_3$, $CHF_2$, $NO_2$, OR, SR, $NR_2$, $N_3$, COOR, and $CONR_2$, where R is H or alkyl, cycloalkyl, alkenyl, alkynyl, aryl, or heteroaryl. Where the substituted atom is C, the substituents may include, in addition to the substituents listed above, halo, OOCR, NROCR, where R is H or a substituent set forth above.

"Alkyl" refers to a straight or branched hydrocarbon chain group consisting solely of carbon and hydrogen atoms, containing no unsaturation and including, for example, from one to ten carbon atoms, and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, and which is attached to the rest of the molecule by a single bond or a double bond.

Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms. Unless stated otherwise specifically in the specification, the alkenyl group may be optionally substituted by one or more substituents as described herein.

"Aryl" refers to a phenyl or naphthyl group, including for example, 5-12 members. Unless stated otherwise specifically herein, the term "aryl" is meant to include aryl groups optionally substituted by one or more substituents as described herein.

"Arylalkyl" refers to a group of the formula —$R_aR_b$ where $R_a$ is an alkyl group as described herein and $R_b$ is one or more aryl moieties as described herein. The aryl group(s) may be optionally substituted as described herein.

"Arylalkenyl" refers to a group of the formula —$R_cR_b$ where $R_c$ is an alkenyl moiety as described herein and $R_b$ is one or more aryl groups as described herein. The aryl group(s) and the alkenyl group may be optionally substituted as described herein.

"Acyl" refers to a group of the formula —$C(O)R_a$, where $R_a$ is an alkyl group as described herein. The alkyl group(s) may be optionally substituted as described herein.

"Arylacyl" refers to a group of the formula —$C(O)R_a$, where $R_b$ is an aryl group as described herein. The aryl group(s) may be optionally substituted as described herein.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. Unless otherwise stated specifically herein, the term "cycloalkyl" is meant to include cycloalkyl groups which are optionally substituted as described herein.

By a "ring structure" is meant a cycloalkyl, aryl, heteroaryl, or any cyclic structure that may be optionally substituted.

"Optional" or "optionally" means that the subsequently described event of circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution. Examples of optionally substituted alkyl groups include, without limitation, methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc. In some embodiments, optionally substituted alkyl and alkenyl groups include $C_{1-6}$ alkyls or alkenyls.

"Halo" refers to bromo, chloro, fluoro, iodo, etc. In some embodiments, suitable halogens include fluorine or chlorine.

An amino group may also be substituted once or twice (to form a secondary or tertiary amine) with a group such as an optionally substituted alkyl group including $C_{1-10}$alkyl (e.g., methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{on}$ alkyl, alkenyl and cycloalkyl are preferred. The amine group may also be optionally substituted with an aromatic or heterocyclic group, aralkyl (e.g., phenyl$C_{1-4}$ alkyl) or heteroalkyl for example, phenyl, pyridine, phenylmethyl (benzyl), phenethyl, pyridinylmethyl, pyridinylethyl, etc. The heterocyclic group may be a 5 or 6 membered ring containing 1-4 heteroatoms.

An amino group may be substituted with an optionally substituted $C_{2-4}$ alkanoyl, e.g., acetyl, propionyl, butyryl, isobutyryl etc., or a $C_{1-4}$alkylsulfonyl (e.g. methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl etc. The heterocycles are as described herein.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as described herein.

Therapeutic Indications

The invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions include, without limitation, tauopathies, such as Alzheimer's disease, neurodegenerative diseases, cardiovascular diseases, diseases associated with inflammation, diseases associated with immunosuppression and cancers. The compounds of the invention are also useful in the treatment of diseases or disorders related to deficiency or over-expression of O-GlcNAcase or accumulation or depletion of O-GlcNAc, or any disease or disorder responsive to glycosidase inhibition therapy. Such diseases and disorders include, but are not limited to, neurodegenerative disorders, such as Alzheimer's disease (AD), and cancer. Such diseases and disorders may also include diseases or disorders related to the accumulation or deficiency in the enzyme OGTase. Also included is a method of protecting or treating target cells expressing proteins that are modified by O-GlcNAc residues, the dysregulation of which modification results in disease or pathology. The term "treating" as used herein includes treatment prevention, and amelioration.

In alternative embodiments, the invention provides methods of enhancing or elevating levels of protein OGlcNAc modification in animal subjects, such as, veterinary and human subjects. This elevation of O-GlcNAc levels can be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects.

In alternative embodiments, the invention provides methods of inhibiting phosphorylation of tau polypeptides, or inhibiting formation of NFTs, in animal subjects, such as, veterinary and human subjects. Accordingly, the compounds of the invention may be used to study and treat AD and other tauopathies.

In general, the methods of the invention are effected by administering a compound according to the invention to a subject in need thereof, or by contacting a cell or a sample with a compound according to the invention, for example, a pharmaceutical composition comprising a therapeutically effective amount of the compound according to Formula (I). More particularly, they are useful in the treatment of a disorder in which the regulation of O-GlcNAc protein modification is implicated, or any condition as described herein. Disease states of interest include Alzheimer's disease (AD) and related neurodegenerative tauopathies, in which abnormal hyperphosphorylation of the microtubule-associated protein tau is involved in disease pathogenesis. In some embodiments, the compounds may be used to block hyperphosphorylation of tau by maintaining elevated levels of O-GlcNAc on tau, thereby providing therapeutic benefit.

Tauopathies that may be treated with the compounds of the invention include: Alzheimer's disease, Amylotrophic lateral sclerosis (ALS), Amylotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, and Tangle-only dementia.

The compounds of this invention are also useful in the treatment of conditions associate with tissue damage or stress, stimulating cells, or promoting differentiation of cells. Accordingly, in some embodiments, the compounds of this invention may be used to provide therapeutic benefit in a variety of conditions or medical procedures involving stress in cardiac tissue, including but not limited to: ischemia; hemorrhage; hypovolemic shock; myocardial infarction; an interventional cardiology procedure; cardiac bypass surgery; fibrinolytic therapy; angioplasty; and stent placement.

Compounds that selectively inhibit O-GlcNAcase activity may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g. idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, systemic lupus erythematosus, myasthenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinophilic myotis, eosinophilic fascitis; and cancers.

In addition, compounds that affects levels of protein O-GlcNAc modification may be used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

The compounds of the invention may be useful for treatment of neurodegenerative diseases, including Parkinson's disease and Huntington's disease. Other conditions that may be treated are those triggered, affected, or in any other way correlated with levels of O-GlcNAc post-translational protein modification. It is expected that the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast lung, prostate, pancreas, colon, rectum, bladder, kidney, ovary; as well as non-Hodgkin's lymphoma and melanoma; epilepsy, pain, or stroke, e.g., for neuroprotection following a stroke.

Pharmaceutical & Veterinary Compositions, Dosages, and Administration

Pharmaceutical compositions including compounds according to the invention, or for use according to the invention, are contemplated as being within the scope of the invention. In some embodiments, pharmaceutical compositions including an effective amount of a compound of Formula (I) are provided.

The compounds of formula (I) and their pharmaceutically acceptable salts, stereoisomers, solvates, and derivatives are useful because they have pharmacological activity in animals, including humans. In some embodiments, the compounds according to the invention are stable in plasma, when administered to a subject.

In some embodiments, compounds according to the invention, or for use according to the invention, may be provided in combination with any other active agents or pharmaceutical compositions where such combined therapy is useful to modulate O-GlcNAcase activity, for example, to treat neurodegenerative, inflammatory, cardiovascular, or immunoregulatory diseases, or any condition described herein. In some embodiments, compounds according to the invention, or for use according to the invention, may be provided in combination with one or more agents useful in the prevention or treatment of Alzheimer's disease. Examples of such agents include, without limitation, acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;

NMDA receptor antagonists such as Namenda® (Axura®, Akatinol®, Ebixa®, Memantine), Dimebon, SGS-742, Neramexane, Debio-9902 SR (Zr-1 SR), etc.;

gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, etc.;

beta-secretase inhibitors such as ATO-Z1, etc.;
alpha-secretase activators, such as NGX267, etc;
amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO2506PO, PPI-558, etc.;
tau aggregation inhibitors such as methylene blue, etc.;
microtubule stabilizers such as AL-108, AL-208, paclitaxel, etc.;
RAGE inhibitors, such as TTP488, etc.;
5-HT1a receptor antagonists, such as Xaliproden, Lecozotan, etc.;
5-HT4 receptor antagonists, such as PRX-03410, etc.;
kinase inhibitors such as SRN-003-556, amfurindamide, LiCl, AZD1080, NP031112, SAR-502250, etc.
humanized monoclonal anti-Aβ antibodies such as Bapineuzumab (AAB-001), LY2062430, RN1219, ACU-5A5, etc.;
amyloid vaccines such as AN-1792, ACC-001
neuroprotective agents such as Cerebrolysin, AL-108, AL-208, Huperzine A, etc.;
L-type calcium channel antagonists such as MEM-1003, etc.;
nicotinic receptor antagonists, such as AZD3480, GTS-21, etc.;
nicotinic receptor agonists, such as MEM 3454, Nefiracetam, etc.;
peroxisome proliferator-activated receptor (PPAR) gamma agonists such as Avandia® (Rosglitazone), etc.;
phosphodiesterase IV (PDE4) inhibitors, such as MK-0952, etc.;
hormone replacement therapy such as estrogen (Premarin), etc.;
monoamine oxidase (MAO) inhibitors such as NS2330, Rasagiline (Azilect®), TVP-1012, etc.;
AMPA receptor modulators such as Ampalex (CX 516), etc.;
nerve growth factors or NGF potentiators, such as CERE-110 (AAV-NGF), T-588, T-817MA, etc.;
agents that prevent the release of luteinizing hormone (LH) by the pituitary gland, such as leuprolide (VP-4896), etc.;
GABA receptor modulators such as AC-3933, NGD 97-1, CP-457920, etc.;
benzodiazepine receptor inverse agonists such as SB-737552 (S-8510), AC-3933, etc.;
noradrenaline-releasing agents such as T-588, T-817MA, etc.

It is to be understood that combination of compounds according to the invention, or for use according to the invention, with Alzheimer's agents is not limited to the examples described herein, but includes combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

In alternative embodiments, the compounds may be supplied as "prodrugs" or protected forms, which release the compound after administration to a subject. For example, the compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987, all of which are incorporated in full by reference herein.

Suitable prodrug forms of the compounds of the invention include embodiments in which $R^1$ is $C(O)R$ and $R^3$ is $OC(O)R$, where R is optionally substituted alkyl, alkenyl, alkynyl, aryl, or heteroaryl. In these cases the ester groups may be hydrolyzed in vivo (e.g. in bodily fluids), releasing the active compounds in which $R^1$ is H and $R^3$ is OH. Preferred prodrug embodiments of the invention are the compounds of Formula (I) where $R^1$ is $C(O)CH_3$ and $R^3$ is $OC(O)CH_3$.

Compounds according to the invention, or for use according to the invention, can be provided alone or in combination with other compounds in the presence of a liposome, an adjuvant or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" includes without limitation any adjuvant, carrier, excipient, glidant, sweetening agent, diluent, preservative, dye/colorant flavor enhancer, surfactant, wetting agent, dispersing agent suspending agent, stabilizer, isotonic agent, solvent, or emulsifier that has been approved, for example, by the United States Food and Drug Administration or other governmental agency as being acceptable for use in humans or domestic animals.

The compounds of the present invention may be administered in the form of pharmaceutically acceptable salts. In such cases, pharmaceutical compositions in accordance with this invention may comprise a salt of such a compound, preferably a physiologically acceptable salt which are known in the art. In some embodiments, the term "pharmaceutically acceptable salt" as used herein means an active ingredient comprising compounds of Formula 1 used in the form of a salt thereof, particularly where the salt form confers on the active ingredient improved pharmacokinetic properties as compared to the free form of the active ingredient or other previously disclosed salt form.

A "pharmaceutically acceptable sale" includes both acid and base addition salts. A "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or prodrug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The compounds or pharmaceutical compositions according to the present invention may be administered by oral or non-oral, e.g., intramuscular, intraperitoneal, intravenous, intracisternal injection or infusion, subcutaneous injection, transdermal or transmucosal routes. In some embodiments, compounds or pharmaceutical compositions in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. The compounds may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaries. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention may be used to treat animals, including mice, rats, horses, cattle, sheep, dogs, cats, and monkeys. However, compounds of the invention can also be used in other organisms, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition requiring modulation of O-GlcNAcase activity.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of an O-GlcNAcase, elevation of O-GlcNAc levels, inhibition of tau phosphorylation, or any condition described herein. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05M, 0.05 nM-15 µM or 0.01 nM-10 µM.

In alternative embodiments, in the treatment or prevention of conditions which require modulation of O-GlcNAcase activity, an appropriate dosage level will generally be about 0.01 to 500 mg per kg subject body weight per day, and can be administered in singe or multiple doses. In some embodiments, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, the compounds exhibit a suitable safety profile for therapeutic use. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

Other Uses and Assays

A compound of Formula (I) may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluorescence or UV-based assay known in the art may be used. A "test compound" is any naturally-occurring or artificially-derived chemical compound. Test compounds may include, without limitation, peptides, polypeptides, synthesised organic molecules, naturally occurring organic molecules, and nucleic acid molecules. A test compound can "compete" with a known compound such as a compound of Formula (I) by, for example, interfering with inhibition of O-GlcNAcase-dependent cleavage of O-GlcNAc or by interfering with any biological response induced by a compound of Formula (I).

Generally, a test compound can exhibit any value between 10% and 200%, or over 500%, modulation when compared to a compound of Formula (I) or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator will in general decrease modulation relative to a known compound, while a compound that is a positive modulator will in general increase modulation relative to a known compound.

In general, test compounds are identified from large libraries of both natural products or synthetic (or semi-synthetic)

extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to modulate inhibition of O-GlcNAcase-dependent cleavage of O-GlcNAc, or any biological response induced by a compound of Formula (I), further fractionation of the positive lead extract is necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, diagnostic, or other value may be subsequently analyzed using a suitable animal model, as described herein on known in the art.

In some embodiments, the compounds are useful in the development of animal models for studying diseases or disorders related to deficiencies in O-GlcNAcase, over-expression of O-GlcNAcase, accumulation of O-GlcNAc, depletion of O-GlcNAc, and for studying treatment of diseases and disorders related to deficiency or over-expression of O-GlcNAcase, or accumulation or depletion of O-GlcNAc. Such diseases and disorders include neurodegenerative diseases, including Alzheimer's disease, and cancer.

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner. Many compounds in the following examples were prepared according to the synthetic route outlined in Scheme 1.

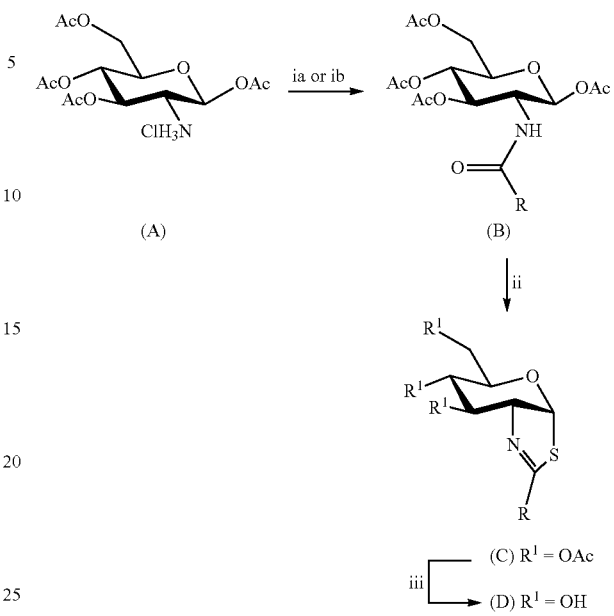

Scheme 1: Preparation of compounds ia) RCOCl, Et$_3$N, CH$_2$Cl$_2$, 0° C.;
ib) EDC or DCC, RCOOH
ii) Lawesson's Reagent, Tol, Δ;
iii) a) NaOMe, MeOH, b) AcOH, MeOH General Procedures:

General Procedure A: Synthesis of 2-amido sugars (B). To a suspension of (2S,3R,4R,5S,6R)-6-(acetoxymethyl)-3-amino-tetrahydro-2H-pyran-2,4,5-triyl triacetate hydrochloride (2.0 g, 5.2 mmol) in CH$_2$Cl$_2$ (50 mL) was added triethylamine (1.45 mL, 10.4 mmol), at which time the starting material dissolved. The reaction mixture was cooled to 0° C., and 1.5 equiv of the appropriate acid chloride (7.8 mmol) was added via syringe. The resultant mixture was stirred for 2 h at room temperature. When the reaction mixture was judged complete by TLC analysis, EtOAc (200 mL) was added. The organic phase was washed successively with water, 1 M aqueous NaOH, and brine. The organic phase was dried (MgSO$_4$) and concentrated to yield a white crystalline solid. The material thus obtained was recrystallized (EtOAc/hexanes) to yield the desired N-acylated materials.

General Procedure B: Synthesis of tri-O-acetyl-protected thiazolines (C). Lawesson's reagent (0.6 eq) was added to a solution of the appropriate amide (B) in anhydrous toluene, and the reaction mixture was refluxed for 2-8 h. The reaction stopped when conversion was judged complete by TLC analysis, at which time the solution was cooled to room temperature, and the solvent was removed in vacuo. The desired material was isolated by flash column silica chromatography using a solvent system of hexanes and EtOAc in ratios ranging from 5:1 to 10:1 as appropriate. Products were isolated and used in the next step without her purification.

General Procedure C: Synthesis of deprotected thiazolines (D). A spatula tip of anhydrous sodium methoxide was added to a solution of the appropriate protected thiazoline in MeOH. The basic solution was stirred until the reaction was judged complete by TLC analysis (typically 1 h). A solution of glacial acetic acid in MeOH (1:20) was added dropwise to the reaction mixture until the pH of the solution was found to be neutral. The solvent was then removed in vacuo, and the desired materials were isolated as syrups by flash silica chromatography using a solvent system of EtOAc and MeOH in ratios ranging from 5:1 to 10:1 as appropriate.

Example 1

Compounds 1 and 2: (3aR,5R,6S,7R,7aR)-5-(acetoxymethyl-2-(fluoromethyl)-5,6,7,7a-tetrahydro-3aH-pyrano[3,2-d]thiazole-6,7-diyl diacetate (1) and (3aR,5R,6S,7R,7aR)-2-fluoromethyl-5-(hydroxymethyl)-5,6,7,7a-tetrahydro-3aH-pyrano[3,2-d]thiazole-6,7-diol (2)

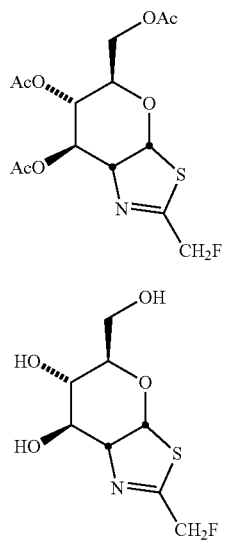

Triethylamine (0.8 mL) and dry pyridine (20 mL) were added to a cooled (0° C.) solution of 2-amino-2-deoxy-1,3,4,6-tetra-O-acetyl-β-D-glucopyranose hydrochloride (1 g) in a solution of DMF (100 mL). Sodium fluoroacetate (1.8 g) was added to a stirred mixture of dry DMF (90 mL) containing dried Dowex 50-H⁺ resin (12 g). After 1 h, DCC (3.2 g) and 30 mL of the fluoroacetic acid solution were added via cannula to the reaction vessel containing the hydrochloride salt. The resulting solution was allowed to stand for 16 h at 0° C., after which time the reaction was judged complete by TLC analysis. The solvent was partially removed in vacuo and EtOAc (300 ml) and a solution of saturated sodium chloride (100 mL) were added. The organic layer was collected, and the aqueous layer was extracted twice with EtOAc. The combined organic extracts were washed successively with water, twice with saturated aqueous $NaHCO_3$, and finally with a solution of brine. The organic extracts were dried over $MgSO_4$ and filtered, and the solvent was removed in vacuo to yield colorless syrup. The desired product was purified using flash chromatography on silica gel (2:1; hexanes/EtOAc) to yield the partially purified amide that was used in the next step without further purification.

The title compounds were prepared from the material thus obtained following General Procedures B and C. For 2: $^1$H NMR (500 MHz, methanol-$d_4$) δ 3.28 (dd, 1H, J=2.5, 6.4 Hz), 3.54 (m, 1H), 3.57 (m, 1H), 3.70 (m, 1H), 4.14 (t, 1H, J=4.1 Hz), 4.38 (m, 1H), 5.17 (tdd, 2H, J=2.2, 13.1, 53.4 Hz), 6.41 (d, 1H, J=7.0 Hz).

Example 2

Compounds 3 and 4: (3aR,5R,6S,7R,7aR)-5-(acetoxymethyl)-2-(difluoromethyl)-5,6,7,7a-tetrahydro-3aH-pyrano[3,2-d]thiazole-6,7-diyl diacetate (3) and (3aR,5R,6S,7R,7aR)-2-(difluoromethyl)-5-(hydroxymethyl)-5,6,7,7a-tetrahydro-3aH-pyrano[3,2-d]thiazole-6,7-diol (4)

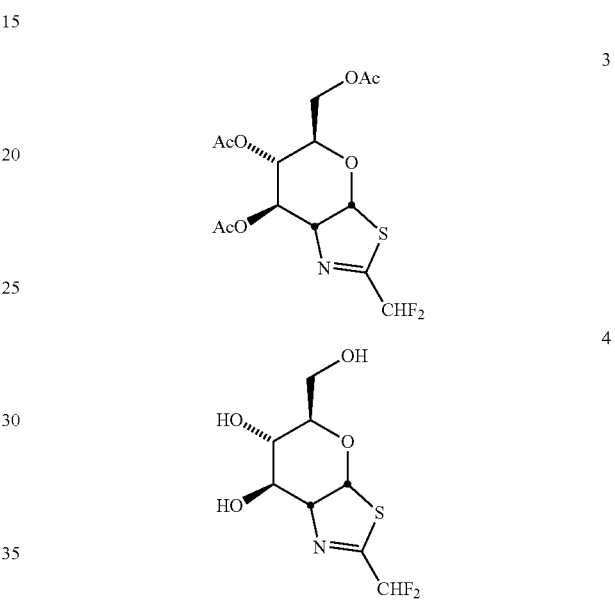

Triethylamine (0.8 mL) and dry pyridine (20 mL) were added to a cooled (0° C.) solution of 2-amino-2-deoxy-1,3,4,6-tetra-O-acetyl-β-D-glucopyranose hydrochloride (1 g) in a solution of DMF (100 mL). Dicyclohexylcarbodiimide (DCC, 3 g) and difluoroacetic acid (1.2 ml) were added to the reaction mixture via syringe. The resulting solution was allowed to stand for 16 h at 0° C., after which time another 0.5 mL of difluoroacetic acid were added. After a further 3.5 h at room temperature, the reaction was judged complete by TLC analysis. The solvent was partially removed in vacuo and EtOAc (300 mL) and a solution of saturated sodium chloride (100 mL) were added. The organic layer was collected, and the aqueous layer was extracted twice with EtOAc. The combined organic extracts were washed successively with water, twice with saturated aqueous $NaHCO_3$, and finally with a solution of brine. The organic extracts were dried over $MgSO_4$ and filtered, and the solvent was removed in vacuo to yield colorless syrup. The desired product was purified using flash chromatography on silica gel (3:1; hexanes/EtOAc) to yield the partially purified amide that was used in the next step without further purification.

The title compounds were prepared from the material thus obtained following General Procedures B and C. For 4: $^1$H NMR (500 MHz, methanol-$d_4$) δ 3.27 (dd, 1H, J=2.5, 6.3 Hz), 3.55 (m, 1H), 3.58 (m, 1H), 3.71 (m, 1H), 4.14 (t, 1H, J=4.6 Hz), 4.44 (m, 1H), 6.43 (t, 1H, J=54.3 Hz), 6.50 (d, 1H, J=7.1 Hz).

Example 3

Compounds 5 and 6: (3aR,5R,6S,7R,7aR)-5-(acetoxymethyl)-2-(trifluoromethyl)-5,6,7,7a-tetrahydro-3aH-pyrano[3,2-d]thiazole-6,7-diyl diacetate (5) and (3aR,5R,6S,7R,7aR)-5-(hydroxymethyl)-2-(trifluoromethyl)-5,6,7,7a-tetrahydro-3aH-pyrano[3,2-d]thiazole-6,7-diol (6)

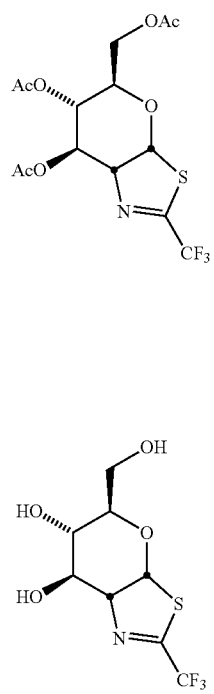

Triethylamine (0.8 mL) was added to a solution of 2-amino-2-deoxy-1,3,4,6-tetra-O-acetyl-β-D-glucopyranose hydrochloride (1 g) dissolved in dry dichloromethane (20 mL) and cooled (0° C.). Trifluoroacetic anhydride (0.6 mL) was added via syringe and the resulting solution was allowed to stand for 16 h at 0° C., after which time the reaction was judged complete by TLC analysis. The solution was diluted in 50 mL of EtOAc and washed successively with water, twice with saturated aqueous NaHCO₃, and finally with a solution of brine. The organic extracts were dried over MgSO₄ and filtered, and the solvent was removed in vacuo to yield colorless syrup. The desired product was purified using flash chromatography on silica gel (4:1; hexanes/EtOAc) to yield the partially purified amide that was used in the next step without fiber purification.

The title compounds were prepared from the material thus obtained following General Procedures B and C. For 6: $^1$H NMR (500 MHz, methanol-d₄) δ: 3.29 (m, 1H), 3.55 (m, 1H), 3.59 (m, 1H), 3.72 (m, 1H), 4.12 (t, 1H, J=4.5 Hz), 4.38 (m, 1H), 6.64 (d, 1H, J=7.1 Hz).

Example 4

Compounds 7 and 8: (3aR,5R,6S,7R,7aR)-5-(acetoxymethyl)-2-(but-3-enyl)5,6,7,7a-tetrahydro-3aH-pyrano[3,2-d]thiazole-6,7-diyl diacetate (7) and (3aR,5R,6S,7R,7aR)-2-(but-3-enyl)-5-(hydroxymethyl)-5,6,7,7a-tetrahydro-3aH-pyrano[3,2-d]thiazole-6,7-diol (8)

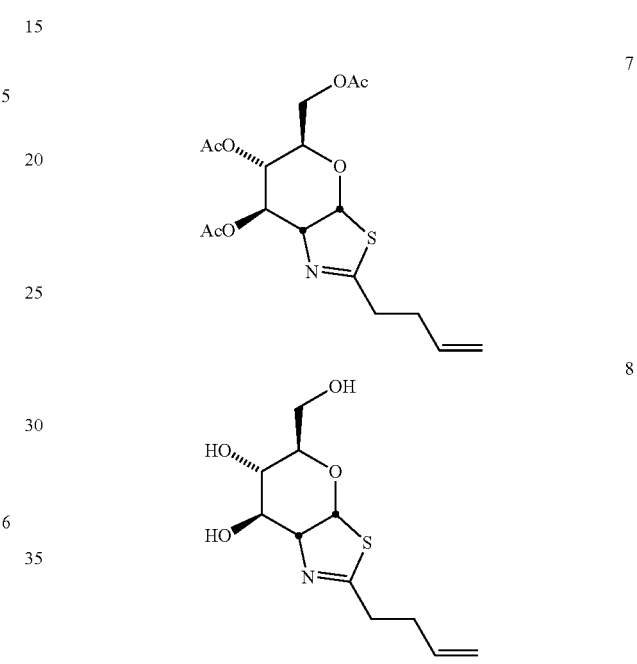

Following General Procedure A, (2S,3R,4R,5S,6R)-6-(acetoxymethyl)-3-amino-tetrahydro-2H-pyran-2,4,5-triyl triacetate hydrochloride and pent-4-enoyl chloride were converted to (2S,3R,4R,5S,6R)-6-(acetoxymethyl)-3-pent-4-enamido-tetrahydro-2H-pyran-2,4,5-triyl tiacetate. $^1$H NMR (500 MHz, CDCl₃) δ 2.01 (s, 3H), 2.02 (s, 3H), 2.07 (s, 3H), 2.08 (s, 3H), 2.18-2.22 (m, 2H), 2.28-2.32 (m, 2H), 3.80 (ddd, 1H, J=2.1, 4.6, 9.5 Hz), 4.10 (dd, 1H, J=2.1, 12.5 Hz), 4.24 (dd, 1H, J=4.6, 12.5 Hz), 4.30 (dd, 1H, J=9.2, 19.3 Hz), 4.95 (ddd, 1H, J=1.6, 3.1, 10.2 Hz), 5.01 (ddd, 1H, J=1.6, 2.6, 17.2 Hz), 5.10 (dd, 1H, J=9.5, 9.5 Hz), 5.16 (dd, 1H, J=9.5, 9.5 Hz), 5.68 (d, 1H, J=8.8 Hz), 5.74 (dddd, 1H, J=2.6, 3.1, 10.2, 17.2 Hz), 5.98 (d, 1H, J=9.5 Hz).

Following General Procedure B, the amide obtained above was converted to (3aR,5R,6S,7R,7aR)-5-(acetoxymethyl)-2-(but-3-enyl)-5,6,7,7a-tetrahydro-3aH-pyrano[3,2-d]thiazole-6,7-diyl diacetate (7). $^1$H NMR (500 MHz, methanol-d₄) δ 2.08 (s, 3H), 2.09 (s, 3H), 2.14 (s, 3H), 2.45 (m, 2H), 2.68 (m, 2H), 3.55 (ddd, 1H, J=3.2, 5.8, 12.3 Hz), 4.09 (dd, 1H, J=5.9, 12.3 Hz), 4.12 (dd, 1H, J=3.2, 12.3 Hz), 4.48 (ddd, 1H, J=1.5, 3.2, 7.0 Hz), 4.94 (m, 1H), 5.02 (m, 1H), 5.10 (m, 1H), 5.58 (dd, 1H, J=1.6, 3.2 Hz), 5.86 (ddd, 1H, J=6.5, 10.3, 17.1 Hz), 6.22 (d, 1H, J=7.2 Hz).

Following General Procedure C, the thiazoline obtained above was converted to the title compound (8). $^1$H NMR (500 MHz, methanol-d₄) δ 2.42 (m, 2H), 2.65 (m, 2H), 3.35 (ddd, 1H, J=2.5, 6.4, 12.1), 3.56 (dd, 1H, J=3.6, 9.1 Hz), 3.61 (dd, 1H, J=6.4, 12.1 Hz), 3.73 (dd, 1H, J=2.5, 12.1 Hz), 4.12 (t, 1H, J=4.2 Hz), 4.32 (m, 1H), 5.02 (m, 1H), 5.10 (m, 1H), 5.86 (ddd, 1H, J=6.5, 10.2, 17.1 Hz), 6.35 (d, 1H, J=7.0 Hz). $^{13}$C NMR (125 MHz, methanol-d$_4$) δ 31.42, 34.08, 62.26, 70.02, 73.10, 75.08, 79.01, 89.05, 115.22, 136.71, 173.51.

Example 5

Compounds 9 and 10: (3aR,5R,6S,7R,7aR)-(acetoxymethyl)-2-(E,Z)-(pent-3-enyl)-5,6,7,7a-tetrahydro-3aH-pyrano[3,2-d]thiazole-6,7-diyl diacetate (9 and (3aR,5R,6S,7R,7aR)-5-hydroxymethyl)-2-(E,Z)-(pent-3-enyl)-5,6,7,7a-tetrahydro-3aH-pyrano[3,2-d]thiazole-6,7-diol (10)

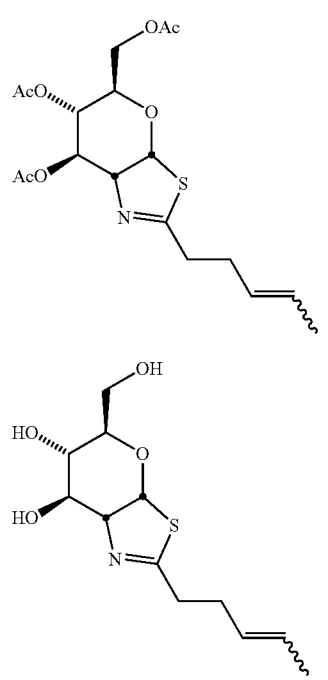

Following General Procedure A, (2S,3R,4R,5S,6R)-(acetoxymethyl)-3-amino-tetrahydro-2H-pyran-2,4,5-triyl triacetate hydrochloride and (E,Z)hex-4-enoyl chloride were converted to (2S,3R,4R,5S,6R)-6-(acetoxymethyl)-3-((E,Z)-hex-4-enamido)-tetrahydro-2H-pyran-2,4,5-triyl triacetate. $^1$H NMR (500 MHz, CDCl$_3$) δ 1.61-1.65 (m, 3H), 2.04 (s, 3H), 2.05 (s, 3H), 2.10 (s, 3H), 2.11 (s, 3H), 2.14-2.20 (m, 2H), 2.22-2.28 (m, 2H), 3.78-3.82 (m, 1H), 4.13 (dd, 1H, J=2.2, 12.5 Hz), 4.27 (dd, 1H, J=4.6, 12.5 Hz), 4.28-4.36 (m, 1H), 5.10-5.18 (m, 2H), 5.32-5.40 (m, 1H), 5.42-5.52 (m, 1H), 5.51-5.54 (m, 1H), 5.67-5.70 (m, 1H).

Following General Procedure B, the amide obtained above was converted to (3aR,5R,6S,7R,7aR)-5-(acetoxyethyl)-2-((E,Z)-pent-3-enyl)-5,6,7,7a-tetrahydro-3aH-pyrano[3,2-d]thiazole-6,7-diyl diacetate (9). $^1$H NMR (500 MHz, methanol-d$_4$) δ 1.60 (m, 3H), 2.04 (s, 3H), 2.05 (s, 3H), 2.10 (s, 3H), 2.35 (m, 2H), 2.61 (m, 2H), 3.5 (m, 1H), 4.08 (d, 2H, J=4.5 Hz), 4.45 (m, 1H), 4.91 (d, 1H, J=9.5 Hz), 5.45 (m, 2H), 5.55 (dd, 1H, J=1.3, 3.1 Hz), 6.18 (d, 1H, J=7.2 Hz).

Following General Procedure C, the thiazoline obtained above was converted to the title compound (10). $^1$H NMR (500 MHz, methanol-d$_4$) δ 1.64 (d, 3H, J=6.0 Hz), 2.35 (m, 2H), 2.60 (m, 2H), 3.34 (ddd, 1H, J=2.0, 6.3, 12.0), 3.56 (dd, 1H, J=3.7, 9.2 Hz), 3.61 (dd, 1H, J=6.3, 12.0 Hz), 3.73 (dd, 1H, J=2.0, 12.0 Hz), 4.12 (t, 1H, J=4.2 Hz), 4.30 (t, 1H, J=5.9 Hz), 5.50 (m, 2H), 6.35 (d, 1H, J=7.0 Hz). $^{13}$C NMR (125 MHz, methanol-d$_4$) δ 16.88, 30.36, 34.72, 62.30, 70.14, 73.12, 75.04, 78.97, 88.88, 126.41, 129.06, 173.81.

Example 6

Compounds 11 and 12: (3aR,5R,6S,7R,7aR)-5-(acetoxymethyl)-2-(methoxymethyl)-5,6,7,7a-tetrahydro-3aH-pyrano[3,2-d]thiazole-6,7-diyl diacetate (11) and (3aR,5R,6S,7R,7aR)-5-hydroxymethyl)-2-(methoxymethyl)-5,6,7,7a-tetrahydro-3aH-pyrano[3,2-d]thiazole-6,7-diol (12)

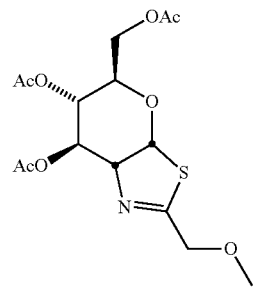

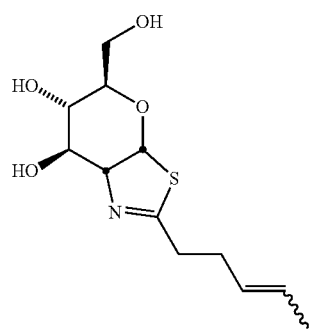

To a suspension of (2S,3R,4R,5S,6R)-6-(acetoxymethyl)-3-amino-tetrahydro-2H-pyran-2,4,5-triyl triacetate hydrochloride (0.500 g, 1.31 mmol) in CH$_2$Cl$_2$ (20 mL) was added triethylamine (0.544 mL, 3.915 mmol), followed by 2-methoxyacetyl chloride (0.13 mL, 1.44 mmol). The reaction was stirred at room temperature for 18 h. The reaction mixture was washed once with saturated aqueous NaHCO$_3$ (3 mL) and once with brine (3 mL). The organic layer was dried (MgSO$_4$), filtered, and concentrated in vacuo. Purification of the crude material by flash chromatography on silica gel (5:1 EtOAc:hexanes) afforded (2S,3R,4R,5S,6R)-6-(acetoxymethyl)-3-(2-methoxyacetamido)-tetrahydro-2H-pyran-2,4,5-triyl triacetate as a white solid (0.380 g, 70% yield).

The amide obtained above was converted to the title compounds following General Procedures B and C. For 12: $^1$H NMR (500 MHz, methanol-4) δ 3.35 (s, 1H), 3.37 (dd, 1H, J=2.5, 12.1 Hz), 3.41 (s, 3H), 3.59 (m, 1H), 4.16 (t, 1H, J=4.0 Hz), 4.29 (m, 2H), 4.38 (m, 1H), 6.36 (d, 1H, J=7.0 Hz). (125 MHz, methanol-d₄) δ 27.22, 30.94, 62.29, 70.09, 70.89, 75.13, 79.25, 89.53, 170, 207.59.

Example 7

Compounds 13 and 14: (3aR,5R,6S,7R,7aR)-5-(acetoxymethyl)-2-(3,3,3-trifluoropropyl)-5,6,7,7a-tetrahydro-3aH-pyrano[3,2-d]thiazole-6,7-diyl diacetate (13) and (3aR,5R,6S,7R,7aR)-5-(hydroxymethyl)-2-(3,3,3-trifluoropropyl)-5,6,7,7a-tetrahydro-3aH-pyrano[3,2-d]thiazole-6,7-diol (14)

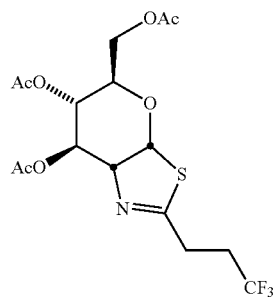

13

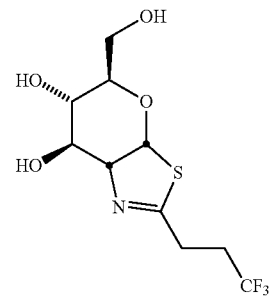

14

To a suspension of (2S,3R,4R,5S,6R)-6-(acetoxymethyl)-3-amino-tetrahydro-2H-pyran-2,4,5-triyl triacetate hydrochloride (0.500 g, 1.31 mmol) in CH₂Cl₂ (20 mL) was added 4-(dimethylamino)pyridine (0.478 g, 3.91 mmol), followed by 1-(3-dimethylaminopropyl)-3-ethylcarbodiimide hydrochloride (0.300 g, 1.57 mmol), and 4,4,4-trifluorobutyric acid (0.222 g, 1.56 mmol). The reaction was stirred at room temperature overnight. The reaction was diluted with CH₂Cl₂ (80 mL) and the organic layer was washed with saturated aqueous NaHCO₃ (10 mL). The organic layer was then dried (MgSO₄) and concentrated in vacuo. Crystallization of the crude material thus obtained (EtOAc/hexanes) afforded (2S,3R,4R,5S,6R)-6-(acetoxymethyl)-3-(4,4,4-trifluorobutanamido)-tetrahydro-2H-pyran-2,4,5-triyl triacetate as a white solid (0.398, 68% yield).

The amide obtained above was converted to the title compounds following General Procedures B and C. For 13: ¹H NMR (500 MHz, CDCl₃) δ 2.09 (s, 3H), 2.10 (s, 3H), 2.15 (s, 3H), 2.48-2.65 (m, 2H), 3.49-3.54 (m, 1H), 4.12-4.13 (m, 2H), 4.48-4.50 (m, 1H), 4.95 (dt, 1H, J=1.5, 4.9 Hz), 5.56 (dd, 1H, J=1.8, 5.6 Hz), 6.28 (d, 1H, J=7.2 Hz). For 14: ¹H NMR (500 MHz, methanol-d₄) δ 2.61 (m, 2H), 2.81 (m, 2H), 3.59 (m, 2H), 3.74 (dd, 1H, J=2.4, 12.1 Hz), 4.15 (t, 1H, J=3.9 Hz), 4.35 (m, 1H), 5.49 (s, 1H), 6.40 (d, 1H, J=7.0 Hz). ¹³C NMR Example 8

Compounds 15 and 16: (3aR,5R,6S,7R,7aR)-5-(acetoxymethyl)-2-(cyclopropylmethyl)-5,6,7,7a-tetrahydro-3aH-pyrano[3,2-d]thiazole-6,7-diyl diacetate (15) and (3aR,5R,6S,7R,7aR)-2-(cyclopropylmethyl)-5-(hydroxymethyl)-5,6,7,7a-tetrahydro-3aH-pyrano[3,2-d]thiazole-6,7-diol (16)

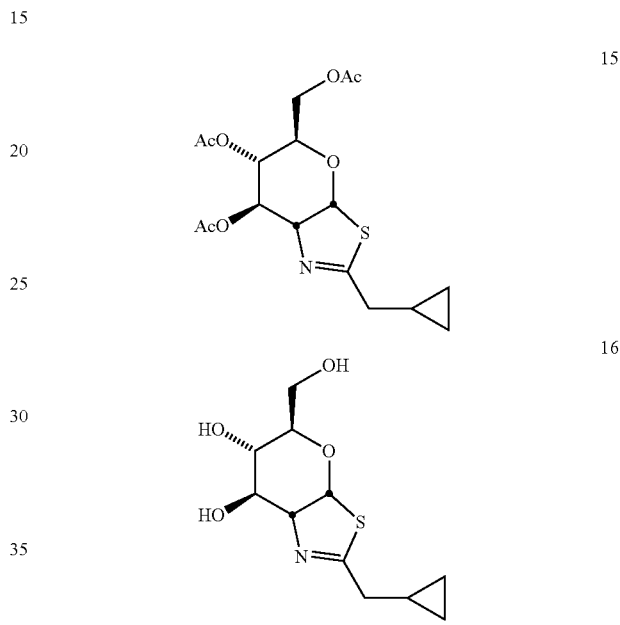

To a suspension of (2S,3R,4R,5S,6R)-6-(acetoxymethyl)-3-amino-tetrahydro-2H-pyran-2,4,5-triyl triacetate hydrochloride (0.500 g, 1.31 mmol) in CH₂Cl₂ (20 mL) was added 4-(dimethylamino)pyridine (0.478 g, 3.91 mmol), followed by 1-(3-dimethylaminopropyl)-3-ethylcarbodiimide hydrochloride (0.300 g, 1.57 mmol), and 2-cyclopropylacetic acid (0.146 mL, 1.57 mmol). The reaction was stirred for 12 h. Additional CH₂Cl₂ (80 mL) was added and the organic layer was washed once with saturated aqueous NaHCO₃ (10 mL). The organic layer was then dried (MgSO₄) and concentrated in vacuo. Flash chromatography of the crude material on silica gel (3:2 EtOAc:hexanes) afforded (2S,3R,4R,5S,6R)-6-(acetoxymethyl)-3-(2-cyclopropylacetamido)-tetrahydro-2H-pyran-2,4,S-triyl tiacetate as a white solid (0.256 g, 56% yield).

The amide obtained above was converted to the title compounds following General Procedures B and C. For 15: ¹H NMR (500 MHz, CDCl₃) δ 0.00-0.03 (m, 2H), 0.30-0.37 (m, 2H), 0.73-0.81 (m, 1H), 1.82 (s, 3H), 1.83 (s, 3H), 1.89 (s, 3H), 2.14-2.28 (m, 2H), 3.31-3.34 (m, 1H), 3.81-3.91 (m, 2H), 4.23-4.26 (m, 1H), 4.70 (d, 1H, J=9.5 Hz), 5.33-5.34 (m, 1H), 5.97 (d, 1H, J=7.1 Hz). ¹³C NMR (500 MHz, CDCl₃) δ 4.92, 5.32, 9.48, 20.96, 21.10, 39, 74, 63.63, 68.58, 69.55, 70.85, 76.34, 88.14, 169.51, 169.77, 170.78, 172.95. For 16: ¹H NMR (500 MHz, methanol-d₄) δ 0.03 (m, 2H), 0.35 (m, 2H), 0.77 (m, 1H), 2.23 (d, 2H, J=7.2 Hz), 3.15 (m, 1H), 3.44 (m, 2H), 3.52 (dd, 1H, J=2.7, 12.0 Hz), 3.94 (t, 1H, J=3.9 Hz), 4.12 (t, 1H, J=5.1 Hz), 6.15 (d, 1H, J=7.0 Hz). $^{13}$C NMR (125 MHz, methanol-$d_4$) δ 4.39, 8.96, 39.41, 62.27, 70.10, 73.04, 75.07, 78.70, 88.56, 174.41.

Example 9

Compounds 17 and 18: (3aR,5R,6S,7R,7aR)-5-(acetoxymethyl)-2-phenyl-5,6,7,7a-tetrahydro-3aH-pyrano[3,2-d]thiazole-67-diyl diacetate (17) and (3aR,5R,6S,7R,7aR)-5-(hydroxymethyl)-2-phenyl-5,6,7,7a-tetrahydro-3aH-pyrano[3,2-d]thiazole-6,7-diol (18)

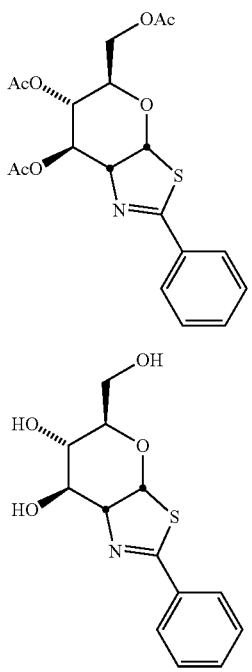

To a suspension of (2S,3R,4R,5S,6R)-6(acetoxymethyl)-3-amino-tetrahydro-2H-pyran-2,4,5-triyl triacetate hydrochloride (0.500 g, 1.31 mmol) in CH$_2$Cl$_2$ (20 ml) was added 4-(dimethylamino)pyridine (0.478 g, 3.91 mmol), followed by benzoyl chloride (0.198 g, 1.57 mmol). The reaction was stirred for 2 h. Additional CH$_2$Cl$_2$ (80 mL) was added and the organic layer was washed once with saturated aqueous NaHCO$_3$ (10 mL). The organic layer was then dried (MgSO$_4$) and concentrated in vacuo. Crystallization of the crude material thus obtained (EtOAc/hexanes) afforded (2S,3R,4R,5S,6R)-6-(acetoxymethyl)-3-benzamido-tetrahydro-2H-pyran-2,4,5-triyl triacetate as a white solid (0.418 g, 69% yield).

The amide obtained above was converted to the title compounds following General Procedures B and C. For 17: $^1$H NMR (500 MHz, CDCl$_3$) δ 2.06 (s, 3H), 2.07 (s, 3H), 2.18 (s, 3H), 3.61-3.64 (m, 1H), 4.73-4.75 (m, 1H), 5.00 (d, 1H, J=9.3 Hz), 5.73-5.74 (m, 1H), 6.37 (d, 1H, J=7.1 Hz), 7.14-7.18 (m, 1H), 7.25 (t, 1H, J=8.0 Hz), 7.46 (t, 2H, J=7.7 Hz), 7.52 (t, 1H, J=7.4 Hz), 7.86 (d, 2H, J=7.2 Hz). For 18: $^1$H NMR (500 MHz, methanol-$d_4$) δ 3.63 (m, 2H), 3.76 (dd, 1H, J=2.5, 12.1 Hz), 4.28 (t, 1H, J=4.3 Hz), 4.57 (dd, 1H, J=5.0, 11.8 Hz), 4.62 (m, 1H), 6.49 (d, 1H, J=6.9 Hz), 7.48 (m, 3H), 7.85 (m, 2H). $^{13}$C NMR (125 MHz, methanol-$d_4$) δ 62.27, 70.27, 73.35, 75.38, 80.21, 88.85, 128.18, 128.52, 131.57, 133.32, 169.25.

Example 10

Compounds 19 and 20: (3aR,5R,6S,7R,7aR)-5-(acetoxymethyl)-2-benzyl-5,6,7,7a-tetrahydro-3aH-pyrano[3,2-d]thiazole-6,7-diyl diacetate (19) and (3aR,5R,6S,7R,7aR)-2-benzyl-5-(hydroxymethyl)-5,6,7,2a-tetrahydro-3aH-pyrano[3,2-d]thiazole-6,7-diol (20)

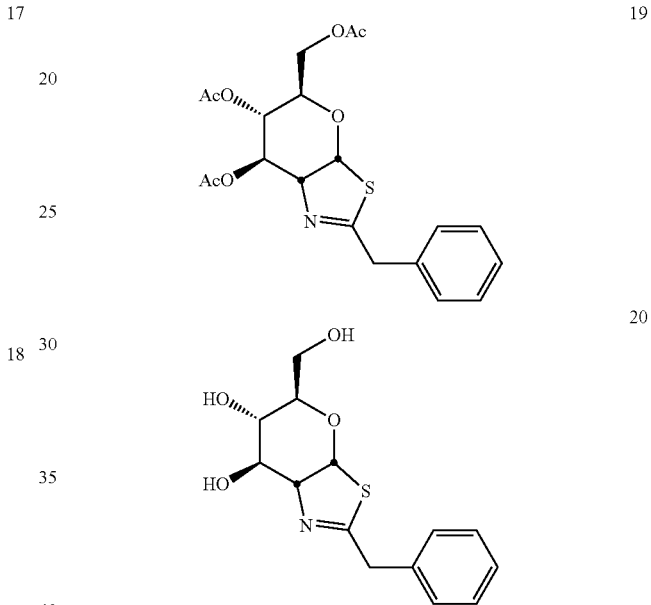

To a suspension of (2S,3R,4R,5S,6R)-6-(acetoxymethyl)-3-amino-tetrahydro-2H-pyran-2,4,5-triyl triacetate hydrochloride (0.500 g, 1.31 mmol) in CH$_2$Cl$_2$ (20 mL) was added 4-(dimethylamino)pyridine (0.478 g, 3.91 mmol) followed by 1-(3-dimethylaminopropyl)-3-ethylcarbodiimide hydrochloride (0.300 g, 1.57 mmol) and 2-phenylacetic acid (0.2132 g, 1.57 mmol). The reaction was stirred for 12 h. Additional CH$_2$Cl$_2$ (80 mL) was added and the organic layer was washed once with saturated aqueous NaHCO$_3$ (10 mL). The organic layer was then dried (MgSO$_4$) and concentrated in vacuo. Flash chromatography of the crude material on silica gel (3:2 EtOAc:hexanes) followed by crystallization (EtOAc/hexanes) afforded (2S,3R,4R,5S,6R)-6-(acetoxymethyl)-3-(2-phenylacetamido)-tetrahydro-2H-pyran-2,4,5-triyl triacetate as a white solid (0.418 g, 69% yield).

The amide obtained above was converted to the title compounds following General Procedures B and C. For 19: $^1$H NMR (500 MHz, CDCl$_3$) δ 2.06 (s, 3H), 2.07 (s, 3H), 2.18 (s, 3H), 3.61-3.64 (m, 1H), 4.73-4.75 (m, 1H), 5.00 (d, 1H, J=9.3 Hz), 5.73-5.74 (m, 1H), 6.37 (d, 1H, J=7.1 Hz), 7.14-7.18 (m, 1H), 7.25 (t, 1H, J=8.0 Hz), 7.46 (t, 2H, J=7.7 Hz), 7.52 (t, 1H, J=7.4 Hz), 7.86 (d, 2H, J=7.2 Hz). For 20: $^1$H NMR (500 MHz, methanol-$d_4$) δ 3.35 (m, 2H), 3.62 (m, 2H), 3.70 (dd, 1H, J=2.6, 12.1 Hz), 3.85 (m, 1H), 4.15 (t, 1H, J=4.48 Hz), 4.36 (t, 1H, J=5.5 Hz), 6.34 (d, 1H, J=7.0 Hz), 7.27 (m, 5H).

$^{13}$C NMR (125 MHz, methanol-d$_4$) δ 40.96, 62.12, 69.94, 73.17, 75.13, 78.89, 89.27, 127.14, 128.59, 129.01, 135.89, 173.17.

Example 11

Compound 21: (3aR,5R,6S,7R,7aR)-2-amino-5-(hydroxymethyl)-5,6,7,7a-tetrahydro-3aH-pyrano[3,2-d]thiazole-6,7-diol

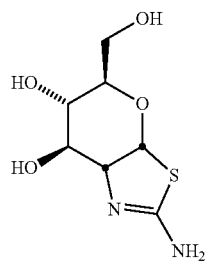

21

To a stirred solution of (2S,3R,4R,5S,6R)-6(acetoxymethyl)-3-amino-tetrahydro-2H-pyran-2,4,5-triyl triacetate hydrochloride (250 mg, 0.65 mmol) in CH$_2$Cl$_2$ (5 mL) was added triethylamine (90 μL, 0.65 mmol). The solution was diluted sated aqueous NaHCO$_3$ (20 mL), then the resulting mixture was extracted with CH$_2$Cl$_2$ (3×10 mL) and the combined organic extracts were dried (Na$_2$SO$_4$) and concentrated to give presumably (2S,3R,4R,5S,6R)-6-(acetoxymethyl)-3-amino-tetrahydro-2H-pyran-2,4,5-triyl triacetate (220 mg) which was used without further purification.

The amine from above (220 mg) was dissolved in pyridine (5 mL) and 9-Fluorenylmethoxycarbonyl isothiocyanate (180 mg, 0.65 mmol) and triethylamine (0.02 mL) was added. Then the resulting mixture was stirred at room temperature for 16 h. The solution was concentrated and the residue taken up in CH$_2$Cl$_2$ (20 mL) and diluted with saturated aqueous NaHCO$_3$ (20 mL), then the resulting mixture was extracted with CH$_2$Cl$_2$ (3×10 mL) and the combined organic extracts were dried (Na$_2$SO$_4$) and concentrated. Flash chromatography of the residue (EtOAc:hexanes 2:3) gave (2S,3R,4R,5S,6R)-6-(acetoxymethyl)-3-(3-(((9H-fluoren-9-yl)methoxy) carbonyl)thioureido)-tetrahydro-2H-pyran-2,4,5-triyl triacetate as a white foam (360 mg, 89% yield over two steps). $^1$H NMR (600 MHz, CDCl$_3$) δ 2.06 (s, 3H), 2.07 (s, 3H), 2.12 (s, 3H), 2.14 (s, 3H), 3.89 (ddd, 1H, J=2.4, 4.8, 9.6 Hz), 4.17 (dd, 1H, J=2.4, 12.5 Hz), 4.24 (dd, 1H, J=6.6, 6.6 Hz), 4.33 (dd, 1H, J=4.8, 12.5 Hz), 4.52 (s, 1H), 4.54 (s, 1H), 5.08-5.12 (m, 1H), 5.22 (dd, 1H, J=9.5, 9.6 Hz), 5.34 (dd, 1H, J=6.6, 9.5 Hz), 5.88 (d, 1H, J=6.6 Hz), 7.36 (dd, 2H, J=7.2, 7.8 Hz), 7.45 (dd, 2H, J=7.2, 7.8 Hz), 7.57 (d, 2H, J=7.8 Hz), 7.80 (d, 2H, J=7.2 Hz). $^{13}$C NMR (150 MHz, CDCl$_3$) δ 20.62, 20.72, 20.77, 21.05, 46.49, 57.59, 61.65, 67.47, 68.40, 72.21, 72.87, 92.21, 120.09, 120.29, 124.84, 124.96, 125.32, 127.30, 127.83, 128.15, 128.25, 129.06, 141.37, 142.80, 152.16, 169.27, 169.34, 170.46, 170.72, 180.22.

The thiourea from above (200 mg, 0.32 mmol) was dissolved in CH$_2$Cl$_2$ (4 mL) and SnCl$_4$ (0.5 mL, 4.0 mmol) was added. Then the resulting mixture was stirred at room temperature for 16 h. The solution was diluted saturated aqueous NaHCO$_3$ (20 mL), then the resulting mixture was extracted with CH$_2$Cl$_2$ (3×10 mL) and the combined organic extracts were dried (Na$_2$SO$_4$) and concentrated. Flash chromatography of the residue (EtOAc:hexanes 2:3) gave (3aR,5R,6S,7R,7aR)-5-(acetoxymethyl)-2-(((9H-fluoren-9-yl)methoxy)carbonylamino)-5,6,7,7a-tetrahydro-3aH-pyrano[3,2-d]thiazole-6,7-diyl diacetate as a pale colourless foam (125 mg, 69% yield). $^1$H NMR 500 MHz, CDCl$_3$) δ 1.88 (s, 3H), 2.04 (s, 3H), 2.12 (s, 3H), 3.69 (m, 1H), 3.81 (ddd, 1H, J=2.5, 5.5, 6.5 Hz), 4.12 (dd, 1H, J=2.5, 12.5 Hz), 4.21-4.26 (m, 2H), 4.55 (dd, 1H, J=6.0, 12.5 Hz), 4.72-4.75 (dd, 1H, J=6.5, 6.5 Hz), 4.95 (dd, 1H J=5.5, 9.5 Hz), 5.24 (dd, 1H J=6.5, 9.5 Hz), 6.01 (d, 1H, J=6.5 Hz), 7.35 (dd, 2H, J=7.1, 7.8 Hz), 7.44 (dd, 2H, J=7.0, 7.8 Hz), 7.59 (d, 2H, J=7.1 Hz), 7.81 (d, 2H, J=7.0 Hz). $^{13}$C NMR (125 MHz, CDCl$_3$) δ 20.62, 20.71, 21.35, 46.78, 57.91, 63.70, 67.92, 69.46, 71.88, 72.52, 90.23, 120.71, 120.89, 123.83, 124.04, 125.15, 127.76, 127.97, 129.61, 129.72, 130.08, 141.31, 142.86, 152.11, 161.43, 169.11, 169.63, 170.23.

The triacetate from above (114 mg, 0.20 mmol) was dissolved in MeOH (2.0 mL) and then NaOMe (14 mg, 0.25 mmol) was added. The resulting mixture was stirred at room temperature for 2 h. The reaction was quenched by the addition of AcOH. Concentration gave a colourless oil which was dissolved in pyridine (3 mL) and then piperidine (0.6 mL) was added. The resulting mixture was stirred at room temperature for 2 h. The mixture was then concentrated and any remaining piperidine was co-evaporated with pyridine. The resultant residue was triturated with EtOAc to give the title compound (38 mg, 81% yield) as a white solid. $^1$H NMR (600 MHz, methanol-d$_4$) δ 3.47 (dd, 1H, J=5.0, 9.0 Hz), 3.57-3.66 (m, 2H), 3.78 (dd, 1H, J=2.0, 12.5 Hz), 3.90 (dd, 1H, J=5.5, 5.5 Hz), 4.04 (dd, in, J=6.0, 6.0 Hz), 6.31 (d, in, J=6.0 Hz). $^{13}$C NMR (125 MHz, methanol-d$_4$) δ 61.15, 69.14, 73.45, 74.14, 74.52, 89.62, 161.08. Anal. Calcd. for C$_7$H$_{12}$N$_2$O$_4$S: C, 38.17; H, 5.49; N, 12.72; Found: C, 38.05; H, 5.37; N, 12.66.

Example 12

Compounds 22 and 23: (3aR,5R,6S,7R,7aR)-5-(acetoxymethyl)-2-(methylamino)-5,6,7,7a-tetrahydro-3aH-pyrano[3,2-d]thiazole-6,7-diyl diacetate (22) and (3aR,5R,6S,7R,7aR)-5-(hydroxymethyl)-2-(methylamino)-5,6,7,7a-tetrahydro-3aH-pyrano[3,2-d]thiazole-6,7-diol (23)

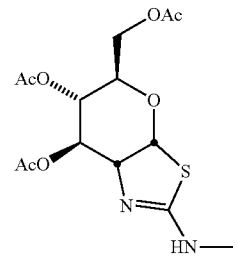

22

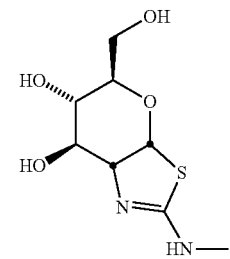

23

To a stirred solution of (2S,3R,4R,5S,6R)-6-(acetoxymethyl)-3-isothiocyanato-tetrahydro-2H-pyran-2,4,5-triyl triacetate (0.51 g, 1.32 mmol) (Jochims, J. C. et al, *Tetrahedron*, 1965, 21(9), 2611-16) in CH$_3$CN, was added neat methylamine hydrochloride (0.18 g, 2.64 mmol). The reaction was stirred at room temperature until complete by TLC (1.5 h). The reaction was washed with a minimal amount of saturated aqueous NaHCO$_3$ (15 mL). The aqueous layer was then extracted three times with DCM, and the organic layers were combined, dried with MgSO$_4$, filtered and concentrated. The concentrated mixture was purified via flash column chromatography on silica gel (EtOAc:hexanes, 1:1), providing (2S,3R,4R,5S,6R)-6-(acetoxymethyl)-3-(3-methylthioureido)-tetrahydro-2H-pyran-2,4,5-triyl triacetate (0.35 g, 62% yield). $^1$H NMR (500 MHz, CDCl$_3$) δ 2.06 (s, 3H), 2.08 (s, 3H), 2.11 (s, 3H), 2.15 (s, 3H), 2.98 (s, 3H), 3.82-3.88 (m, 1H), 4.10-4.16 (m, 2H), 4.28 (dd, 1H, J=4.6, 12.5 Hz), 5.17-5.22 (m, 2H), 5.74 (d, 1H, J=8.1 Hz), 5.92 (s, 1H), 6.21 (s, 1H).

(2S,3R,4R,5S,6R)-6-(acetoxymethyl)-3-(3-methylthioureido)-tetrahydro-2H-pyran-2,4,5-triyl triacetate (0.457 g, 1.09 mmol) was added to dry DCM, and SnCl$_4$ (1.13 g, 4.33 mmol) was added dropwise. The reaction was stirred at room temperature overnight (16 h). The reaction was quenched with saturated aqueous NaHCO$_3$ until the solution was basic and no more gas was evolved. The aqueous layer was extracted three times with DCM and the combined organic layers were dried with MgSO$_4$, filtered and concentrated. The crude material was purified by flash chromatography (silica gel, EtOAc), providing (5R,6S,7R)-5-(acetoxymethyl)-2-(methylamino)-5,6,7,7a-tetrahydro-3aH-pyrano[3,2-d]thiazole-6,7-diyl diacetate (22) as an oil (0.30 g, 77% yield). $^1$H NMR (500 MHz, CDCl$_3$) δ 2.05 (s, 3H), 2.06 (s, 3H), 2.08 (s, 3H), 2.90 (s, 3H), 3.84 (m, 1H), 4.12 (m, 2H), 4.34 (dd, 1H, J=4.3, 6.2 Hz), 4.90 (ddd, 1H, J=0.8, 2.8, 9.6 Hz), 5.39 (dd, 1H, J=2.9, 4.1 Hz), 6.21 (d, 1H, J=6.5 Hz). $^{13}$C NMR (125 MHz, CDCl$_3$) δ 21.00, 21.10, 21.23, 31.19, 63.40, 68.67, 69.40, 72.24, 73.01, 90.03, 161.21, 169.72, 169.90, 170.89.

The product isolated above (0.090 g, 0.250 mmol) was dissolved in anhydrous MeOH. Solid K$_2$CO$_3$ was added to the solution until it was basic, and the reaction was stirred at room temperature (5 h). A white solid, the desired product, precipitated out of solution. The final product, (5R,6S,7R)-5-(hydroxymethyl)-2-(methylamino)-5,6,7,7a-tetrahydro-3aH-pyrano[3,2-d]thiazole-6,7-diol (23), was purified by isolating this solid and washing it several times with MeOH (0.038 g, 64% yield). $^1$H NMR (500 MHz, D$_2$O) δ 2.67 (s, 3H), 3.40-3.43 (m, 1H), 3.48-3.54 (m, 2H), 3.65-3.68 (m, 1H), 3.90 (t, 1H, J=5.1 Hz), 4.04 (t, 1H, J=5.8 Hz), 6.14 (d, 1H, J=6.4 Hz).

$^{13}$C NMR (125 MHz, D$_2$O) δ 29.83, 61.39, 69.28, 73.24, 73.61, 74.19, 88.52, 163.73. MS (CD): m/z 235 (M+1). Anal. Calcd. for C$_8$H$_{14}$N$_2$O$_4$S: C, 41.01; H, 6.02; N, 11.96; Found: C, 40.60; H, 5.56; N, 10.99.

Example 13

Compounds 24 and 25: (3aR,5R,6S,7R,7aR)-5-(acetoxymethyl)-2-(ethylamino)-5,6,7,7a-tetrahydro-3aH-pyrano[3,2-d]thiazole-6,7-diyl diacetate (24) and (3aR,5R,6S,7R,7aR)-2-(ethylamino)-5-(hydroxymethyl)-5,6,7,7a-tetrahydro-3aH-pyrano[3,2-d]thiazole-6,7-diol (25)

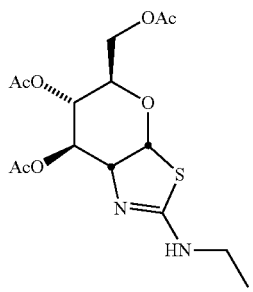

24

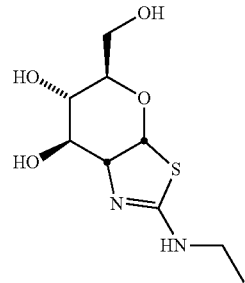

25

To a suspension of (2S,3R,4R,5S,6R)-6-(acetoxymethyl)-3-amino-tetrahydro-2H-pyran-2,4,5-triyl triacetate hydrochloride (2.04 g, 5.19 mmol) in CH$_3$CN (80 mL) was added ethyl isothiocyanate (1.36 g, 15.57 mmol), followed by triethylamine (0.94 g, 9.31 mmol). The reaction mixture was heated to reflux and stirred for 3 h. The organic layer was concentrated, and redissolved in CH$_2$Cl$_2$. The reaction was then washed with a minimal amount of saturated aqueous NaHCO$_3$ solution. The aqueous layer was extracted an additional two times with CH$_2$Cl$_2$. The organic layer was dried (MgSO$_4$), filtered, and concentrated in vacuo. The desired (2S,3R,4R,5S,6R)-6-(acetoxymethyl)-3-(3-ethylthioureido)-tetrahydro-2H-pyran-2,4,5-triyl triacetate was obtained as a yellow oil (2.21 g, 98% yield) following flash chromatography (EtOAc/hexanes, 1:1). $^1$H NMR (500 MHz, CDCl$_3$) δ 1.19 (m, 3H), 1.81 (d, 1H, J=4.0 Hz), 2.05 (s, 3H), 2.08 (s, 3H), 2.10 (s, 3H), 2.14 (s, 3H), 3.40 (s, 1H), 3.85 (m, 1H), 4.12 (m, 1H), 4.28 (m, 1H), 4.81 (s, 1H), 5.19 (m, 1H), 5.73 (d, 1H, J=7.7 Hz), 6.00 (s, 1H), 6.12 (d, 1H, J=15.0 Hz); $^{13}$C NMR (125 MHz, CDCl$_3$) δ 14.39, 20.81, 20.96, 21.07, 21.25, 57.84, 60.67, 61.95, 68.08, 72.99, 73.31, 93.12, 163.03, 169.60, 170.97, 171.88.

The thiourea isolated above (1.74 g, 4.01 mmol) was dissolved in dry CH$_2$Cl$_2$. SnCl$_4$ (1.88 mL, 16.05 mmol) was added dropwise and the reaction turned slightly yellow. The reaction was allowed to stir overnight. The reaction was then quenched using a saturated aqueous solution of NaHCO$_3$ until the solution was neutral and no further CO$_2$ gas was evolved. The aqueous layer was extracted with CH$_2$Cl$_2$ three times, and the combined organic fractions were dried (MgSO$_4$), filtered, and concentrated in vacuo. Purification of the crude material via flash chromatography (silica gel, EtOAc) provided 24 as a pale yellow solid (1.35 g, 90% yield). $^1$H NMR (500 MHz, CDCl$_3$) δ 1.22 (t, 3H, J=7.1 Hz), 2.08 (s, 3H), 2.09 (s, 3H), 2.12 (s, 3H), 3.34 (m, 2H), 3.85 (m, 1H), 4.14 (d, 2H, J=4.3 Hz), 4.37 (ddd, 1H, J=0.8, 4.1, 6.4 Hz), 4.96 (ddd, 1H, J=0.9, 2.6, 9.6 Hz), 5.43 (m, 1H), 6.24 (d, 1H, J=6.5 Hz). $^{13}$C NMR (125 MHz, CDCl$_3$) δ 14.28, 20.81, 20.96, 21.07, 21.25, 57.84, 61.95, 68.08, 72.99, 73.31, 93.12, 169.60, 170.97, 171.88.

Deprotection of the thiazoline 24 described above following General Procedure C provided the title compound (25) as a white solid. $^1$H NMR (500 MHz, methanol-d$_4$) δ 1.22 (t, 3H, J=7.3 Hz), 3.35 (m, 2H), 3.49 (dd, 1H, J=6.1, 9.0 Hz), 3.66, (m, 2H), 3.82 (dd, 1H, J=1.8, 11.7 Hz), 3.89 (t, 1H, J=6.2 Hz), 4.09 (t, 1H, J=6.4 Hz), 6.44 (d, 1H, J=6.4 Hz). $^{13}$C NMR (125 MHz, methanol-d$_4$) δ 13.73, 38.35, 62.07, 69.99, 74.57, 75.11, 89.72, 161.92. MS (CI): m/z 249 (M+1). Anal. Calcd. for C$_9$H$_{16}$N$_2$O$_4$S: C, 43.53; H, 6.49; N, 11.28; Found: C, 43.82; H, 6.62; N, 11.02.

Example 14

Compounds 26 and 27: (3aR,5R,6S,7R,7aR)-5-(acetoxymethyl)-2-(propylamino)-5,6,7,7a-tetrahydro-3aH-pyrano[3,2-d]thiazole-67-diyl diacetate (26) and (3aR,5R,6S,7R,7aR)-5-(hydroxymethyl)-2-(propylamino)-5,6,7,7a-tetrahydro-3aH-pyrano[3,2-d]thiazole-6,7-diol (27)

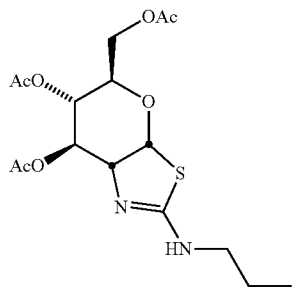

26

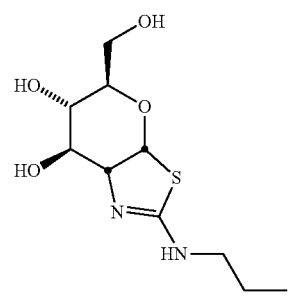

27

To a stirred solution of (2S,3R,4R,5S,6R)-6-(acetoxymethyl)-3-isothiocyanato-tetrahydro-2H-pyran-2,4,5-triyl triacetate (530 mg, 1.36 mmol) in CH$_3$CN (7 mL) was added neat propylamine hydrochloride (260 mg, 2.72 mmol) followed by triethylamine (378 p, 2.72 mmol) and the resulting mixture was stirred for 1 h. Saturated aqueous NaHCO$_3$ (20 mL) was added, then the resulting mixture was extracted with CH$_2$Cl$_2$ (3×10 mL) and the combined organic extracts were dried (MgSO$_4$) and concentrated. The resulting crude material was purified by flash chromatography on silica gel (hexane/EtOAc 1:1) to give (2S,3R,4R,5S,6R)-6-(acetoxymethyl)-3-(3-propylthioureido)-tetrahydro-2H-pyran-2,4,5-triyl triacetate as a white foam (532 mg, 87% yield). $^1$H NMR (500 MHz, CDCl$_3$) δ 0.97 (t, 3H, J=7.5 Hz), 1.59-1.64 (m, 2H), 1.53-1.59 (m, 2H), 2.06 (s, 3H), 2.08 (s, 3H), 2.12 (s, 3H), 2.15 (s, 3H), 3.35 (br s, 2H), 3.81-3.85 (m, 1H), 4.13-4.17 (m, 2H), 4.20-4.25 (m, 1H), 4.29 (dd, 1H, J=4.5, 12.5 Hz), 5.17-5.23 (m, 2H), 5.73 (d, 1H, J=8.5 Hz), 6.07 (br s, 1H).

The thiourea from above (230 mg, 0.51 mmol) was dissolved in CH$_2$Cl$_2$ (2.6 mL) and SnCl$_4$ (240 μL, 2.1 mmol) was added. Then the resulting mixture was stirred for 4 h. The solution was diluted saturated aqueous NaHCO$_3$ (50 mL), then the resulting mixture was extracted with CH$_2$Cl$_2$ (3×20 mL) and the combined organic extracts were dried (Na$_2$SO$_4$) and concentrated. The resulting crude material was purified by flash chromatography on silica gel (hexane/EtOAc 1:1 to 1:1.5) to give (3aR,5R,6S,7R,7aR)-5-(acetoxymethyl)-2-(propylamino)-5,6,7,7a-tetrahydropyrano[3,2-d]thiazole-6,7-diyl diacetate (26) as a pale yellow foam (150 mg, 75% yield). $^1$H NMR (500 MHz) δ 0.93 (t, 3H, J=7.5 Hz), 1.56-1.63 (m, 2H), 2.06 (s, 3H), 2.07 (s, 3H), 2.10 (s, 3H), 3.15-3.20 (m, 1H), 3.26-3.31 (m, 1H), 4.12 (d, 2H, J=4.0 Hz), 4.33-4.35 (m, 1H), 4.91-4.94 (m, 1H), 5.41 (dd, 1H, J=3.0, 4.0 Hz), 6.21 (d, 1H, J=6.5 Hz).

The triacetate from above (150 mg, 0.39 mmol) was dissolved in MeOH (2.5 mL) and then K$_2$CO$_3$ (55 mg, 0.39 mmol) was added. Then the resulting mixture was stirred at room temperature for 2 h. The mixture was diluted with CH$_2$Cl$_2$ (9 mL) and then poured onto the top of a basic Al$_2$O$_3$ (1 g) column. The column was eluted with 10-25% MeOH in CH$_2$Cl$_2$ to give the title compound 27 (57.4 mg, 57% yield) as a white solid. $^1$H NMR (500 MHz, methanol-d$_4$) δ 0.94 (t, 3H, J=7.5 Hz), 1.54-1.60 (m, 2H), 3.14-3.24 (m, 2H), 3.47 (dd, 1H, J=5.0, 8.5 Hz), 3.58-3.66 (m, 2H), 3.78 (dd, 1H, J=2.0, 11.5 Hz), 3.91 (t, 1H, J=6.0 Hz), 4.03 (t, 1H, J=6.0 Hz), 6.28 (d, 1H, J=6.5 Hz). $^{13}$C NMR (125 MHz, methanol-d$_4$) δ 10.59, 22.47, 45.56, 62.03, 69.98, 74.54, 75.10, 89.62, 89.66, 162.17. MS (EI): m/z 263 (M+1). Anal. Calcd. for $C_{10}H_{18}N_2O_4S$: C, 45.79; H, 6.92; N, 10.68; Found: C, 45.58; H, 6.86; N, 10.77.

Example 15

Compounds 28 and 29: (3aR,5R,6S,7R,7aR)-5-(acetoxymethyl)-2-(butylamino)-5,6,7,7a-tetrahydro-3aH-pyrano[3,2-d]thiazole-6,7-diyl diacetate (28) and (3aR,5R,6S,7R,7aR)-2-(butylamino)-5-(hydroxymethyl)-5,6,7,7a-tetrahydro-3aH-pyrano[3,2-d]thiazole-6,7-diol (29)

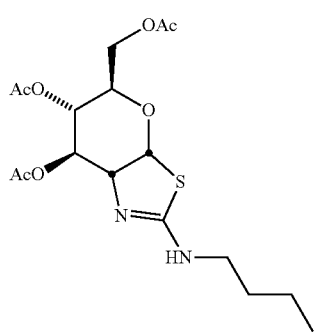

28

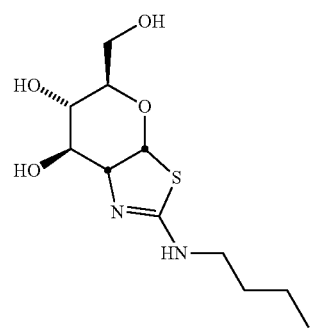

29

To a stirred solution of (2S,3R,4R,5S,6R)-6-(acetoxymethyl)-3-isothiocyanato-tetrahydro-2H-pyran-2,4,5-triyl triacetate (489 mg, 1.26 mmol) in $CH_2Cl_2$ (5 mL) was added neat butylamine (197 μL, 2.00 mmol) and the resulting mixture was stirred for 30 min. Saturated aqueous $NaHCO_3$ (20 mL) was added, then the resulting mixture was extracted with $CH_2Cl_2$ (3×10 mL) and the combined organic extracts were dried ($MgSO_4$) and concentrated. The resulting crude material was purified by flash chromatography on silica gel (hexane(EtOAc 1:1) to give (2S,3R,4R,5S,6R)-6-(acetoxymethyl)-3-(3-butylthioureido)tetrahydro-2H-pyran-2,4,5-triyl triacetate as a white foam (566 mg, 97% yield). $^1$H NMR (500 MHz, $CDCl_3$) δ 0.94 (t, 3H, J=7.5 Hz), 1.35-1.41 (m, 2H, 1.53-1.59 (m, 2H), 2.06 (s, 3H), 2.08 (s, 3H), 2.10 (s, 3H), 2.14 (s, 3H), 3.38 (br s, 2H), 3.82-3.85 (m, 1H), 4.13-4.16 (m, 2H), 4.20-4.25 (m, 1H), 4.29 (dd, 1H, J=4.5, 12.5 Hz), 5.17-5.22 (m, 2H), 5.73 (d, 1H, J=8.0 Hz), 6.10 (br s, 1H).

The thiourea from above (560 mg, 1.21 mmol) was dissolved in $CH_2Cl_2$ (6 mL) and $SnCl_4$ (567 μL, 4.84 mmol) was added, then the resulting mixture was stirred for 16 h. The solution was diluted saturated aqueous $NaHCO_3$ (50 mL), then the resulting mixture was extracted with $CH_2Cl_2$ (3×20 mL) and the combined organic extracts were dried ($Na_2SO_4$) and concentrated. The resulting crude material was purified by flash chromatography on silica gel (hexane/EtOAc 1:1 to 1:1.5) to give (3aR,5R,6S,7R,7aR)-5-(acetoxymethyl)-2-(butylamino)-5,6,7,7a-tetrahydropyrano[3,2-d]thiazole-6,7-diyl diacetate (28) as a pale yellow oil (320 mg, 66% yield). $^1$H NMR (500 MHz) δ 0.93 (t, 3H, J=7.5 Hz), 1.34-1.40 (m, 2H), 1.53-1.58 (m, 2H), 2.07 (s, 3H), 2.09 (s, 3H), 2.11 (s, 3H), 3.20-3.26 (m, 1H), 3.31-3.36 (m, 1H), 3.82-3.86 (m, 1H), 4.14 (d, 2H, J=4.5 Hz), 4.35-4.37 (m, 1H), 4.56 (br s, 1H), 4.94-4.96 (m, 1H), 5.43 (t, 1H, J=3.2 Hz), 6.22 (d, 1H, J=6.5 Hz).

The triacetate from above (130 mg, 0.32 mmol) was dissolved in MeOH (2 mL) and then $K_2CO_3$ (50 mg, 0.36 mmol) was added, then the resulting mixture was stirred at room temperature for 2 h. The mixture was diluted with $CH_2Cl_2$ (8 mL) and then poured onto the top of a basic $Al_2O_3$ (1 g) column. The column was eluted with 10-25% MeOH in $CH_2Cl_2$ to give the title compound 29 (18.1 mg, 20% yield) as a white solid $^1$H NMR (500 MHz, methanol-$d_4$) δ 0.94 (t, 3H, J=7.5 Hz), 1.34-1.41 (m, 2H), 1.51-1.56 (m, 2H), 3.18-3.27 (m, 1H), 3.47 (dd, 1H, J=5.0, 8.5 Hz), 3.50-3.66 (m, 2H), 3.78 (dd, 1H, J=2.0, 11.5 Hz), 3.91 (t, 1H, J=5.5 Hz), 4.03 (t, 1H, J=5.5 Hz), 6.28 (d, 1H, J=6.5 Hz). $^{13}$C NMR (125 MHz, methanol-$d_4$) δ 12.98, 19.96, 31.37, 43.52, 62.06, 70.01, 74.55, 74.59, 75.14, 89.66, 162.13. MS (EI): m/z 277 (M+1). Anal. Calcd. for $C_{11}H_{20}N_2O_4S.0.2$ ($CH_4O$).0.1 ($C_6H_{14}$): C, 48.65; H, 7.68; N, 9.61; Found: C, 48.30; H, 7.96; N, 9.64.

Example 16

Compounds 30 and 31: (3aR,5R,6S,7R,7aR)-5-(acetoxymethyl)-2-(allylamino)-5,6,7,7a-tetrahydro-3aH-pyrano[3,2-d]thiazole-6,7-diyl diacetate (30) and (3aR,5R,6S,7R,7aR)-2-(allylamino)-5-(hydroxymethyl)-5,6,7,7a-tetrahydro-3aH-pyrano[3,2-d]thiazole-6,7-diol (31)

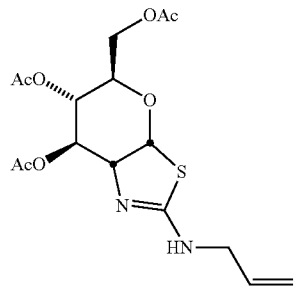

30

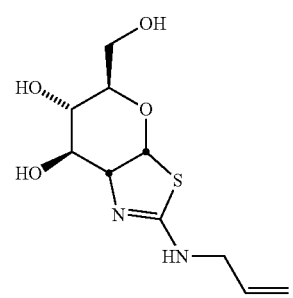

31

To a stirred solution of (2S,3R,4R,5S,6R)-6-(acetoxymethyl)-3-isothiocyanato-tetrahydro-2H-pyran-2,4,5-triyl triacetate (0.50 g, 1.31 mmol) in $CH_3CN$, was added neat 3-isothiocyanatoprop-1-ene (0.155 g, 1.2 mmol), dropwise.

The reaction was stirred at room temperature until complete by TLC (3 h). The reaction was washed with a minimal amount of saturated aqueous NaHCO$_3$ (15 mL). The aqueous layer was then extracted three times with DCM, and the organic layers were combined, dried with MgSO$_4$, filtered and concentrated. The concentrated mixture was purified via flash column chromatography in a solvent system of 1:1 EtOAc and hexanes, providing (2S,3R,4R,5S,6R)-6-(acetoxymethyl)-3-(3-allylthioureido)-tetrahydro-2H-pyran-2,4,5-triyl triacetate (0.410 g, 81% yield) $^1$H NMR (500 MHz, CDCl$_3$) δ 1.98 (s, 3H), 2.00 (s, 3H), 2.03 (s, 3H), 2.05 (s, 3H), 3.81-3.83 (m, 1H), 4.02-4.08 (m, 3H), 4.21 (dd, 1H, J=4.6, 12.5 Hz), 5.06-5.15 (m, 3H), 5.20-5.30 (m, 2H), 5.72 (d, 1H, J=8.6 Hz), 5.75-5.8 (s, 1H), 6.42-6.52 (m, 2H).

The product isolated above (0.410 g, 0.92 mmol) was dissolved in DCM. To this solution, trifluoroacetic acid (0.80 g, 7.0 mmol) was added, and the reaction was allowed to stir overnight (16 h). The reaction was worked up by washing the reaction mixture with saturated aqueous NaHCO$_3$ (20 mL). The aqueous layer was extracted three times with DCM, and the combined organic layers were dried with MgSO$_4$, filtered and concentrated. The concentrated mixture was purified via flash column chromatography in a solvent system of EtOAc. The product, (5R,6S,7R)-5-(acetoxymethyl-(allylamino)-5,6,7,7a-tetrahydro-3aH-pyrano[3,2-d]thiazole-6,7-diyl diacetate (30), was isolated (0.281 g, 90% yield). $^1$H NMR (500 MHz, CDCl$_3$) δ 1.97 (s, 3H), 1.98 (s, 3H), 2.01 (s, 3H), 3.76-3.90 (m, 3H), 4.04-4.05 (m, 2H), 4.27-4.29 (m, 1H), 4.84 (dd, 1H, J=2.4, 9.4 Hz), 5.06 (d, 1H, J=11.3 Hz), 5.16 (d, 1H, J=17.2 Hz), 5.30 (t, 1H, J=3.3 Hz), 5.77-5.84 (m, 1H), 6.17 (d, 1H, J=6.6 Hz), 6.34 (s, 1H). $^{13}$C NMR (125 MHz, CDCl$_3$) δ 20.87, 21.00, 21.16, 47.43, 63.26, 68.75, 68.85, 68.98, 71.26, 71.43, 88.82, 117.08, 133.64, 169.61, 161.84, 170.76.

(5R,6S,7R)-5-(acetoxymethyl)-2-(allylamino)-5,6,7,7a-tetrahydro-3aH-pyrano[3,2-d]thiazole-6,7-diyl diacetate (0.281 g, 0.73 mmol) was dissolved in anhydrous MeOH. Solid K$_2$CO$_3$ was added to the solution until it was basic, and the reaction was stirred at room temperature (1.5 h). The reaction was filtered and then concentrated in vacuo. The crude material was purified via flash column chromatography (DCM:MeOH, 5:2) providing (5R,6S,7R)-2-(allylamino)-5-(hydroxymethyl)-5,6,7,7a-tetrahydro-3aH-pyrano[3,2-d]thiazole-6,7-diol (31) (0.048 g, 18% yield). $^1$H NMR: (500 MHz, methanol-d$_4$) δ 3.50 (dd, 1H, J=5.5, 8.9 Hz), 3.6-3.7 (m, 2H), 3.81 (d, 1H, J=10.7 Hz), 3.87-3.95 (m, 3H), 4.09 (t, 1H, J=6.2 Hz), 5.15 (d, 1H, J=10.3 Hz), 5.25 (d, 1H, J=17.2 Hz), 5.88-5.96 (m, 1H), 6.36 (d, 1H, J=6.4 Hz) $^{13}$C NMR (125 MHz, methanol-d$_4$) δ: 39.23, 61.80, 69.52, 73.52, 74.51, 75.39, 90.67, 161.87, 165.33.

Example 17

Compounds 32 and 33: (3aR,5R,6S,7R,7aR)-5-(acetoxymethyl)-2-(cyclopropylamino)-5,6,7,7a-tetrahydro-3aH-pyrano[3,2-d]thiazole-6,7-diyl diacetate (32) and (3aR,5R,6S,7R,7aR)-2-(cyclopropylamino)-5-(hydroxymethyl)-5,6,7,7a-tetrahydro-3aH-pyrano[3,2-d]thiazole-6,7-diol (33)

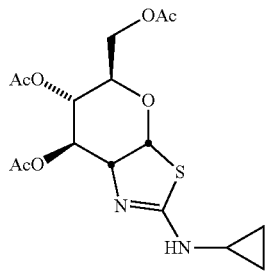

32

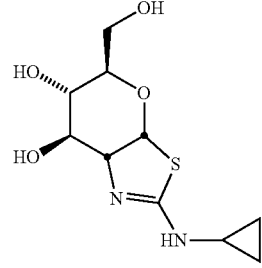

33

To a stirred solution of (2S,3R,4R,5S,6R)-6-(acetoxymethyl)-3-isothiocyanato-tetrahydro-2H-pyran-2,4,5-triyl triacetate$^{115}$ (300 mg, 0.77 mmol) in CH$_2$Cl$_2$ (10 mL) was added neat cyclopropylamine (107 μL, 1.54 mmol) and the resulting mixture was stirred for 1 h. Saturated aqueous NaHCO$_3$ (10 mL) was added, then the resulting mixture was extracted with CH$_2$Cl$_2$ (3×10 mL) and the combined organic extracts were dried (MgSO$_4$) and concentrated. The resulting crude material was purified by flash chromatography on silica gel (hexane/EtOAc 1:1) to give (2S,3R,4R,5S,6R)-6-(acetoxymethyl)-3-(3-cyclopropylthioureido)-tetrahydro-2H-pyran-2,4,5-triyl triacetate as a pale yellow oil (306 mg, 89% yield). $^1$H NMR (500 MHz, CDCl$_3$) δ 0.55-0.59 (m, 2H), 0.77-0.80 (m, 2H), 2.02 (s, 3H), 2.03 (s, 3H), 2.08 (s, 3H), 2.11 (s, 3H), 2.38 (br s, 1H), 3.79-3.83 (m, 1H), 4.11 (dd, 1H, J=2.0, 12.5 Hz), 4.24 (dd, 1H, J=4.5, 12.5 Hz), 5.20 (t, 1H, J=9.5 Hz), 5.26 (t, 1H, J=10.0 Hz), 5.84 (d, 1H, J=8.5 Hz), 6.34 (d, 1H, J=10.0 Hz), 6.75 (br s, 1H). $^{13}$C NMR (125 MHz, methanol-d$_4$) δ: 6.47, 26.00, 61.43, 65.04, 68.57, 73.36, 76.68, 87.89.

The thiourea from above (306 mg, 0.69 mmol) was dissolved in CH$_2$Cl$_2$ (10 mL) and TFA (153 μL, 2.06 mmol) was added, then the resulting mixture was stirred for 18 h. At this time, the solvent was removed under reduced pressure and the residue was redissolved in CH$_2$Cl$_2$ (5 mL). Solid K$_2$CO$_3$ (215 mg, 1.55 mmol) was added, then the mixture was filtered and concentrated. The resulting crude material was purified by flash chromatography on silica gel (CH$_2$Cl$_2$/MeOH 5:1) to give (3aR,5R,6S,7R,7aR)-5-(acetoxymethyl)-2-(cyclopropylamino)-5,6,7,7a-tetrahydro-3aH-pyrano[3,2-d]thiazole-6,7-diyl diacetate (32) as a pale yellow oil (188 mg, 71% yield). $^1$H NMR (500 MHz) δ 0.61-0.64 (m, 2H), 0.75-0.78 (m, 2H), 2.09 (s, 3H), 2.10 (s, 3H), 2.12 (s, 3H), 2.65-2.69 (m, 1H), 3.85 (dt, in, J=4.5, 9.5 Hz), 4.15 (d, 2H, J=4.0 Hz), 4.34 (dd, 1H, J=4.2, 6.4 Hz), 4.95 (ddd, 1H, J=0.5, 2.0, 9.6 Hz), 5.31 (br s, 1H), 5.41 (dd, 1H, J=2.9, 4.0 Hz), 6.21 (d, 1H, J=6.5 Hz).

The triacetate from above (188 mg, 0.49 mmol) was dissolved in MeOH (5 mL) and $K_2CO_3$ (3 mg, 0.02 mmol) was added, then the resulting mixture was stirred vigorously for 1 h. At this time, the mixture was filtered and concentrated. The crude material thus obtained was purified by flash chromatography on silica gel ($CH_2Cl_2$/MeOH 5:2) to give the title compound 33 (66 mg, 52% yield) as a white foam. $^1$H NMR (500 MHz, methanol-$d_4$) δ 0.74-0.77 (m, 2H), 0.90-0.94 (m, 2H), 2.76-2.80 (m, 1H), 3.52 (dd, 1H, J=6.5, 9.0 Hz), 3.65-3.68 (m, 1H), 3.72 (dd, 1H, J=6.0, 12.0 Hz), 3.85 (dd, 1H, J=2.5, 12.0 Hz), 3.91 (t, 1H, J=6.5 Hz), 4.19 (t, 1H, J=6.5 Hz), 6.62 (d, 1H, J=7.0 Hz).

Example 18

Compounds 34 and 35: (3aR,5R,6S,7R,7aR)-5-(acetoxymethyl)-2-(2-fluoroethylamino)-5,6,7,7a-tetrahydro-3aH-pyrano[3,2-d]thiazole-6,7-diyl diacetate (34) and (3aR,5R,6S,7R,7aR)-2-(2-fluoroethylamino)-5-(hydroxymethyl)-5,6,7,7a-tetrahydro-3aH-pyrano[3,2-d]thiazole-6,7-diol (35)

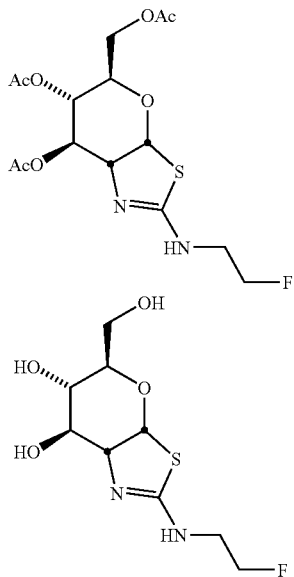

To a stirred solution of (2S,3R,4R,5S,6R)-6-(acetoxymethyl)-3-isothiocyanato-tetrahydro-2H-pyran-2,4,5-triyl triacetate (0.54 g, 1.39 mmol) in $CH_3CN$, was added neat 2-fluoroethanamine (0.28 g, 2.79 mmol), dropwise. The reaction was stirred at room temperature until complete by TLC (3 h). The reaction was washed with a minimal amount of saturated aqueous $NaHCO_3$ (15 mL). The aqueous layer was then extracted three times with DCM, and the organic layers were combined, dried with $MgSO_4$, filtered and concentrated. The concentrated mixture was purified via flash column chromatography in a solvent system of EtOAc and hexanes (1:1), providing (2S,3R,4R,5S,6R)-6-(acetoxymethyl)-3-(3-(2-fluoroethyl)thioureido)-tetrahydro-2H-pyran-2,4,5-triyl triacetate (0.358 g, 57% yield). $^1$H NMR (500 MHz, $CDCl_3$) δ 1.23 (t, 2H, J=7.3 Hz), 2.02 (s, 3H), 2.05 (s, 3H), 2.10 (s, 3H), 2.11 (s, 3H), 3.85-3.88 (m, 2H), 4.07-4.12 (m, 1H), 4.25 (dd, 1H, J=4.6, 12.5 Hz), 4.47-4.53 (m, 1H), 4.54-4.63 (m, 1H), 5.14 (t, 1H, J=9.7 Hz), 5.25 (t, 1H, J=5.4 Hz), 5.73 (d, 1H, J=8.6 Hz), 6.50 (d, 1H, J=9.3 Hz), 6.68 (t, 1H, J=5.4 Hz).

The product isolated above (0.276 g, 0.61 mmol) was added to dry DCM, and $SnCl_4$ (0.64 g, 2.46 mmol) was added dropwise. The reaction mixture was stirred at room temperature overnight (16 h). The reaction was quenched with saturated aqueous $NaHCO_3$ until the solution was basic and no more gas was evolved. The aqueous layer was extracted three times with DCM. The combined organic layers were dried with $MgSO_4$, filtered and concentrated. The crude material was purified by flash chromatography (EtOAc), providing (5R,6S,7R)-5-(acetoxymethyl)2-(2-fluoroethylamino)-5,6,7,7a-tetrahydro-3aH-pyrano[3,2-d]thiazole-6,7-diyl diacetate (34) (0.100 g, 42% yield). $^1$H NMR (500 MHz, $CDCl_3$) δ 2.04 (s, 3H), 2.05 (s, 3H), 2.08 (s, 3H), 3.47-3.66 (m, 2H), 3.7-3.8 (m, 1H), 4.00-4.14 (m, 3H), 4.32 (t, 1H, J=6.3 Hz), 4.42-4.46 (m, 1H), 4.52-4.57 (m, 1H), 4.62-4.66 (m, 1H), 4.92 (d, 1H, J=9.5 Hz), 5.37 (t, 1H, J=3.1 Hz), 6.21 (d, 1H, J=6.5 Hz).

(5R,6S,7R)-5-(acetoxymethyl)-2-(2-fluoroethylamino)-5,6,7,7a-tetrahydro-3aH-pyrano[3,2-d]thiazole-6,7-diyl diacetate (0.074 g, 0.19 mmol) was dissolved in anhydrous MeOH. $K_2CO_3$ was added to the solution until it was basic, and the reaction was stirred at room temperature (1.5 h). The reaction was filtered and then concentrated in vacuo. The crude material was purified via flash column chromatography with a solvent system of 5:1 DCM and MeOH, providing (5R,6S,7R)-2-(2-fluoroethylamino)-5-(hydroxymethyl)-5,6,7,7a-tetrahydro-3aH-pyrano[3,2-d]thiazole-6,7-diol (35) (0.045 g, 90% yield). $^1$H NMR (500 MHz, methanol-$d_4$) δ 3.47-3.67 (m, 5H), 3.78 (dd, 1H, J=2.1, 11.8 Hz), 3.92 (t, 1H, J=5.6 Hz), 4.06 (t, 1H, J=6.1 Hz), 4.40-4.50 (m, 1H), 4.50-4.56 (m, 1H), 6.31 (d, 1H, J=6.4 Hz). $^{13}$C NMR (125 MHz, methanol-$d_4$) δ 62.02, 69.93, 74.41, 75.15, 81.31, 82.64, 89.84, 89.87, 162.00.

Example 19

Compounds 36 and 37: (3aR,5R,6S,7R,7aR)-5-(acetoxymethyl)-2-(2,2-difluoroethylamino)-5,6,7,7a-tetrahydro-3aH-pyrano[3,2-d]thiazole-6,7-diyl diacetate (36) and (3aR,5R,6S,7R,7aR)-2-(2-2-difluoroethylamino)-5-(hydroxymethyl)-5,6,7,7a-tetrahyrdro-3aH-pyrano[3,2-d]thiazole-6,7-diol (37)

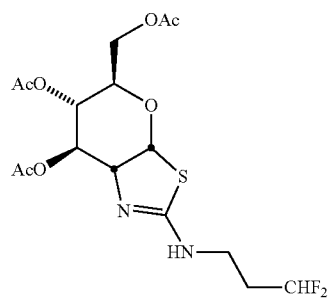

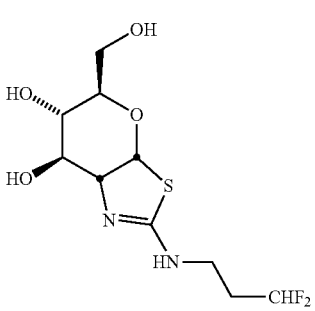

37

To a stirred solution of (2S,3R,4R,5S,6R)-6-(acetoxymethyl)-3-isothiocyanato-tetrahydro-2H-pyran-2,4,5-triyl triacetate (0.64 g, 1.63 mmol) in CH$_3$CN, was added neat 2,2-difluoroethylamine (0.23 g, 1.97 mmol), dropwise. The reaction was stirred at room temperature until complete by TLC (3.5 h). The reaction was washed with a minimal amount of saturated aqueous NaHCO$_3$ (15 mL). The aqueous layer was then extracted three times with DCM, and the organic layers were combined, dried with MgSO$_4$, filtered and concentrated. The concentrated mixture was purified via flash column chromatography in a solvent system of EtOAc and hexanes (1:1, 2:1. then pure EtOAc, respectively), providing (2S,3R,4R,5S,6R)-6-(acetoxymethyl)-3-(3-(2,2-difluoroethyl)thioureido)-tetrahydro-2H-pyran-2,4,5-triyl triacetate (0.433 g, 56% yield) $^1$H NMR (500 MHz, CDCl$_3$) δ 1.99 (s, 3H), 2.00 (s, 3H), 2.03 (s, 3H), 2.06 (s, 3H), 3.83-3.86 (m, 2H), 3.95 (s, 1H), 4.02-4.09 (m, 2H), 4.18-4.23 (m, 1H), 5.05-5.11 (m, 1H), 5.21-5.30 (m, 1H), 5.72 (d, 1H, J=8.6 Hz), 5.94 (t, 1H, J=56.1 Hz), 6.63-6.73 (m, 2H).

The product isolated above (0.320 g, 0.68 mmol) was dissolved in dry DCM, and SnCl$_4$ (0.71 g, 2.73 mmol) was added dropwise. The reaction mixture was stirred at room temperature overnight (16 h). The reaction was quenched with saturated aqueous NaHCO$_3$ until the solution was basic and no more gas was evolved. The aqueous layer was extracted three times with DCM. The combined organic layers were dried with MgSO$_4$, filtered and concentrated. The crude material was purified by flash chromatography (EtOAc:hexanes 1:1, then 2:1, then pure EtOAc) providing (5R,6S,7R)-5-(acetoxymethyl)-2-(2,2-difluoroethylamino)-5,6,7,7a-tetrahydro-3aH-pyrano[3,2-d]thiazole-6,7-diyl diacetate (36) (0.209 g, 75% yield). $^1$H NMR (500 MHz, CDCl$_3$) δ 2.04 (s, 3H), 2.05 (s, 3H) 2.09 (s, 3H), 3.45-3.55 (m, 1H), 3.67-3.77 (m, 2H), 4.06-4.14 (m, 2H), 4.31-4.34 (m, 1H), 4.91-4.93 (d, 1H, J=9.4 Hz), 5.27 (s, 1H), 5.35-5.37 (m, 1H), 6.00 (tt, 1H, J=3.7, 57.5 Hz), 6.24 (d, 1H, J=6.5 Hz).

(5R,6S,7R)-5-(acetoxymethyl)-2-(2,2-difluoroethylamino)-5,6,7,7a-tetrahydro-3aH-pyrano[3,2-]thiazole-6,7-diyl diacetate (0.209 g, 0.51 mmol) was dissolved in anhydrous MeOH. Solid K$_2$CO$_3$ was added to the solution until it was basic, and the reaction was stirred at room temperature (1.5 h). The reaction was filtered and then concentrated in vacuo. The resulting oil was purified via flash column chromatography with a solvent system of 5:1 DCM and MeOH, providing (5R,6S,7R)-2-(2-fluoroethylamino)-5-(hydroxymethyl)-5,6,7,7a-tetrahydro-3aH-pyrano[3,2-d]thiazole-6,7-diol (37) (0.106 g, 74% yield). $^1$H NMR (500 MHz, methanol-d$_4$) δ 3.26-3.27 (m, 1H), 3.43-3.46 (m, 1H), 3.51-3.56 (m, 2H), 3.58-3.61 (m, 1H), 3.74 (dd, 1H, J=2.3, 11.9 Hz), 3.93 (t, 1H, J=5.4 Hz), 4.08 (t, 1H, J=6.0 Hz), 6.01 (tt, 1H, J=4.3, 56.4 Hz), 6.34 (d, 1H, J=6.4 Hz). $^{13}$C NMR (125 MHz, methanol-d$_4$) δ 58.84, 69.85, 74.23, 75.17, 90.09, 114.19 (t, J$_{C-F}$=241 Hz), 161.92.

Example 20

Compounds 38 and 39: (3aR,5R,6S,7R,7aR)-5-(acetoxymethyl)-2-(2,2,2-trifluoroethylamino)-5,6,7,7a-tetrahydro-3aH-pyrano[3,2-d]thiazole-6,7-diyl diacetate (38) and (3aR,5R,6S,7R,7aR)-5-(hydroxymethyl)-2-(2,2,2-trifluoroethylamino)-5,6,7,7a-tetrahydro-3aH-pyrano[3,2-d]thiazole-6,7-diol (39)

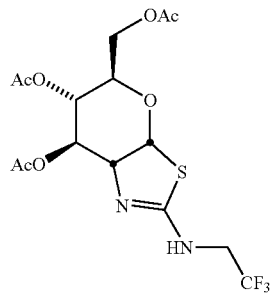

38

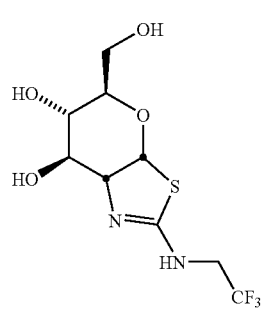

39

To a stirred solution of (2S,3R,4R,5S,6R)-6-(acetoxymethyl)-3-isothiocyanato-tetrahydro-2H-pyran-2,4,5-triyl triacetate (0.56 g, 1.44 mmol) in CH$_3$CN, was added neat 2,2,2-trifluoroethylamine (0.236 g, 1.74 mmol), dropwise. The reaction was stirred at room temperature until complete by TLC (3 h). The reaction was quenched with saturated aqueous NaHCO$_3$ (15 mL). The aqueous layer was then extracted three times with DCM, and the organic layers were combined, dried with MgSO$_4$, filtered and concentrated. The concentrated mixture was purified via flash column chromatography in a solvent system of 1:1 EtOAc and hexanes, providing (2S,3R,4R,5S,6R)-6-(acetoxymethyl)-3-(3,2,2,2-trifluoroethyl)thioureido)-tetrahydro-2H-pyran-2,4,5-triyl triacetate (0.576 g, 81% yield). $^1$H NMR (500 MHz, CDCl$_3$) δ 2.00 (6H, s), 2.04 (s, 3H), 3.87-3.90 (m, 1H), 4.03-4.11 (m, 1H), 4.20-4.26 (m, 2H), 4.36 (s, 1H), 5.07 (t, 1H, J=9.6 Hz), 5.27 (t, 1H, J=9.8 Hz), 5.73 (d, 1H, J=8.5 Hz), 6.75 (s, 2H).

The product isolated above (0.576 g, 1.18 mmol) was added to dry DCM, and SnCl$_4$ (1.23 g, 4.72 mmol) was added dropwise. The reaction mixture was stirred at room temperature overnight (16 h). The reaction was quenched with saturated aqueous NaHCO$_3$ until the solution was basic and no more gas was evolved. The aqueous layer was extracted three times with DCM. The combined organic layers were dried with MgSO$_4$, filtered and concentrated. The crude material was purified by flash chromatography (EtOAc:hexanes 1:1, then 2:1), providing (5R,6S,7R)-5-(acetoxymethyl)-2-(2,2, 2-trifluoroethylamino)-5,6,7,7a-tetrahydro-3aH-pyrano[3,2-d]thiazole-6,7-diyl diacetate (38) (0.328 g, 65% yield). $^1$H NMR (500 MHz, CDCl$_3$) δ 2.00 (s, 3H), 2.02 (s, 3H), 2.06 (s, 3H), 3.71-4.75 (m, 1H), 3.77-3.84 (m, 1H), 3.99-4.11 (m, 3H), 4.29-4.31 (m, 1H), 4.87 (d, 1H, J=10.4 Hz), 5.33-5.34 (m, 1H), 6.58 (d, 1H, J=6.6 Hz).

(5R,6S,7R)-5-(acetoxymethyl)-2-(2,2,2-trifluoroethylamino)-5,6,7,7a-tetrahydro-3aH-pyrano[3,2-d]thiazole-6,7-diyl diacetate (0.328 g, 0.776 mmol) was dissolved in anhydrous MeOH. Solid K$_2$CO$_3$ was added to the solution until it was basic, and the reaction was stirred at room temperature (1 h). The reaction was filtered and then concentrated in vacuo. The final reaction mixture was purified via flash column chromatography with a solvent system of 5:1 DCM and MeOH, providing (5R,6S,7R)-5-(hydroxymethyl)-2-(2,2,2-trifluoroethylamino)-5,6,7,7a-tetrahydro-3aH-pyrano[3,2-d]thiazole-6,7-diol (39) (0.110 g, 47% yield). $^1$H NMR (500 MHz, methanol-d$_4$) δ 3.47-3.50 (m, 1H), 3.61-3.69 (m, 2H), 3.81 (d, 1H, J=11.8 Hz), 3.92 (m, 3H), 4.03 (s, 1H), 4.10 (q, 1H, J=6.9 Hz), 6.35 (d, 1H, J=6.0 Hz). $^{13}$C NMR (125 MHz, methanol-d$_4$) δ 61.94, 69.79, 74.31, 75.35, 123.82, 126.04, 175.25, 225.56.

Example 21

Compounds 40 and 41: (3aR,5R,6S,7R,7aR)-2-(2-acetoxyethylamino)-5-(acetoxymethyl)-5,6,7,7a-tetrahydro-3aH-pyrano[3,2-d]thiazole-6,7-diyl diacetate (40) and (3aR,5R,6S,7R,7aR)-2-(2-hydroxyethylamino)-5-(hydroxymethyl)-5-6,7,7a-tetrahydro-3aH-pyrano[3,2-d]thiazole-6,7-diol (41)

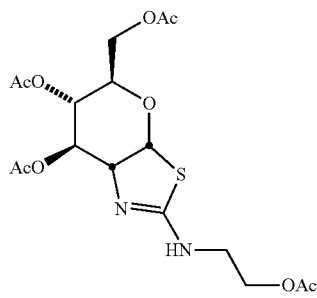

40

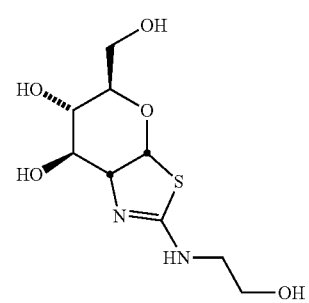

41

To a stirred solution of (2S,3R,4R,5S,6R)-6-(acetoxymethyl)-3-isothiocyanato-tetrahydro-2H-pyran-2,4,5-triyl triacetate (500 mg, 1.3 mmol) in CH$_3$CN (10 mL) was added 2-aminoethyl acetate trifluoroacetate (600 mg, 3 mmol) and triethylamine (0.5 mL, 3.5 mmol). The mixture was stirred at room temperature for 1 h. The solution was diluted with CH$_2$Cl$_2$ (50 mL) and washed with saturated aqueous NaHCO$_3$ (20 mL), and the organic extract was dried (Na$_2$SO$_4$) and concentrated. The residue was purified by flash chromatography on silica gel (hexane/EtOAc 1:1) to give (2S,3R,4R,5S,6R)-(acetoxymethyl)-3-(3-(2-acetoxyethyl) thioureido)-tetrahydro-2H-pyran-2,4,5-triyl triacetate as a white foam (580 mg, 92% yield). $^1$H NMR (600 MHz, DMSO-d$_6$) δ 2.06 (s, 3H), 2.08 (s, 3H), 2.11 (s, 3H), 2.12 (s, 3H), 2.15 (s, 3H), 3.66-3.80 (m, 2H), 3.85 (ddd, 1H, J=2.5, 4.5, 9.0 Hz), 4.14 (dd, 1H, J=2.0, 12.5 Hz), 4.22 (dd, 1H, J=5.0, 5.0 Hz), 4.29 (dd, 1H, J=4.5, 12.5 Hz), 4.65-4.75 (m, 1H), 5.13-5.22 (m, 2H), 5.73 (d, 1H, J=8.5 Hz). $^{13}$C NMR (125 MHz, DMSO-d$_6$) δ 20.82, 20.86, 20.98, 21.04, 21.19, 40.51, 57.21, 61.85, 62.75, 68.25, 71.84, 73.12, 92.65, 169.34, 169.73, 170.13, 170.49, 170.77, 184.26.

The thiourea from above (300 mg, 0.35 mmol) was dissolved in CH$_2$Cl$_2$ (5 mL) and TFA (0.4 mL, 5.4 mmol) was added. Then the resulting mixture was stirred at room temperature for 5 h. The solution was diluted with saturated aqueous NaHCO$_3$ (20 mL), then the resulting mixture was extracted with CH$_2$Cl$_2$ (3×10 mL) and the combined organic extracts were dried (Na$_2$SO$_4$) and concentrated to give (3aR,5R,6S,7R,7aR)-5-(acetoxymethyl)-2-(2-acetoxyethylamino)-5,6,7,7a-tetrahydro-3aH-pyrano[3,2-d]thiazole-6,7-diyl diacetate (40) as a colourless oil (248 mg, 93% yield). This was pure enough for the next reaction. $^1$H NMR (600 MHz, CDCl$_3$) δ 2.11 (s, 9H), 2.14 (s, 3H), 3.52 (ddd, 1H, J=4.2, 7.2, 14.0 Hz), 3.63 (ddd, 1H, J=3.6, 4.2, 14.0 Hz), 3.83 (ddd, 1H, J=3.0, 5.5, 9.0 Hz), 4.13-4.18 (m, 2H), 3.63 (ddd, 1H, J=3.6, 4.2, 11.0 Hz), 4.31 (ddd, 1H, J=4.2, 7.2, 11.0 Hz), 4.38 (dd, 1H, J=3.5, 6.6 Hz), 4.97 (dd, 1H, J=5.5, 9.0 Hz), 5.44 (dd, 1H, J=3.5, 5.5 Hz), 6.26 (d, 1H, J=6.6 Hz). $^{13}$C NMR (150 MHz, CDCl$_3$) δ 20.81, 20.86, 20.91, 21.03, 43.34, 62.72, 63.27, 68.51, 69.08, 71.71, 72.69, 89.98, 159.71, 169.53, 169.75, 170.68, 171.04.

The tetraacetate from above (195 mg, 0.45 mmol) was dissolved in MeOH (10 mL) and then K$_2$CO$_3$ (10 mg, 0.07 mmol) was added. The resulting mixture was stirred at room temperature for 1 h. The mixture was concentrated and then diluted with CH$_2$Cl$_2$ (9 mL) and then poured onto the top of a silica gel column The column was eluted (MeOH:EtOAc 1:1) to give the title compound 41 (105 mg, 88% yield) as a colourless oil. $^1$H NMR (600 MHz, methanol-d$_4$) δ 3.35 (dd, 1H, J=4.8, 6.0 Hz), 3.40-3.45 (m, 1H), 3.49 (dd, 1H, J=5.4, 9.0 Hz), 3.61-3.69 (m, 4H), 3.79 (dd, 1H, J=1.8, 11.4 Hz), 3.95 (dd, 1H, J=5.4, 5.4 Hz), 4.08 (dd, 1H, J=6.0, 6.0 Hz), 6.32 (d, 1H, J=6.0 Hz). $^{13}$C NMR (150 MHz, methanol-d$_4$) δ 47.21, 62.08, 63.36, 71.25, 75.62, 75.72, 76.32, 91.11, 163.68.

Example 22

Compounds 42 and 43: (3aR,5R,6S,7R,7aR)-5-(acetoxymethyl)-2-(dimethylamino)-5,6,7,7a-tetrahydro-3aH-pyrano[3,2-d]thiazole-6,7-diyl diacetate (42) and (3aR,5R,6S,7R,7aR,7aR)-2-(dimethylamino)-5-(hydroxymethyl)-5,6,7,7a-tetrahydro-3aH-pyrano[3,2-d]thiazole-6,7-diol (43)

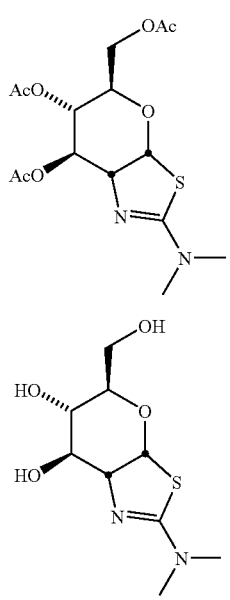

To a stirred solution of (2S,3R,4R,5S,6R)-6-(acetoxymethyl)-34 isothiocyanato-tetrahydro-2H-pyran-2,4,5-triyl triacetate (0.51 g, 1.32 mmol) in CH$_3$CN, was added solid dimethylamine hydrochloride. The reaction was stirred at room temperature until complete by TLC (1 h). The reaction was washed with a minimal amount of saturated aqueous NaHCO$_3$ (15 mL). The aqueous layer was then extracted three times with DCM, and the organic layers were combined, dried with MgSO$_4$, filtered and concentrated. The concentrated mixture was purified via flash column chromatography in a solvent system of EtOAc and hexanes (1:1), providing (2S,3R,4R,5S,6R)-6-(acetoxymethyl)-3-(3,3-dimethylthioureido)-tetrahydro-2H-pyran-2,4,5-triyl triacetate (0.51 g, 91% yield). $^1$H NMR (500 MHz, CDCl$_3$) δ 2.00 (s, 3H), 2.02 (s, 3H), 2.06 (s, 3H), 2.08 (s, 3H), 3.17 (s, 6H), 3.79-3.82 (m, 1H), 4.06-4.13 (m, 1H), 4.22 (dd, 1H, J=4.7, 12.5 Hz), 5.16-5.24 (m, 2H), 5.31 (dd, 1H, J=9.4 Hz), 5.72 (d, 1H, J=9.2 Hz), 5.77 (d, 1H, J=8.4 Hz).

The product isolated above (0.51 g, 1.17 mmol) was dissolved in DCM. To this solution, trifluoroacetic acid (1.0 g, 8.76 mmol) was added, and the reaction was allowed to stir overnight (16 h). The reaction was quenched with saturated aqueous NaHCO$_3$ (20 mL). The aqueous layer was extracted three times with DCM, and the combined organic layers were dried with MgSO$_4$ filtered and concentrated. The concentrated mixture was purified via flash column chromatography (EtOAc:hexanes, 1:1) to provide (5R,6S,7R)-5-(acetoxymethyl)-2-(dimethylamino)-5,6,7,7a-tetrahydro-3aH-pyrano[3,2-d]thiazole-6,7-diyl diacetate (42) (0.19 g, 42% yield). $^1$H NMR (500 MHz, CDCl$_3$) δ 1.99 (s, 3H), 2.00 (s, 3H), 2.02 (s, 3H), 3.10 (s, 6H), 3.90-3.94 (m, 1H), 4.00-4.16 (m, 2H), 4.42 (t, 1H, J=6.1 Hz), 4.92 (dd, 1H, J=5.1, 9.5 Hz), 5.32 (t, 1H, J=5.3 Hz), 6.35 (d, 1H, J=6.7 Hz). $^{13}$C NMR (125 MHz, CDCl$_3$) δ 14.28, 20.80, 41.62, 50.22, 60.60, 62.53, 66.08, 67.65, 70.15, 71.15, 88.07, 88.12, 167.37, 169.77, 170.27, 170.86.

The product isolated above (0.185 g, 0.494 mmol) was dissolved in anhydrous MeOH. K$_2$CO$_3$ was added to the solution until it was basic, and the reaction was stirred at room temperature (1.5 h). The reaction was filtered and then concentrated in vacuo. The final reaction mixture was purified via flash column chromatography with a solvent system of 5:1 DCM and MeOH, providing (5R,6S,7R)-2-(dimethylamino)-5-hydroxymethyl)-5,6,7,7a-tetrahydro-3 aH-pyrano[3,2-d]thiazole-6,7-diol (43) (0.092 g, 75% yield). $^1$H NMR (500 MHz, methanol-d$_4$) δ 3.04 (s, 6H), 3.48 (dd, 1H, J=6.0 Hz), 3.62-3.69 (m, 2H), 3.81 (d, 1H, J=11.7 Hz), 3.87 (t, 1H, J=6.1 Hz), 4.07 (t, 1H, J=6.3 Hz), 6.38 (d, 1H, J=6.5 Hz). $^{13}$C NMR (125 MHz, methanol-d$_4$) δ 39.23, 69.80, 69.52, 73.43, 73.52, 74.51, 79.39, 90.67, 161.87, 165.33.

Example 23

Compounds 44 and 45: (3aR,5R,6S,7R,7aR)-5-(acetoxymethyl)-2-(ethyl(methyl)amino)-5,6,7,7a-tetrahydro-3aH-pyrano[3,2-d]thiazole-6,7-diyl diacetate (44) and (3aR,5R,6S,7R,7aR)-2-(ethyl(methyl)amino)-5-(hydroxymethyl)-5,6,7,7a-tetrahydro-3aH-pyrano[3,2d]thiazole-6,7-diol (45)

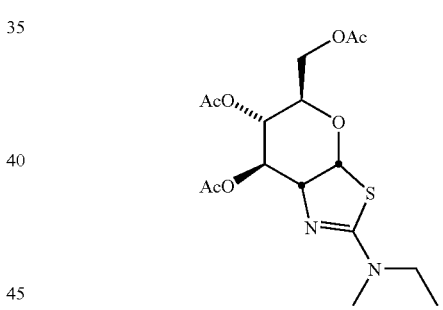

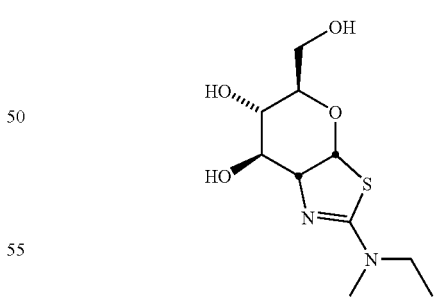

To a stirred solution of (2S,3R,4R,5S,6R)-6(acetoxymethyl)-3-isothiocyanato-tetrahydro-2H-pyran-2,4,5-triyl triacetate (1.10 g, 2.8 mmol) in CH$_2$Cl$_2$ (10 mL) was added neat ethyl(methyl)amine (310 μL, 3.6 mmol) dropwise. The mixture was stirred at room temperature for 1 h. Solvents were removed by concentration. The residue was purified by flash chromatography on silica gel (hexane/EtOAc 1:1) to give (2S,3R,4R,5S,6R)-6-(acetoxymethyl)-3-(3-ethyl-3-methylthioureido)-tetrahydro-2H-pyran-2,4,5-triyl triacetate as a white foam (1.09 g, 86% yield). $^1$H NMR (500 MHz, CDCl$_3$) δ 1.15 (t, 3H, J=7.0 Hz), 2.05 (s, 3H), 2.06 (s, 3H), 2.11 (s, 3H), 2.13 (s, 3H), 3.08 (s, 3H), 3.74-3.81 (m, 3H), 4.16 (dd, 1H, J=2.0, 12.5 Hz), 4.27 (dd, 11, J=4.5, 12.5 Hz), 5.14 (t, 1H, J=10.0 Hz), 5.26 (t, 1H, J=10.0 Hz), 5.34-5.40 (m, 2H), 5.78 (d, 1H, J=8.0 Hz).

The thiourea from above (155 mg, 0.35 mmol) was dissolved in CH$_2$Cl$_2$ (1.5 mL) and TFA (20 μL, 2.63 mmol) was added. Then the resulting mixture was stirred at room temperature for 16 h. The solution was diluted saturated aqueous NaHCO$_3$ (20 mL), then the resulting mixture was extracted with CH$_2$Cl$_2$ (3×10 mL) and the combined organic extracts were dried (Na$_2$SO$_4$) and concentrated to give (3aR,5R,6S,7R,7aR)-5-acetoxymethyl-2-(ethyl(methyl)amino)-5,6,7,7a-tetrahydro-3aH-pyrano[3,2-d]thiazole-6,7-diyl diacetate (44) as a pale yellow foam (134 mg, 100% yield). This was pure enough for the next reaction. $^1$H NMR (500 MHz) δ 1.16 (t, 3H, J=7.0 Hz), 2.06 (s, 3H), 2.08 (s, 3H), 2.10 (s, 3H), 2.98 (s, 3H), 3.24-3.31 (m, 1H), 3.39-3.45 (m, 1H), 3.83-3.86 (m, 1H), 4.14 (d, 2H, J=4.5 Hz), 4.34 (dd, 1H, J=4.5, 6.5 Hz), 4.93 (dd, 1H, J=3.0, 10.0 Hz), 5.40 (dd, 1H, J=3.0, 4.5 Hz), 6.21 (d, 1H, J=6.5 Hz).

The triacetate from above (134 mg, 0.35 mmol) was dissolved in MeOH (2.0 mL) and then K$_2$CO$_3$ (72 mg, 0.52 mmol) was added. The resulting mixture was stirred at room temperature for 2 h. The mixture was diluted with CH$_2$Cl$_2$ (9 mL) and then poured onto the top of a basic Al$_2$O$_3$ (1 g) column. The column was eluted with 10-25% MeOH in CH$_2$Cl$_2$ to give the title compound 45 (57.4 mg, 57% yield) as a white solid. $^1$H NMR (500 MHz, CDCl$_3$) δ 1.07 (t, 3H, J=7.0 Hz), 2.88 (s, 3H), 3.21-3.28 (m, 2H), 3.58-3.60 (m, 2H), 3.67-3.73 (m, 2H), 3.79 (dd, 1H, J=3.5, 7.0 Hz), 3.88 (t, 1H, J=6.5 Hz), 4.07 (t, 1H, J=6.5 Hz), 4.60 (brs, 3H), 628(d, 1H, J=6.5 Hz). $^{13}$C NMR (125 MHz, CDCl$_3$) δ 11.88, 35.70, 46.93, 60.82, 68.02, 73.03, 73.76, 74.02, 90.19, 162.40. MS (EI): m/z 263 (M+1). Anal. Calcd. for C$_{10}$H$_{11}$BN$_2$O$_4$S: C, 45.79; H, 6.92; N, 10.68; Found: C, 46.01; H, 7.18; N, 10.46.

Example 24

Compounds 46 and 47: (3aR,5R,6S,7R,7aR)-5-(acetoxymethyl)-2-(methoxyamino)-5,6,7,7,a-tetrahydro-3aH-pyrano[3,2-d]thiazole-6,7-diyl diacetate (46) and (3aR,5R,6S,7R,7aR)-5-(hydroxymethyl)-2-(methoxyamino)-5,6,7,7a-tetrahydro-3aH-pyrano[3,2-d]thiazole-67-diol (47)

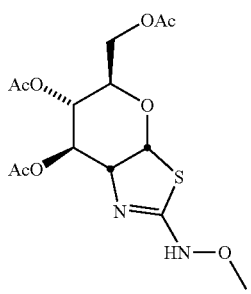

46

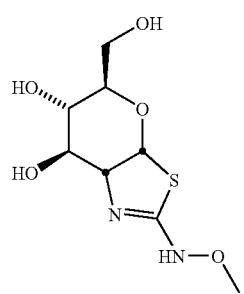

47

To a suspension of methoxyamine hydrochloride (180 mg, 2.16 mmol) in acetonitrile (7 mL) was added (2S,3R,4R,5S,6R)-6-(acetoxymethyl)-3-isothiocyanato-tetrahydro-2H-pyran-2,4,5-triyl triacetate (560 mg, 1.44 mmol) followed by triethylamine (300 μL, 2.16 mmol). The mixture was stirred at room temperature for 2 h. Solvents were removed by concentration. The residue was purified by flash chromatography on silica gel (hexane/EtOAc 1:1) to give (2S,3R,4R,5S,6R)-6-(acetoxymethyl)-3-(3-methoxythioureido)-tetrahydro-2H-pyran-2,4,5-triyl triacetate as a white solid (545 mg, 87% yield). $^1$H NMR (500 MHz, CDCl$_3$) δ 2.05 (s, 3H), 2.09 (s, 3H), 2.10 (s, 6H), 2.13 (s, 3H), 3.67 (s, 3H), 3.82-3.85 (m, 1H), 4.15 (dd, 1H, J=2.5, 12.5 Hz), 4.28 (dd, 1H, J=4.5, 12.5 Hz), 5.03 (dd, 1H, J=10.0, 13.0 Hz), 5.20-5.30 (m, 2H), 5.84 (d, 1H, J=8.5 Hz), 7.01 (d, 1H, J=10.0 Hz).

The thiourea from above (210 mg, 0.48 mmol) was dissolved in CH$_2$Cl$_2$ (2 mL) and TFA (180 μL, 2.41 mmol) was added. The mixture was stirred at room temperature for 16 h. The solution was diluted saturated aqueous NaHCO$_3$ (10 mL), extracted with CH$_2$Cl$_2$ (3×10 mL) and the combined organic extracts were dried (Na$_2$SO$_4$) and concentrated to give the crude product. This was purified by silica gel column, eluted with 1:1 hexane/EtOAc to give (3aR,5R,6S,7R,7aR)-5-(acetoxymethyl)-2-(methoxyamino)-5,6,7,7a-tetrahydro-3aH-pyrano[3,2-d]thiazole-6,7-diyl diacetate (46) as a white foam (122 mg, 67% yield). The $^1$H NMR spectrum showed this was a ca. 1:1 mixture of rotamers. $^1$H NMR (500 MHz) δ 2.05 (s, 3H), 2.07 (s, 3H), 2.08 (s, 6H), 2.09 (s, 3H), 2.11 (s, 3H), 3.75 (s, 3H), 3.77 (s, 3H), 3.88 (t, 1H, J=6.5 Hz), 3.99 (td, 1H, J=6.5, 1.5 Hz), 4.11-4.14 (m, 2H), 4.23-4.31 (m, 4H), 4.98 (d, 1H, J=6.5 Hz), 5.00 (d, 1H, J=6.5 Hz), 5.16 (d, 1H, J=7.0 Hz), 5.19 (d, 1H, J=5.5 Hz), 5.20 (br s, 1H), 5.60 (br s, 1H), 6.10 (d, 1H, J=6.5 Hz), 6.16 (d, 1H, J=6.0 Hz).

The triacetate from above (63 mg, 0.17 mmol) was dissolved in MeOH (1.0 mL) and then K$_2$CO$_3$ (54 mg, 0.39 mmol) was added. The resulting mixture was stirred at room temperature for 30 min. The mixture was diluted with CH$_2$Cl$_2$ (9 mL) and then poured onto the top of a silica gel column. The column was eluted with 5-15% methanol in CH$_2$Cl$_2$ to give the title compound 47 (40 mg, 95% yield) as a white solid. The $^1$H NMR spectrum showed this was a ca. 2:1 mixture of rotamers. $^1$H NMR (500 MHz, methanol-d$_4$) δ 3.35-3.41 (m, 1H), 3.54-3.85 (m, 5H), 3.65 (s, 1H), 3.69 (s, 2 H), 6.16 (d, 0.34H, J=6.0 Hz), 6.31 (d, 0.66H, J=6.0 Hz). $^{13}$C NMR (125 MHz, methanol-d$_4$) δ 60.65, 60.76, 61.14, 61.73, 62.45, 68.75, 68.88, 74.18, 74.83, 75.33, 75.66, 84.21, 84.70, 94.99, 157.65, 160.96. MS (CI): m/z 251 (M+1). Anal. Calcd. for $C_8H_{14}N_2O_5S$: C, 38.39; H, 5.64; N, 11.19; Found: C, 38.20; H, 5.89; N, 11.06.

Example 25

Compounds 48 and 49: (3aR,5R,6S,7R,7aR)-5-(acetoxymethyl)-2-methoxy-5,6,7,7a-tetrahydro-3aH-pyrano[3,2-d]thiazole-6,7-diyl diacetate (48) and (3aR,5R,6S,7R,7aR)-5-(hydroxymethyl)-2-methoxy-5,6,7,7a-tetrahydro-3aH-pyrano[3,2-d]thiazole-6,7-diol (49)

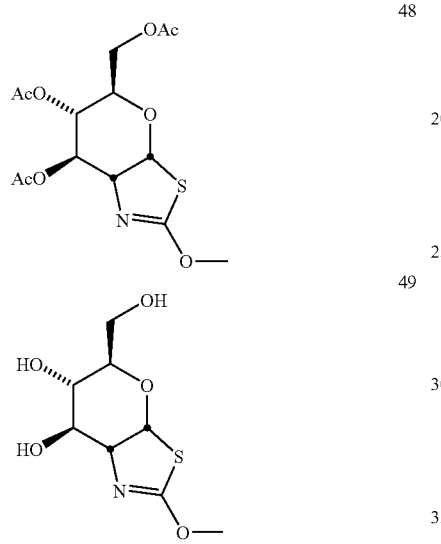

A solution of (2S,3R,4R,5S,6R)-6(acetoxymethyl)-3-isothiocyanato-tetrahydro-2H-pyran-2,4,5-triyl triacetate (1.0 g, 2.57 mmol) in anhydrous methanol (10 mL) was heated to reflux. The reaction was complete after 1 h as determined by TLC. The solvent was removed in vacuo. The product was then purified by flash column silica chromatography using a solvent system of 3:1 hexanes/EtOAc, which provided (2R,3R,4R,5S,6R)-4-(acetoxymethyl)-3-(methoxycarbonothioylamino)tetrahydro-2H-pyran-2,4,5-triyl triacetate (1.0 g, 92% yield) as a slightly yellow syrup. $^1$H NMR (500 MHz, CDCl$_3$) δ 2.11 (s, 3H), 2.12 (s, 6H), 3.81 (ddd, 1H), 3.95 (s, 3H), 4.1 (m, 2H), 4.31 (m, 1H), 5.17 (m, 2H), 5.73 (d, 1H, J=8.6 Hz), 6.21 (d, 1H, J=10.0 Hz).

The thiocarbamate from above (1.0 g, 2.37 mmol) was dissolved in anhydrous CH$_2$Cl$_2$ (10 mL) and SnCl$_4$ (2.47 g, 9.49 mmol) was added dropwise. The reaction mixture was stirred at room temperature overnight (16 h). The reaction was quenched with saturated aqueous NaHCO$_3$ until the solution was basic and no more gas was evolved. The aqueous layer was extracted three times with CH$_2$Cl$_2$. The combined organic layers were dried with MgSO$_4$, filtered and concentrated. The crude material was purified by flash chromatography (EtOAc/hexanes, 1:1), providing (3aR,5R,6S,7R,7aR)-5-(acetoxymethyl)-2-methoxy-5,6,7,7a-tetrahydro-3aH-pyrano[3,2-d]thiazole-6,7-diyl diacetate 48 (0.65 g, 76% yield) as a clear oil. $^1$H NMR (500 MHz, CDCl$_3$) δ 2.08 (s, 3H), 2.09 (s, 3H), 2.13 (s, 3H), 3.89 (ddd, 1H, J=3.7, 4.6, 9.8 Hz), 3.92 (, 3H), 4.12 (m, 2H), 4.36 (ddd, 1H, J=1.0, 4.0, 6.9 Hz), 4.96 (dd, 1H, J=1.0, 2.9, 9.4 Hz), 5.40 (dd, 1H, J=2.9, 4.0 Hz), 6.30 (d, 1H, J=6.9 Hz).

Following General Procedure C, the material obtained above was converted to the title compound 49 which was isolated as a colourless oil after purification (0.33 g, 78% yield). In this case purification was carried out using flash chromatography on silica gel (EtOAc). $^1$H NMR (500 MHz, methanol-d$_4$) δ3.45 (dd, 1H, J=5.5, 9.2 Hz), 3.56 (ddd, 1H, J=1.8, 8.7, 9.3 Hz), 3.62 (dd, 1H, J=6.1, 11.8 Hz), 3.75 (dd, 1H, J=1.7, 11.8 Hz), 3.84 (dd, 1H, J=5.7, 5.8 Hz), 3.86 (s, 3H), 4.07 (dd, 1H, J=6.2, 6.4 Hz), 6.39 (d, 1H, J=6.7 Hz).

Example 26

Compounds 50 and 51: (3aR,5R,6S,7R,7aR)-5-(azidomethyl-2-propyl-5,6,7,7a-tetrahydro-3aH-pyrano[3,2-d]thiazole-6,7-diol (50) and (3aR,5R,6S,7R,70)-5(aminomethyl)-2-propyl-5,6,7,7a-tetrahydro-3aH-pyrano[3,2-d]thiazole-6,7-diol (51)

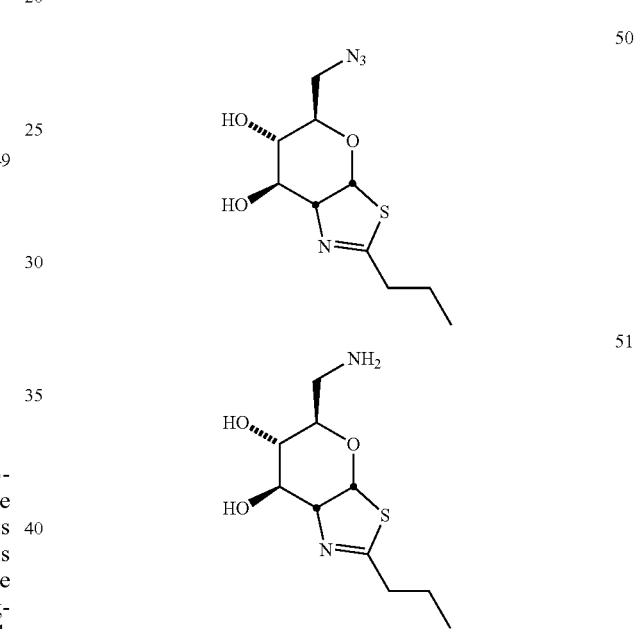

(3aR,5R,6S,7R,7aR)-5-(hydroxymethyl)-2-propyl-5,6,7,7a-tetrahydro-3aH-pyrano[3,2-d]thiazole-6,7-diol (200 mg, 0.81 mmol) was dissolved in pyridine (2 mL) and CH$_2$Cl$_2$ (2 mL) and cooled to 0° C. Tosyl chloride (230 mg, 1.2 mmol) was then added and the solution allowed to warm to room temperature over 1 h. The mixture was diluted with CH$_2$Cl$_2$ (10 mL) and washed with water (2×5 mL), dried (MgSO$_4$), filtered and concentrated. The resultant colourless residue (280 mg) was taken up in DMF (3 mL) and NaN$_3$ (158 mg, 2.4 mmol) was added. The resultant mixture was stirred at 55° C. for 2 days. Concentration of the mixture gave a residue which was taken up in CH$_2$Cl$_2$ (20 mL) and washed with water (2×5 mL), dried (MgSO$_4$), filtered and concentrated. Flash chromatography of the residue on silica gel (MeOH:EtOAc, 1:9) gave 180 mg (82% yield) of (3aR,5R,6S,7R,7aR)-5-(azidomethyl)-2-propyl-5,6,7,7a-tetrahydro-3aH-pyrano[3,2-d]thiazole-6,7-diol (50) as a colourless oil. $^1$H NMR (500 MHz, methanol-d$_4$): δ 0.98 (t, 3H, J=7.3 Hz), 1.63-1.67 (m, 2H), 2.46-2.50 (m, 2H), 3.33 (m, 1H), 3.54 (dd, 1H, J=4.3, 9.5 Hz), 3.44 (dd, 1H, 2.3, 12.0 Hz), 3.55 (dd, 1H, J=6.2, 12.0 Hz), 4.06 (dd, 1H, J=4.4, 4.6 Hz), 4.29 (m, 1H, J=4.3 Hz), 6.31 (d, 1H, J=6.9 Hz).

The azide obtained as described above (200 mg, 0.81 mmol) was dissolved in 3:1 THF:H$_2$O (5 mL) and triphenylphosphine (310 mg, 1.2 mmol) was added. The solution was then stirred overnight at room temperature. Concentration of the mixture followed by flash chromatography of the resultant residue on silica gel (MeOH:EtOAc 2:3) gave 130 mg (75% yield) of (3aR,5R,6S,7R,7aR)-5-(aminomethyl)-2-propyl-5,6,7,7a-tetrahydro-3aH-pyrano[3,2-d]thiazole-6,7-diol (51) as a colourless oil. This material was observed to decompose slowly with time when stored neat at 0° C. (7 d). $^1$H NMR (500 MHz, methanol-d$_4$): δ 0.97 (t, 3H, J=7.4 Hz), 1.63-1.67 (m, 2H), 2.43-2.49 (m, 2H), 3.39 (ddd, 1H, J=2.5, 4.1, 9.0 Hz), 3.51 (dd, 1H, J=4.1, 9.5 Hz), 3.64 (dd, 1H, J=2.5, 12.5 Hz), 3.75 (dd, 1H, J=6.1, 12.5 Hz), 4.04 (dd, 1H, J=4.4, 4.5 Hz), 4.28 (m, 1H), 6.35 (d, 1H, J=7.0 Hz).

Example 27

Assay for Determination of K$_I$ Values for Inhibition of O-GlcNAcase Activity

Experimental procedure for kinetic analyses: Enzymatic reactions were carried out in PBS buffer (pH 7.4) using pNP-GlcNAc as a substrate (0.5 mM) and monitored continuously at 37° C. at 400 nm using a Cary 3E UV-VIS spectrophotometer equipped with a Peltier temperature controller. Reactions were pre-heated in a 500 μL quartz cuvette for approximately 5 minutes followed by addition of 10 μL enzyme via syringe (final enzyme concentration 0.002 mg/mL). Reaction velocities were determined by linear regression of the linear region of the reaction progress curve between the first and third minutes. An inhibitor concentration range of ⅕ to 5 times K$_I$ was used in each case.
When tested in the assay described above, many of the compounds described in the Examples herein exhibit K$_I$ values for inhibition of O-GlcNAcase in the range 1 nM-50 μM. For example, the K$_I$ values for inhibition of O-GlcNAcase shown in Table 4 were obtained for compounds 2, 4, and 6. All K$_I$ values were determined using linear regression of a Dixon plots.

TABLE 4

Inhibition constants for O-GlcNAcase.

| Compound | O-GlcNAcase K$_I$ (μM) |
|---|---|
| 2 | 10 |
| 4 | 7.7 |
| 6 | 5.6 |

Example 28

Assay for Determination of K$_I$ Values for Inhibition of β-hexosaminidase Activity Experimental procedure for kinetic analyses: All enzymatic assays were carried out in triplicate at 37° C. using a stopped assay procedure by measuring the amount of 4-nitrophenolate liberated as determined by absorption measurements at 400 nm. Reactions (50 μL) were initiated by the addition, via syringe, of enzyme (3 μL). Time-dependent assay of β-hexosaminidase revealed that the enzyme was stable in the buffer over the period of the assay: 50 mM citrate, 100 mM NaCl, 0.1% BSA, pH 4.25. β-hexosaminidase was used at a concentration of 0.036 mg/mL with pNP-GlcNAc as a substrate at a concentration of 0.5 mM. The inhibitor was tested at five concentrations ranging from 5 times to ⅕ K$_I$. K$_I$ values were determined by linear regression of data from Dixon plots.
When tested in the assay described above, many of the compounds described in the Examples herein exhibit K$_I$ values for inhibition of β-hexosaminidase in the range 5 μM-10 mM.
The selectivity ratio for inhibition of O-GlcNAcase over β-hexosaminidase is defined here as:

$$K_{I(\beta\text{-}hexosaminidase)}/K_{I(O\text{-}GlcNAcase)}$$

In general, the compounds described in the Examples herein exhibit a selectivity ratio in the range of about 1000 to 100000. When compared, for example, to the compounds of Table 3, many of the compounds described in the Examples herein exhibit greater selectivity towards O-GlcNAcase. Thus, the compounds of the invention show exhibit high selectivity for inhibition of O-GlcNAcase over β-hexosaminidase.

Example 29

Dose-dependent Elevation of Rat Brain and Muscle O-GlcNAc Levels

The effect of intravenous (IV) administration of (3aR,5R,6S,7R,7aR)-5-(hydroxymethyl)-2-propyl-5,6,7,7a-tetrahydro-3aH-pyrano[3,2-d]thiazole-6,7-diol (Compound 54; hereinafter referred to as NAG-Bt) on levels of O-GlcNAc modification in brain and muscle tissue in Sprague-Dawley rats was measured. Animals were obtained from Charles-River as 5-week old healthy male Sprague-Dawley rats. Animals were given one week to acclimatize and at six weeks of age the appropriate treatment was initiated. Eight animals were given intravenous tail vein injections of various concentrations of NAG-Bt or vehicle alone (PBS); doses of NAG-Bt included 0, 2, 5, 10, 25, 50, 100, and 250 mg/kg. Seven hours later animals were sacrificed and tissues were removed from animals as quickly as possible to minimize post-mortem delay. Tissues were immediately frozen in liquid nitrogen and stored at −80° C. until further use. Homogenization of the tissues was carried out by manual grinding followed by homogenization in cell lysis buffer (50 mM Tris, pH 8.0, 1 mM PMSF, 0.1% NP-40, 1 mM NAG-Bt) using a tissue homogenizer (IKA) at 4° C. Insoluble cell debris was removed by centrifugation at 17,900×g for 20 minutes at 4° C. and the resulting supernatant was stored at −20° C. until use.
Western blotting of the samples thus obtained was carried out using the α-O-GlcNAc antibody (CTD110.6; Covance) and the α-actin antibody as described previously.[106] Equal amounts of homogenized brain and muscle tissue from animals treated with NAG-Bt or vehicle alone were separated by SDS-PAGE followed by probing with the primary α-O-GlcNAc antibody and an anti-IgM-mouse IgG-HRP conjugate. The resulting Western blots are shown in FIGS. 1A-F, and clearly reveal a dose-dependent elevation of O-GlcNAc levels in both brain and muscle tissue. FIGS. 1C and 1D are Western blots of samples loaded in the upper panels (FIGS. 1A and 1B) probed using anti-β-actin mAb clone AC-40 followed by an anti-mouse IgG-HRP conjugate, and reveal equivalent sample loading. Analysis of the Western blot results by densitometry (FIGS. 1E-F) reveals a more pronounced effect in brain tissue at the 250 mg/kg dose (roughly 25-fold elevation of O-GlcNAc levels over baseline) as compared to the effect in muscle tissue (roughly 10-fold elevation of O-GlcNAc levels over baseline). These results demonstrate there a dose-response for elevation of brain and muscle O-GlcNAc levels by IV administration of NAG-Bt, and that the minimum IV dose required for an observable effect in brain is roughly 5 mg/kg, under the conditions used.

Example 30

Decrease of Rat Brain Tau Phosphorylation Levels

The effect of oral administration of NAG-Bt on tau phosphorylation levels in brain tissue in Sprague-Dawley rats was measured. All animals were obtained from Charles-River as 5-week old healthy male Sprague-Dawley rats. Animals were given one week to acclimatize and at six weeks of age the appropriate treatment was initiated. Four animals were fed food containing 100 mg/kg/day of NAG-Bt for five days. Four additional animals fed with food containing no inhibitor were used as controls. At the end of five days, the animals were fasted for 11 hours, then the four animals that received NAG-Bt in food were each given an intravenous tail vein injection of 50 mg/kg NAG-Bt. All animals were fasted for a further 5 hours, then they were sacrificed and brains were removed, stored, and processed as described in Example 29.

Western blotting of the samples thus obtained was carried out using the α-O-GlcNAc antibody (CTD110.6; Covance) and a-Actin antibody as described previously.[106] For Tau blotting, pS199, pS214, pS217, pS262, pS396, and pS422 (Biosource), Tau-5 (Lab Vision; a non-PTM dependent tau antibody), Tau-1 (Chemicon; selective for nonphosphorylated Ser195, Ser198, Ser199, and Ser202), and pS404 (Sigma) antibodies were used according to the manufacturer's protocols. Equal amounts of homogenized brain tissue from an animal treated with and without NAG-Bt were separated by SDS-PAGE followed by probing with each of the primary antibodies and an appropriate secondary antibody (either an anti-mouse or anti-rabbit IgG-HRP conjugate, as appropriate). The resulting Western blots are shown in FIGS. 2A-I, and reveal decreases of brain tau phosphorylation at multiple sites following treatment with NAG-Bt; lanes labeled "+" indicate samples from animals receiving NAG-Bt while lanes labeled "−" indicate samples from animals receiving vehicle alone. Treated animals exhibit decreases in phosphorylation at the Tau-1 epitope (including Ser195, Ser198, Ser199, and Ser202), Ser199, Ser262, Ser396, Ser422, and Thr231; brain lysates probed using the Tau-5 primary antibody show equivalent sample loading. Treatment with NAG-Bt increases phosphorylation at Ser214 and Ser404, a result consistent with observations made in cultured cells using a non-selective O-GlcNAcase inhibitor.[16] Dosing with NAG-Bt essentially blocks phosphorylation of two critically important sites (Thr231 and Ser396) involved in the toxic self-assembly of tau.[116,117] These data demonstrate that oral administration of NAG-Bt has the overall effect of reducing tau phosphorylation levels in the brain.

Example 31

Elevation of Rat Cardiac O-GlcNAc Levels

The effect of intravenous (IV) administration of (3aR,5R,6S,7R,7aR)-2-(ethylamino)-5-(hydroxymethyl)-5,6,7,7a-tetrahydro-3aH-pyrano[3,2-d]thiazole-6,7-diol (Compound 25, hereinafter referred to as NAG-AE) on O-GlcNAc levels in cardiac tissue in Sprague-Dawley rats was measured. Animals were obtained from Charles-River as 5-week old healthy male Sprague-Dawley rats. Animals were given one week to acclimatize and at six weeks of age the appropriate treatment was initiated. Nine animals were given intravenous tail vein injections of 50 mg/kg NAG-AE; following injection, one animal was sacrificed at each of the following time points: 0, 1, 2, 4, 7, 10, 13, 16, and 20 h. In addition, one animal was given an injection of vehicle (PBS—pH 7.4) and sacrificed two hours later for use as a control. Tissues were removed from sacrificed animals as quickly as possible to minimize post-mortem delay. The hearts from each animal were immediately frozen in liquid nitrogen and stored at −80° C. until anther use. Homogenization of the cardiac tissue was carried out by manual grinding followed by homogenization in cell lysis buffer (50 mM Tris, pH 8.0, 1 mM PMSF, 0.1% NP-40, 1 mM NAG-Bt) using a tissue homogenizer (IKA) at 4° C. Insoluble cell debris was removed by centrifugation at 17,900×g for 20 minutes at 4° C. and the resulting supernatant was stored at −20° C. until use.

Figure 3:
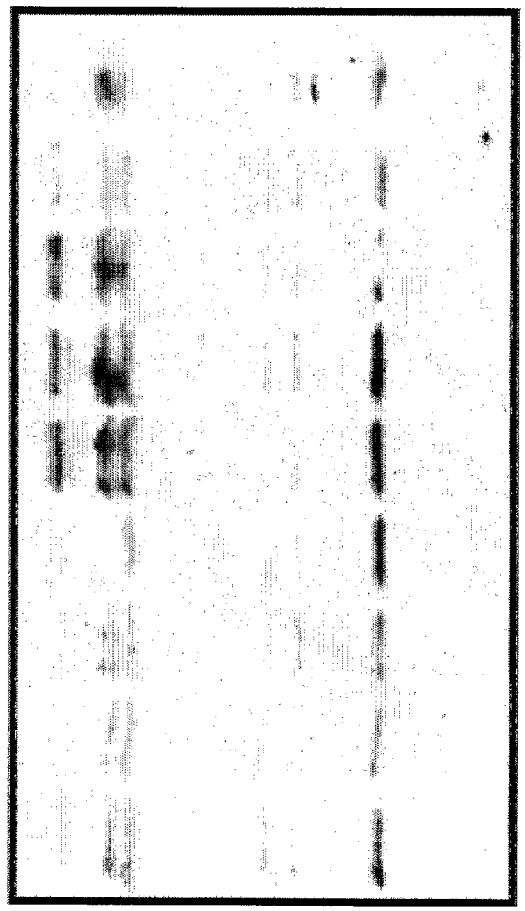
FIGS. 3A-B show Western blots of proteins from cardiac tissue of rats injected with 50 mg/kg of NAG-AE or vehicle alone (PBS) and sacrificed at various lengths of time following injection. Equal amounts of homogenized cardiac tissue from animals treated with NAG-AE for the indicated lengths of time were separated by SDS-PAGE followed by probing with the primary α-O-GlcNAc antibody and an anti-IGM-mouse IgG-HRP conjugate (A).
Figure 4:
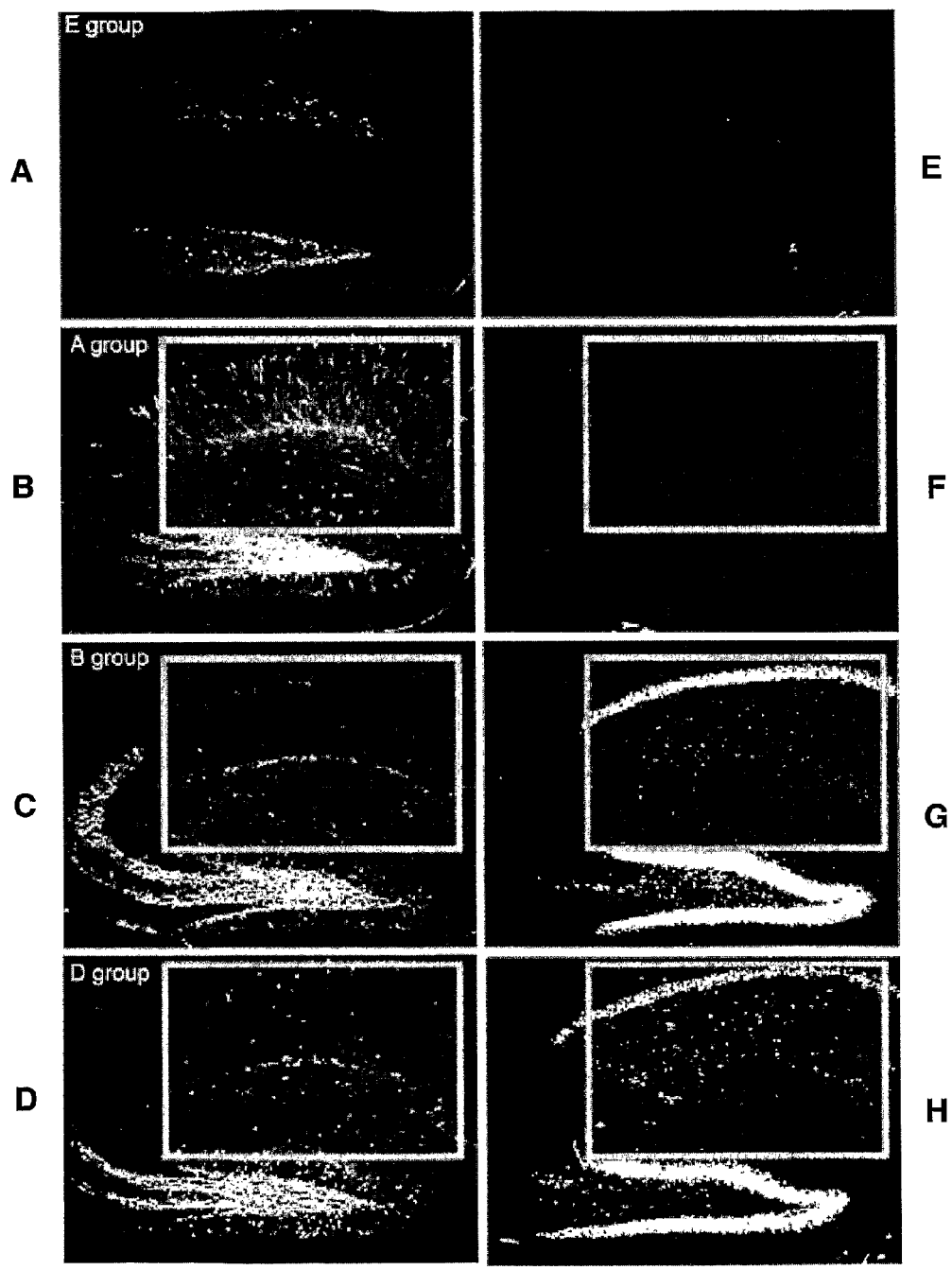
FIGS. 4A-H show stained hippocampus brain tissue sections collected from P301L JNPL3 mice, a transgenic model that develops hyperphosphorylated tau protein and NFTs. Group E are wild-type control mice that received vehicle alone; Group A are transgenic mice that received vehicle alone; Group B are transgenic mice that received 100 mg/kg/day NAG-Bt orally for 16 weeks, then 1000 mg/kg/day NAG-Bt orally for 16 weeks; Group D are transgenic mice that received 500 mg/kg/day NAG-AE orally for 16 weeks; all mice were 42-44 weeks of age at the time of sacrifice. Panels on the right (FIGS. 4E-H) show sections stained with anti-OGlcNAc antibody (a marker for protein OGlcNAc levels), while panels on the left (Figures A-D) show sections stained with anti-phospho Tau-Ser404 antibody (a marker for levels of tau phosphorylation and NFT formation). Animals receiving either NAG-Bt or NAG-AE (Groups B and D) shown elevated protein O-GlcNAc levels and significantly decreased formation of hyperphosphorylated tau and NFTs when compared to the untreated transgenic group (Group A). The boxed area in each panel indicates similar regions from each brain section in the transgenic animals, highlighted for comparative purposes.
Figure 5:
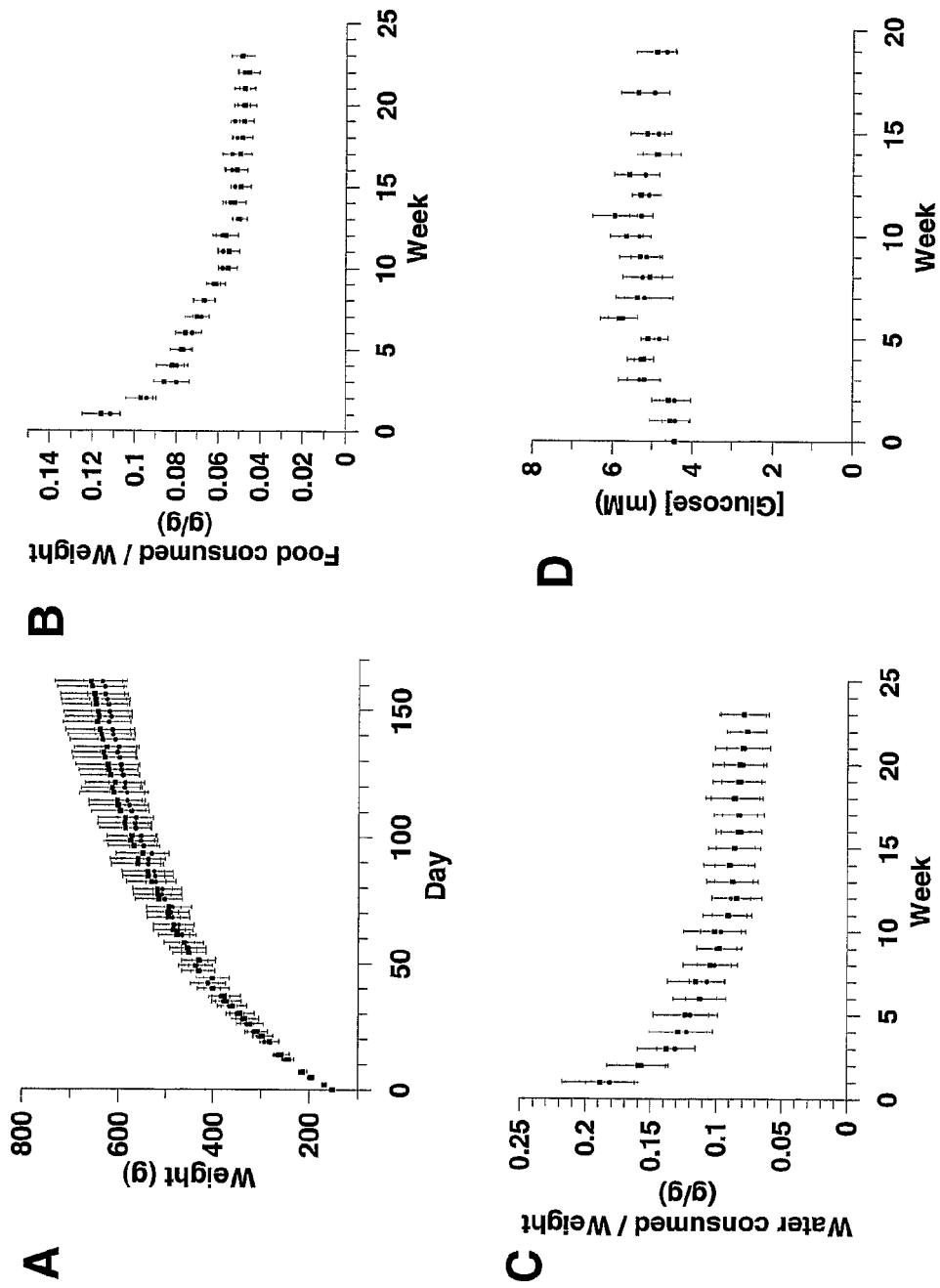
FIGS. 5A-D show long-term effects of oral dosing (100 mg/kg/day) of Sprague-Dawley rats with NAG-Bt on weight (A), food consumption (B), water consumption (C), and blood glucose levels (D) determined over four months. Data for eight control rats (squares) versus eight dosed rats (circles) are plotted on all graphs; no significant differences were noted.

Western blotting of the samples thus obtained was carried out using the α-O-GlcNAc antibody (CTD110.6; Covance) and the α-actin antibody as described previously.[106] Equal amounts of homogenized cardiac tissue from animals treated with NAG-AE for the varying lengths of time were separated by SDS-PAGE followed by probing with the primary α-O-GlcNAc antibody and an anti-IgM-mouse IgG-HRP conjugate. The resulting Western blots are shown in FIGS. 3A-B, and clearly reveal a time-dependent elevation of O-GlcNAc levels in cardiac tissue, with a maximum effect being obtained between 4 and 13 h. FIG. 3B shows a Western blot of samples loaded in the upper panel (FIG. 3A) probed using an anti-β-actin mAb clone AC-40 followed by an anti-mouse IgG-HRP conjugate, and reveals equivalent sample loading. These results demonstrate there an elevation of cardiac O-GlcNAc levels resulting from IV administration of NAG-AE. The other compounds of the invention behave in a similar manner to NAG-AE.

Example 32

Reduction of NFT Formation in Transgenic P301L JNPL3 Mice

Animal dosing and tissue collection. Hemizygous transgenic female JNPL3 mice overexpressing human mutant tau protein (P301L) and wild type control mice were obtained from Taconic Farms, Inc. (model numbers 001638-T-F and 001638-W-F, respectively). The mice were 10-12 weeks of age at delivery, designated "week 1" of the study. In week 1, the mice were split into four groups: Group A (transgenic mice) received vehicle alone throughout the study; Group B (transgenic mice) received 100 mg/kg/day NAG-Bt in their food from week 1 to week 15, then were switched to 1000 mg/kg/day NAG-Bt in their drinking water from week 16 to week 32; Group D (transgenic mice) received vehicle alone from weeks 1 to 15, and then 500 mg/kg/day NAG-AE in their drinking water from weeks 16 to 32; Group E (wild-type) received vehicle alone throughout the study. In week 32, three animals per group were sacrificed and tissues were collected. Transgenic mice and controls were sacrificed using a $CO_2$ chamber. About 45 seconds after they stopped breathing, they were perfused transcardially with 30 mL of 0.9% NaCl buffer followed by 30 mL of 4% paraformaldehyde (w/v in 1× phosphate-buffered saline, PBS, pH 7.4). The brains were then carefully dissected and post-fixed in 4% paraformaldehyde before being cryoprotected in 20% sucrose (w/v in 1×PBS) for 24 hours at 4° C.

Cryostat sectioning. The brains were then mounted with optimal cutting temperature (OCT) medium (Tissue Tek) and sectioned sagittally on a Reichert-Jung Cryocut 1800 (Leica) using Feather microtome blades (Tissue Tek) at 50 μm and placed in 1×PBS for further processing. The cryostat temperature was set at −17° C. to −19° C.

Immunohistochemical staining. Free-floating 50 μm sagittal sections (lateral about 0.6 mm from midline, Mouse Brain in Stereotaxic Coordinates, second edition, by George Paxinos and Leith B. J. Franklin) were permeabilized with 1×PBS containing 0.3% Triton X-100 for 15 min. After blocking with 10% goat serum and 2.5% BSA for 1 h at room temperature, sections were incubated with specific antibodies overnight at 4° C. primary antibodies: anti-OGlcNAc, Covance; anti-phospho Tau-ser404, Santa Cruz). The secons then were washed three times with 0.3% Triton X-100 in PBS for 15 min each and incubated with specific secondary antibody conjugated with Cy3 or FITC for 1.5 h at room temperature in the dark. After several washes in 1×PBS, sections were mounted on slides and air-dried in the dark. Once dry, Vectashield Mounting Medium (Vector Laboratories, Inc.) was added to the slide before applying coverslips. Coverslips were sealed with clear nail enamel and slides were stored in dark at 4° C. For negative control staining, sections were incubated without primary antibodies.

Imaging. Sections were visualized using a Leica fluorescent microscope (DM4000B). A filter set (excitation peak: 480 nm, emission peak: 520 nm, Leica) was used for O-GlcNAc/FITC imaging and another filter set (excitation filter: 530-550 nm, emission filter: 570 nm, Leica) was used for phospho-Tau-ser404/Cy3 imaging. 10× Images from the hippocampus regions of brains were acquired using a Spot digital camera (Diagnostic Instruments, Sterling Heights, Mich., USA).and processed with LAS (Leica Application Suite) software.

The images of hippocampal brain sections from representative mice in each group are shown in FIGS. 4A-H. The images on the right-hand side (FIGS. 4E-H) are sections stained with anti-OGlcNAc antibody, and light areas correspond to regions with high levels of protein O-GlcNAc modification. The images on the left-hand side (FIGS. 4A-D) are sections stained with anti-phospho Tau-Ser404 antibody, and light areas correspond to regions with high levels of phosphorylated tau protein; in particular, the bright dots correspond to aggregates of hyperphosphorylated tau protein, or neurofibrillary tangles (NFTs). The grey boxes highlight similar section areas for comparative purposes. It is clear that the groups receiving vehicle alone (Groups E and A, FIGS. 4E-F) exhibit low levels of protein O-GlcNAc modification, while those groups receiving either NAG-Bt or NAG-AE (Groups B and D, FIGS. 4G-H) show dramatically elevated levels of O-GlcNAc modification (right-hand panels). More striking are the differences in hyperphosphorylated tau and NFT formation between groups. As expected, the wild-type mice (Group E, FIG. 4A) show low levels of phosphorylated tau, while the untreated transgenic animals (Group A) exhibit extensive tau phosphorylation and NFT formation. However, groups receiving either NAG-Bt or NAG-AE (Groups B and I, FIGS. 4C and 4D, respectively) show dramatically reduced levels of tau phosphorylation and NFT formation compared to the untreated transgenic animals (Group A, FIG. 4B). These images provide compelling evidence that the compounds of the invention have the desired effect of reducing the unber of NFTs and overall tau phosphorylation in a murine model of Alzheimer's disease.

Example 33

Eight-month Repeat Dose Toxicology Study in Rats

The toxicological effects of repeated oral administration of (3aR,5R,6S,7R,7aR)-5-(hydroxymethyl)-2-propyl-5,6,7,7a-tetrahydro-3aH-pyrano[3,2-d]thiazole-6,7-diol (NAG-Bt) to Sprague-Dawley rats over eight months was measured. All animals were obtained from Charles-River as 5-week old healthy male Sprague-Dawley rats. Animals were given one week to acclimatize and at six weeks of age the appropriate treatment was initiated. Eight animals were fed food containing 100 mg/kg/day of NAG-Bt for eight months. Eight additional animals fed with food containing no inhibitor were used as controls. During this time, body weight, food consumption, water consumption, and blood glucose levels were monitored for animals in each group (FIGS. 5A-D, respectively; data for control rats represented by squares, data for dosed rats represented by circles); no significant differences were noted between the two groups. No gross pathological abnormalities or behavioural differences were observed in the group receiving NAG-Bt during this time. After four months of dosing, blood and urine samples were collected from four rats in each group. These samples were analyzed by hematology (CBC), serum chemistry and urinalysis (Tables 5 and 6); no statistically significant differences were detected between groups.

Table 5 shows results from hematology (CBC) and serum chemistry tests on rats dosed orally with NAG-Bt for 4 months at 100 mg/kg/day versue controls

| CBC/Serum Measurement | Untreated (n = 4 rats) | | Treated (n = 4 rats) | |
| --- | --- | --- | --- | --- |
| | average | sd | average | sd |
| Nonesterified Fatty Acids (mM) | 1.8 | 0.6 | 1.8 | 0.8 |
| Red cell cnt(L-1) | 9.3 | 1.0 | 10.1 | 0.7 |
| White cell cnt (1e9/l) | 4.5 | 1.7 | 3.8 | 0.8 |
| Lymphs % | 88.3 | 3.3 | 82.3 | 6.8 |
| Monocytes % | 4.3 | 2.2 | 4.3 | 1.9 |
| Polys % | 7.5 | 2.4 | 10.8 | 5.0 |
| Hemoglobin (g/L) | 157.8 | 13.4 | 169.5 | 10.3 |
| Hematocrit (l/l) | 0.5 | 0.0 | 0.5 | 0.0 |
| Mean Corp Vol. (fL) | 53.8 | 1.5 | 53.3 | 1.3 |
| Mean Corp Hemoglobin (pg) | 16.9 | 0.6 | 16.9 | 0.6 |
| Mean Corp Hemoglobin Conc. (g/l) | 314.5 | 6.0 | 318.5 | 4.4 |
| RDW | 16.6 | 1.5 | 17.4 | 0.8 |
| Platelet cnt (10e9/L) | 441.8 | 173.0 | 561.8 | 360.0 |
| Mean Platelet Vol (fL) | 11.5 | 2.1 | 9.3 | 2.3 |
| Glucose (mM) | 1.9 | 0.6 | 2.0 | 1.0 |
| Blood Urea Nitrogen (mM) | 8.1 | 2.4 | 8.9 | 0.8 |
| Creatinine (uM) | 23.8 | 11.0 | 29.0 | 9.1 |
| Sodium (mM) | 147.0 | 0.8 | 145.8 | 2.1 |

Table 6 shows results from urinalysis tests on rats dosed orally with NAG-Bt for 4 months at 100 mg/kg/day versus controls

|  | Untreated (n = 4 rats) | | Treated (n = 4 rats) | |
|---|---|---|---|---|
| CBC/Serum Measurement | average | sd | average | sd |
| Potassium (mM) | 6.4 | 0.6 | 5.9 | 0.6 |
| Calcium (mM) | 2.7 | 0.0 | 2.7 | 0.1 |
| Phosphorus (mM) | 2.3 | 0.2 | 2.2 | 0.2 |
| Total Protein (g/l) | 78.0 | 2.7 | 78.0 | 4.5 |
| Albumin (g/l) | 49.8 | 1.5 | 47.8 | 4.7 |
| Globulin (g/l) | 28.3 | 2.5 | 30.3 | 1.0 |
| Albumin/Globulin | 1.8 | 0.2 | 1.6 | 0.2 |
| Bilirubin total (uM) | 0.0 | 0.0 | 0.0 | 0.0 |
| Alkaline phsphatase (iu/l) | 152.5 | 28.2 | 168.3 | 27.8 |
| AST (iu/l) | 255.8 | 56.2 | 202.3 | 37.9 |
| Gamma gt (iu/l) | 12.0 | 4.3 | 17.5 | 4.2 |
| Chloride (mM) | 106.0 | 0.0 | 104.5 | 1.9 |
| Carbon Dioxide (mM) | 15.8 | 1.3 | 17.5 | 1.3 |
| Osmolality (mmol/kg) | 295.3 | 3.5 | 292.9 | 3.4 |
| Anion Gap | 31.8 | 1.7 | 29.8 | 2.2 |
| Creating Phosphokinase (iu/l) | 1591.0 | 325.5 | 1324.5 | 321.6 |
| ALT (iu/l) | 124.3 | 29.5 | 109.3 | 18.4 |
| Sorbitol Dehydrogenase (iU/L) | 15.8 | 7.6 | 22.3 | 7.3 |
| Cholesterol (mM) | 1.9 | 0.3 | 2.9 | 0.6 |
| Triglyceride (mM) | 1.8 | 0.5 | 2.7 | 1.4 |

| Urine Measurement | Untreated (−) | | | | Treated (+) | | |
|---|---|---|---|---|---|---|---|
| SP. GRV. | 1.06 | 1.05 | 1.05 | 1.05 | 1.042 | 1.046 | 1.036 |
| Appear | Clear | Slcld | Clear | Slcld | Turbid | Turbid | Clear |
| Color | Yellow | Yellow | Pale | Yellow | Yellow | Yellow | Yellow |
| Protein (g/L) | Trace | 1 | Trace | Trace | 1 | neg | neg |
| Glucose | neg | neg | neg | neg | neg | neg | neg |
| Blood | 2+ | trace | neg | 1+ | 2+ | neg | 2+ |
| Bilirubin | neg | neg | neg | neg | neg | neg | neg |
| Urobil | Norm | Norm | Norm | Norm | Norm | Norm | Norm |
| WBC | 0-3 | 0-3 | neg | neg | 0-3 | neg | neg |
| RBC | 6.0-10 | 0-3 | 0-3 | 0-3 | 0-3 | 0-3 | neg |
| Epith | Few | Few | Few | neg | neg | neg | neg |
| Hyal cast | neg | neg | neg | neg | neg | neg | neg |
| Gran Cast | neg | neg | neg | neg | neg | neg | neg |
| RBC Cast | neg | neg | neg | neg | neg | neg | neg |
| Bacteria | neg | neg | neg | neg | Moderate | neg | neg |
| Mucus | neg | few | neg | neg | neg | few | neg |
| Crystals | PO4 | PO4 | PO4 | PO4 | PO4 | PO4 | |
| Amount | Many | Moderate | Few | Many | Many | Many | |

Figure 6:
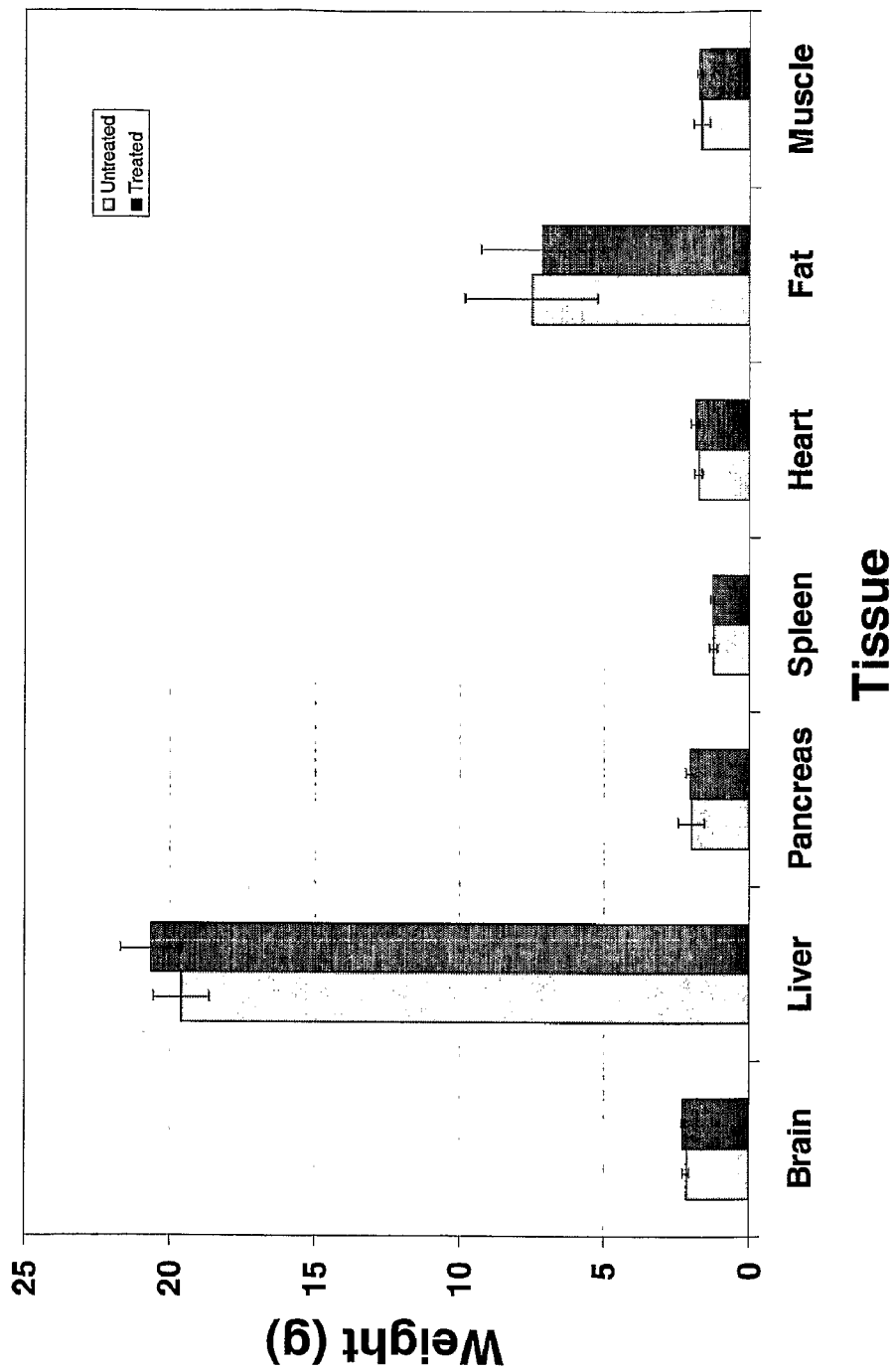
FIG. 6 is a bar graph showing results for organ weight measurements (brain, liver, pancreas, spleen, heart, fat muscle) on rats dosed orally with NAG-Bt for 8 months at 100 mg/kg/day versus controls. Measurements were made on 6 rats per group, which were averaged. No significant differences were observed.

Notably, no changes in ALT, AST, bilirubin or sorbitol dehydrogenase were observed in the dosed group, indicating the absence of liver toxicity. At the end of eight months, all animals were sacrificed and their organs removed and weighed. Organ weights (brain, liver, pancreas, spleen, heart, fat, muscle) for 6 animals from each group are shown in FIG. 6; no significant differences were observed between groups. These results indicate that there are no serious toxicological consequences resulting from long-term dosing of NAG-Bt in rats. This evidence supports the use of the compounds of the invention in humans to safely treat disease conditions responsive to modulation of protein O-GlcNAc levels; specifically, these data indicate the compounds of the invention have a suitable safety profile to be used for therapeutic purposes.

Example 34

Decrease of Rat Brain Tau Phosphorylation Levels

The effect of oral administration of (3aR,5R,6S,7R,7aR)-2-(ethylamino)-5-(hydroxymethyl)-5,6,7,7a-tetrahydro-3aH-pyrano[3,2-d]thiazole-6,7-diol (Compound 25, NAG-AE) on tau phosphorylation levels in brain tissue in Sprague-Dawley rats was measured. All animals were obtained from Charles-River as 5-week old healthy male Sprague-Dawley rats. Animals were given one week to acclimatize and at six weeks of age the appropriate treatment was initiated. Three animals received 200 mg/kg/day of NAG-AE in their drinking water for one day. Three additional animals received drinking water containing no NAG-AE and were used as controls. Immediately following the dosing period, all animals were sacrificed and brains were removed, stored, and processed as described in Example 29.

Western Blots. Samples were separated through 10% sodium dodecyl sulfate polyacrylamide gels (SDS-PAGE) and then transferred to nitrocellulose (Bio-Rad) membranes. Memlbranes were then blocked for 1 h at room temperature (RT) with 1% bovine serum albumin (BSA) in PBS containing 0.1% Tween-20 (Sigma) (PBS-T) and then subsequently probed with appropriate primary antibody delivered in 1% BSA in PBS-T for either 1 h at RT or overnight at 4° C. Membranes were then extensively washed with PBS-T, blocked again for 30 min with 1% BSA in PBS-T at RT and then probed with the appropriate HRP conjugated secondary antibody for 1 h at RT delivered in 1% BSA in PBS-T. Finally, the membranes were washed extensively and then developed with SuperSignal West Pico Chemiluminesence substrate (Pierce) and exposed to CL-XPosure Film (Pierce).

Antibodies. Mouse monoclonal α-Tau-5 which recognizes the central region of tau in a phosphorylation state independent manner was purchased from Lab Vision Corporation and used at a dilution of 1:500. Rabbit polyclonal α-Tau [$pS^{231}$], α-Tau [$pT^{396}$], and α-Tau [$pS^{422}$] recognize phosphorylated Thr-231, Ser-396, and Ser-422 respectively, and were purchased from Biosource International and used at a dilution of 1:1000. Mouse monoclonal α-O-GlcNAc (CTD110.6) which recognizes the O-GlcNAc monosaccharide modification was purchased from Covance and used at a dilution of 1:2500. Mouse monoclonal α-actin (clone AC-40) was purchased from Sigma and was used at a dilution of 1:1000.

Figure 7:
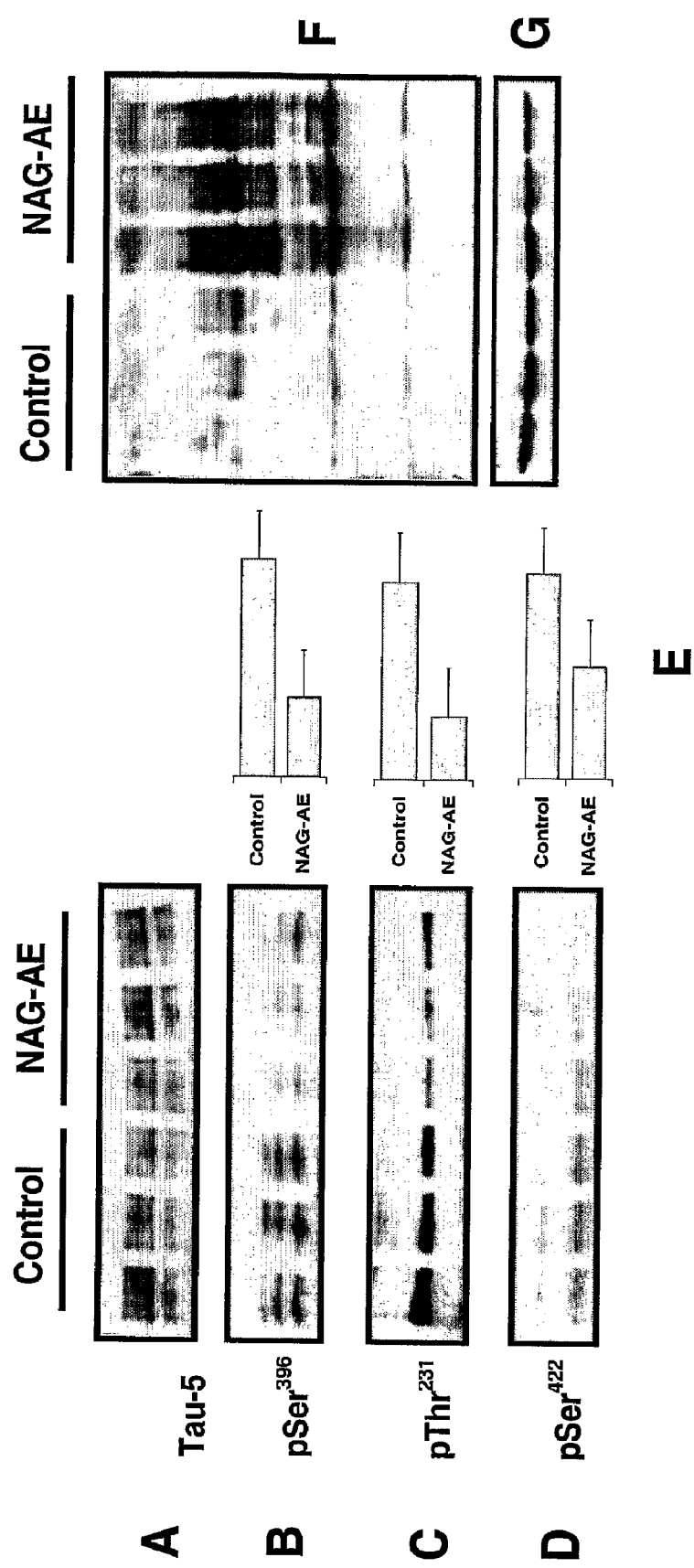
FIGS. 7A-G show Western blots of proteins from brain tissue of rats treated orally with NAG-AE (200 mg/kg/day in drinking water) or with vehicle alone (normal drinking water, 0 mg/kg/day), showing decreases in brain tau phosphorylation at multiple sites following treatment, as well as global increases in protein O-GlcNAc levels. Equal amounts of homogenized brain tissue from animals treated with and without NAG-AE (3 animals each) were separated by SDS-PAGE followed by probing with each of the primary antibodies and an appropriate secondary antibody.

As can be seen in FIGS. 7B-D, treatment of healthy rats with NAG-AE causes a reduction in tau phosphorylation at Ser-396, Thr-231, and Ser-422, respectively. By densitometry the phosphorylation at these residues is reduced by ~3.1, ~2.7 and ~1.8-fold respectively (FIG. 7E). Western blots with the Tau-5 antibody demonstrates that there is an equal amount of total tau protein in each lane (FIG. 7A) and thus the observed differences between groups cannot be attributed to differences in total tau loading. These same samples were then immunoblotted with an O-GlcNAc specific antibody which reveals that the global levels of O-GlcNAc are increased in the NAG-AE treated animals, as shown in FIG. 7F. FIG. 7G shows a Western blot of samples loaded in the upper panel (FIG. 7F) probed using an anti-β-actin mAb antibody, and reveals equivalent sample loading.

Example 35

Nine-month Repeat Dose Toxicology Study in Mice

The toxicological effects of repeated oral administration of (3aR,5R,6S,7R,7aR)-5-(hydroxymethyl)-2-propyl-5,6,7,7a-tetrahydro-3aH-pyrano[3,2-d]thiazole-6,7-diol (NAG-Bt) and (3aR,5R,6S,7R,7aR)-2-(ethylamino)-5-(hydroxymethyl)-5,6,7,7a-tetrahydro-3aH-pyrano[3,2-d]thiazole-6,7-diol (NAG-AE) to wild-type JNPL3 mice over nine months was measured. All animals were obtained from Taconic Farms, Inc. (model number 001638-W-F), and were 10-12 weeks of age at delivery, designated "week 1" of the study. In week 1, the mice were split into three groups: Group E received vehicle alone throughout the study, Group F1 received 100 mg/kg/day NAG-Bt in their food from week 1 to week 15, then were switched to 500 mg/kg/day NAG-AE in their drinking water from week 16 to week 40; Group F2 received 100 mg/kg/day NAG-Bt in their food from week 1 to week 15 then were switched to 1000 mg/kg/day NAG-Bt in their drinking water from week 16 to week 40. During this time, body weight, food consumption, and water consumption were monitored for animals in each group; no significant differences were noted between groups. No gross pathological abnormalities or behavioural differences were observed in the groups receiving NAG-Bt or NAG-AE during this time. In week 40, blood and urine samples were collected from animals in each group; the urine samples for animals in each group were pooled prior to analysis, while the blood samples were analyzed individually. These samples were analyzed by hematology (CBC), serum chemistry and urinalysis (Tables 7 and 8); no statistically significant differences were detected between groups.

Table 7 shows results from hematology (CBC) and serum chemistry tests on mice dosed orally with NAG-Bt or NAG-AE for nine months versus controls

| CBC/Serum Measurement | Group E Untreated (−) (n = 4 mice) | | Group F2 NAG-Bt treated (n = 2 mice) | | Group F1 NAG-AE treated (n = 4 mice) | |
|---|---|---|---|---|---|---|
|  | average | sd | average | sd | average | sd |
| Hematology |  |  |  |  |  |  |
| White cell cnt (1e9/L) | 3.3 | 1.3 | 1.8 | 0.3 | 3.0 | 0.9 |
| Differential |  |  |  |  |  |  |
| Eosinophils % | 0 | — | 3 | 3 | 2 | 3 |
| Neutrophils % | 7 | 3 | 37 | 33 | 6 | 3 |
| Lymphocytes % | 91 | 3 | 52 | 32 | 86 | 6 |
| Monocytes % | 3 | 3 | 8 | 2 | 6 | 2 |
| Morphology |  |  |  |  |  |  |
| Platelets | adequate |  | adequate |  | adequate |  |
| RBC Morph | normal |  | normal |  | normal |  |
| Manual pcv L/L | 0.45 | 0.01 | 0.42 | 0.02 | 0.44 | 0.02 |
| Chemistry |  |  |  |  |  |  |
| Glucose (mM) | 0.8 | — | 1.5 | 0.2 | 1.3 | 0.9 |
| Blood Urea Nitrogen (mM) | 7 | 3 | 6.3 | 0.2 | 6 | 3 |
| Creatinine (uM) | 35 | 24 | 6.2 | 0.4 | 13 | 6 |
| Bun/Cr Ratio | 87 | 59 | 256 | 9 | 114 | 68 |
| Sodium (mM) | 122 | 25 | 136 | 24 | 148 | 13 |
| Potassium (mM) | 13 | 2 | 13 | 2 | 15 | 4 |
| Na/K Ratio | 9.0 | 0.7 | 10.5 | 0.5 | 11 | 2 |
| Chloride (mM) | 89 | 20 | 100 | 17 | 112 | 13 |
| Carbon Dioxide (mM) | 0.6 | 0.3 | 0.75 | 0.05 | 1.3 | 0.7 |
| Anion Gap | 46 | 7 | 49 | 9 | 50 | 4 |
| Calcium (mM) | 2.6 | 0.2 | 2.5 | 0.1 | 2.4 | 0.2 |

-continued

| CBC/Serum Measurement | Group E Untreated (−) (n = 4 mice) | | Group F2 NAG-Bt treated (n = 2 mice) | | Group F1 NAG-AE treated (n = 4 mice) | |
|---|---|---|---|---|---|---|
| | average | sd | average | sd | average | sd |
| Phosphorus (mM) | 7 | 3 | 6.2 | 1.6 | 6.7 | 1.3 |
| Total Protein (g/L) | 70 | 33 | 72 | 3 | 76 | 5 |
| Albumin (g/L) | 29 | 13 | 33 | 11 | 38 | 8 |
| Globulin (g/L) | 41 | 20 | 39 | 9 | 38 | 11 |
| Albumin/Globulin Ratio | 0.8 | 0.2 | 1 | 0.5 | 1.3 | 0.8 |
| Alkaline phsphatase (IU/L) | 54 | 31 | 70 | 13 | 116 | 43 |
| AST (IU/L) | 272 | 136 | 250 | 93 | 201 | 62 |
| Gamma gt (IU/L) | 37 | 25 | 39 | 15 | 30 | 9 |
| Creatine Phosphokinase (IU/L) | 2448 | 1236 | 1452 | 776 | 1981 | 1229 |
| Osmolality (mmol/kg) | 204 | — | 286 | 48 | 142 | 143 |
| ALT (IU/L) | 18 | 1.3 | 26 | 11 | 15 | 1 |
| Sorbitol Dehydrogenase (IU/L) | 297 | 24 | 184 | 71 | 234 | 99 |

Table 8 shows results from urinalysis tests on mice dosed orally with NAG-Bt or NAG-AE for nine months versus controls

| Urine Measurement | Group E Untreated (—) (n = 3 mice, pooled) | Group F2 Treated (NAG-Bt) (n = 2 mice, pooled) | Group F1 Treated (NAG-AE) (n = 3 mice, pooled) |
|---|---|---|---|
| Sp. Grv. | 1.050 | 1.05 | 1.039 |
| Appear | Clear | Clear | Slcloudy |
| Color | Yellow | Yellow | Yellow |
| Protein (g/L) | Neg | Neg | Neg |
| Glucose | Neg | Neg | Neg |
| Ketones | Neg | Neg | Neg |
| Blood | 4+ | NSQ | Neg |
| Bilirubin | Neg | Neg | Neg |
| Urobil | Normal | Normal | Normal |
| WBC | 0-3 | Neg | Neg |
| RBC | 6-10 | Neg | Neg |
| Epith | Few | Few | Few |
| Rods | Neg | Neg | Neg |
| Cocci | Neg | Neg | Neg |
| pH | 5 | 5 | 6 |
| Urine Creatinine | 5693.6 | 7790.9 | 3105.4 |

Notably, no changes in ALT, AST, or sorbitol dehydrogenase were observed in the dosed group, indicating the absence of liver toxicity. These results indicate that there are no serious toxicological consequences resulting from long-term dosing of NAG-Bt or NAG-AE in mice at comparatively high levels. This evidence supports the use of the compounds of the invention in humans to safely treat disease conditions responsive to modulation of protein O-GlcNAc levels; specifically, these data indicate the compounds of the invention have a suitable safety profile to be used for therapeutic purposes.

The present invention has been described with regard to one or more embodiments. However, it will be apparent to persons skilled in the art that a number of variations and modifications can be made without departing from the scope of the invention as defined in the claims.

REFERENCES

1. C. R. Torres, G. W. Hart, *J Biol Chem* 1984, 259, 3308.
2. R. S. Haitiwanger, G. D. Holt, G. W. Hart, *J Biol Chem* 1990, 265, 2563.
3. L. K. Kreppel, M. A. Blomberg, G. W. Hart, *J Biol Chem* 1997, 272, 9308.
4. W. A. Lubas, D. W. Frank, M. Krause, J. A. Hanover, *J Biol Chem* 1997, 272, 9316.
5. W. A. Lubas, J. A. Hanover, *J Biol Chem* 2000, 275, 10983.
6. D. L. Dong, G. W. Hart, *J Biol Chem* 1994, 269, 19321.
7. Y. Gao, L. Wells, F. L. Comer, G. J. Parker, G. W. Hart, *J Biol Chem* 2001, 276, 9838.
8. E. P. Roquemore, M. R. Chevier, R. J. Cotter, G. W. Hart, *Biochemistry* 1996, 35, 3578.
9. S. P. Jackson, R. Tjian, *Cell* 1988, 55, 125.
10. W. G. Kelly, M. E. Dahmus, G. W. Hart, *J Biol Chem* 1993, 268, 10416.
11. M. D. Roos, K. Su, J. R. Baker, J. E. Kudlow, *Mol Cell Biol* 1997, 17, 6472.
12. N. Lamarre-Vincent, L. C. Hsieh-Wilson, *J Am Chem Soc* 2003, 125, 6612.
13. F. Zhang, K. Su, X. Yang, D. B. Bowe, A. J. Paterson, J. B. Kudlow, *Cell* 2003, 115, 715.
14. K. Vosseller, L. Wells, M. D. Lane, G. W. Hart, *Proc Natl Acad Sci USA* 2002, 99, 5313.
15. W. A. Lubas, M. Smith, C. M. Starr, J. A. Hanover, *Biochemistry* 1995, 34, 1686.
16. L. S. Griffith, B. Schmitz, *Biochem Biophys Res Commun* 1995, 213, 424.
17. R. N. Cole, G. W. Hart, *J Neurochem* 1999, 73, 418.
18. I. Braidman, M. Carroll, N. Dance, D. Robinson, *Biochem J* 1974, 143, 295.
19. R. Ueno, C. S. Yuan, *Biochim Biophys Acta* 1991, 1074, 79.

20. C. Toleman, A. J. Paterson, T. R. Whisenhunt, J. B. Kudlow, *J Biol Chem* 2004.
21. F. Liu, K. Iqbal, I. Grundke-Iqbal, G. W. Hart, C. X. Gong, *Proc Natl Acad Sci USA* 2004, 101, 10804.
22. T. Y. Chou, G. W. Hart, *Adv Exp Med Biol* 2001, 491, 413.
23. M. Goedert, M. G. Spillantini, N. J. Cairns, R. A. Crowther, *Neuron* 1992, 8, 159.
24. M. Goedert, M. G. Spillantini, R. Jakes, D. Rutherford, R. A. Crowther, *Neuron* 1989, 3, 519.
25. E. Kopke, Y. C. Tung, S. Shaih, K C. Alonso, K. Iqbal, I. Grundke-Iqbal, *J Biol Chem* 1993, 268, 24374.
26. H. Ksiezak-Reding, W. K. Liu, S. H. Yen, *Brain Res* 1992, 597, 209.
27. B. Henrissat, A. Bairoch, *Biochem J* 1996, 316 (Pt 2), 695.
28. B. Henrissat, A. Bairoch, *Biochem J* 1993, 293 (Pt 3), 781.
29. C. X. Gong, F. Liu, L Grundke-Iqbal, K. Iqbal, *J Neural Transm* 2005, 112, 813.
30. K. Iqbal, C. Alonso Adel, E. El-Akkad, C. X. Gong, N. Haque, S. Khatoon, I. Tsujio, I. Grundke-Iqbal, *J Neural Transm Suppl* 2002, 309.
31. K. Iqbal, C. Alonso Adel, E. El-Akkad, C. X. Gong, N. Haque, S. Khatoon, J. J. Pei, H. Tanimukai, I. Tsujio, et al., *J Mol Neurosci* 2003, 20, 425.
32. W. Noble, E. Planel, C. Zehr, V. Olm, J. Meyerson, F. Suleman, K. Gaynor, L. Wang, J. LaFrancois, et al., *Proc Natl Acad Sci U S A* 2005, 102, 6990.
33. S. Le Corre, H. W. Klafki, N. Plesnila, G. Hubinger, A. Obenneier, H. Sahagun, B. Monse, P. Seneci, J. Lewis, et al., *Proc Natl Acad Sci U S A* 2006, 103, 9673.
34. S. J. Liu, J. Y. Zhang, H. L. Li, Z. Y. Fang, Q. Wang, H. M. Deng, C. X. Gong, I. Grundke-Iqbal, K. Iqbal, et al., *J Biol Chem* 2004, 279, 50078.
35. G. Li, H. Yin, J. Kuret, *J Biol Chem* 2004, 279, 15938.
36. T. Y. Chou, G. W. Hart, C. V. Dang, *J Biol Chem* 1995, 270, 18961.
37. X. Cheng, G. W. Hart, *J Biol Chem* 2001, 276, 10570.
38. X. Cheng, R. N. Cole, J. Zaia, G. W. Hart, *Biochemistry* 2000, 39, 11609.
39. L. S. Griffith, B. Schmitz, *Eur J Biochem* 1999, 262, 824.
40. K. Kamemura, G. W. Hart, *Prog Nucleic Acid Res Mol Biol* 2003, 73, 107.
41. L. Wells, L. K. Kreppel, F. I. Comer, B. E. Wadzinski, G. W. Hart, *J Biol Chem* 2004, 279, 38466.
42. L. Bertram, D. Blacker, K. Mullin, D. Keeney, J. Jones, S. Basu, S. Yhu, M. G. McInnis, R. C. Go, et al., *Science* 2000, 290, 2302.
43. S. Hoyer, D. Blum-Degen, H. G. Bernstein, S. Engelsberger, J. Humrich, S. Laufer, D. Muschner, A. Thalheimer, A. Turk, et al., *Journal of Neural Transmission* 1998, 105, 423.
44. C. X. Gong, F. Liu, 1. Grundke-Iqbal, K. Iqbal, *Journal of Alzheimers Disease* 2006, 9, 1.
45. W. J. Jagust, J. P. Seab, R. H. Huesman, P. E. Valk, C. A. Mathis, B. R. Reed, P. G. Coxson, T. F. Budinger, *Journal of Cerebral Blood Flow and Metabolism* 1991, 11, 323.
46. S. Hoyer, *Experimental Gerontology* 2000, 35, 1363.
47. S. Hoyer, in *Frontiers in Clinical Neuroscience: Neurodegeneration and Neuroprotection*, Vol. 541, 2004, pp. 135.
48. R. N. Kalaria, S. I. Harik, *Journal of Neurochemistry* 1989, 53, 1083.
49. I. A. Simpson, K. R. Chundu, T. Davieshill, W. G. Honer, P. Davies, *Annals of Neurology* 1994, 35, 546.
50. S. M. de la Monte, J. R. Wands, *Journal of Alzheimers Disease* 2005, 7, 45.
51. X. W. Zhu, G. Perry, M. A. Smith, *Journal of Alzheimers Disease* 2005, 7, 81.
52. J. C. de la Torre, *Neurological Research* 2004, 26, 517.
53. S. Marshall, W. T. Garvey, R. R. Traxinger, *Faseb J* 1991, 5, 3031.
54. S. P. Iyer, Y. Akimoto, G. W. Hart, *J Biol Chem* 2003, 278, 5399.
55. K. Brickley, M. J. Smith, M. Beck, F. A. Stephenson, *J Biol Chem* 2005, 280, 14723.
56. S. Knapp, C. H. Yang, T. Haimowitz, *Tetrahedron Letters* 2002, 43, 7101.
57. S. P. Iyer, G. W. Hart, *J Biol Chem* 2003, 278, 24608.
58. M. Jinek, J. Rehwinkel, B. D. Lazarus, E. Izaurralde, J. A. Hanover, E. Conti, *Nat Struct Mol Biol* 2004, 11, 1001.
59. K. Kamemura, B. K. Hayes, F. I. Corner, G. W. Hart, *J Biol Chem* 2002, 277, 19229.
60. Y. Deng, B. Li, F. Liu, K. Iqbal, r. Grmndke-Iqbal, R. Brandt, C.-X. Gong, *FASEB J.* 2007, fj.07.
61. L. F. Lau, J. B. Schachter, P. A. Seymour, M. A. Sanner, *Curr Top Med Chem* 2002, 2, 395.
62. P. Bounelis, J. Liu, Y. Pang, J. C. Chatham, R. B. Marchase, *Shock* 2004, 21 170 Suppl. 2, 58.
63. N. Fulop, V. Champattanachal, R. B. Marchase, J. C. Chatham, *Circulation Research* 2005, 97, E28.
64. J. Liu, R. B. Marchase, J. C. Chatham, *Faseb Journal* 2006, 20, A317.
65. R. Marchase, P. Bounelis, J. Chatham, I. Chaudry, Y. Pang, PCT Int. Appl. WO 2006016904 2006.
66. N. Fulop, P. P. Wang, R. B. Marchase, J. C. Chatham, *Journal of Molecular and Cellular Cardiology* 2004, 37, 286.
67. N. Fulop, P. P. Wang, R. B. Marchase, J. C. Chatham, *Faseb Journal* 2005, 19, A689.
68. J. Liu, R. B. Marchase, J. C. Chatham, *Journal of Molecular and Cellular Cardiology* 2007, 42, 177.
69. L. G. Not, C. A. Brocks, N. Fulop, R. B. Marchase, J. C. Chatham, *Faseb Journal* 2006, 20, A1471.
70. S. L. Yang, L. Y. Zou, P. Bounelis, I. Chaudry, J. C. Chatham, R. B. Marchase, *Shock* 2006, 25, 600.
71. L. Y. Zou, S. L. Yang, P. Bounelis, I. H. Chaudry, J. C. Chatham, R. B. Marchase, *Faseb Journal* 2005, 19, A1224.
72. R. B. Marchase, J. Liu, L. Y. Zou, V. Champattanachai, Y. Pang, N. Fulop, P. P. Wang, S. L. Yang, P. Bounelis, et al., *Circulation* 2004, 110, 1099.
73. J. Liu, Y. Pang, T. Chang, P. Bounelis, J. C. Chatham, R. B. Marchase, *Journal of Molecular and Cellular Cardiology* 2006, 40, 303.
74. J. Liu, J. C. Chatham, R. B. Marchase, *Faseb Journal* 2005, 19, A691.
75. T. Nagy, V. Champattanachai, R. B. Marchase, J. C. Chatham, *American Journal of Physiology-Cell Physiology* 2006, 290, C57.
76. N. Fulop, R. B. Marchase, J. C. Chatham, *Cardiovascular Research* 2007, 73, 288.
77. T. Lefebvre, C. Guinez, V. Dehennaut, O. Beseme-Dekeyser, W. Morelle, J. C. Michalski, *Expert Review of Proteomics* 2005, 2, 265.
78. L. Wells, K. Vosseller, G. W. Hart, *Science* 2001, 291, 2376.
79. J. A. Hanover, *FASEB J* 2001, 15, 1865.
80. D. A. McClain, W. A. Lubas, R. C. Cooksey, M. Hazel, G. J. Parker, D.C. Love, J. A. Hanover, *Proc Natl Acad Sci USA* 2002, 99, 10695.
81. P. J. Yao, P. D. Coleman, *J Neurosci* 1998, 18, 2399.
82. W. H. Yang, J. E. Kim, H. W. Nam, I. W. Ju, H. S. Kim, Y. S. Kim, J. W. Cho, *Nature Cell Biology* 2006, 8, 1074.
83. B. Triggs-Raine, D. J. Mahuran, R. A. Gravel, *Adv Genet.* 2001, 44, 199.

84. D. Zhou, J. Mattner, C. Cantu Iii, N. Schrantz, N. Yin, Y. Gao, Y. Sagiv, K. Hudspeth, Y. Wu, et al., *Science* 2004.
85. G. Legler, E. Lullau, E. Kappes, F. Kastenholz, *Biochim Biophys Acta* 1991, 1080, 89.
86. M. Horsch, L. Hoesch, A. Vasella, D. M. Rast, *Eur J Biochem* 1991, 197, 815.
87. J. Liu, A. R. Shilhinan, M. K. Lotz, C. H. Wong, *Chem Biol* 2001, 8, 701.
88. S. Knapp, D. J. Vocadlo, Z. N. Gao, B. Kirk, J. P. Lou, S. G. Withers, *J. Am. Chem. Soc.* 1996, 118, 6804.
89. V. H. Lillelund, H. H. Jensen, X. Liang, M. Bols, *Chem Rev* 2002, 102, 515.
90. R. J. Konrad, I. Mikolaenko, J. F. Tolar, K. Liu, J. E. Kudlow, *Biochem J* 2001, 356, 31.
91. K. Liu, A. J. Paterson, F. Zhang, J. McAndrew, K, Fukuchi, J. M. Wyss, L. Peng, Y. Hu, J. E. Kudlow, *J Neurochem* 2004, 89, 1044.
92. G. Parker, R. Taylor, D. Jones, D. McClain, *J Biol Chem* 2004, 279, 20636.
93. E. B. Arias, J. Kim, G. D. Cartee, *Diabetes* 2004, 53, 921.
94. A. Junod, A. E. Lambert, L. Orci, R. Pictet, A. E. Gonet, A. E. Renold, *Proc Soc Exp Biol Med* 1967, 126, 201.
95. R. A. Benmett, A. E. Pegg, *Cancer Res* 1981, 41, 2786.
96. K. D. Kroncke, K. Fehsel, A. Sommer, M. L. Rodriguez, V. Kolb-Bachofen, *Biol Chem Hoppe Seyler* 1995, 376, 179.
97. H. Yamamoto, Y. Uchigata, H. Okamoto, *Nature* 1981, 294, 284.
98. K. Yamada, K. Nonaka, T. Hanafisa, A. Miyazaki, H. Toyoshima, S. Tami, *Diabetes* 1982, 31, 749.
99. V. Burkart, Z. Q. Wang, J. Radons, B. Heller, Z. Herceg, L. Stingl, E. F. Wagner, H. Kolb, *Nat Med* 1999, 5, 314.
100. M. D. Roos, W. Xie, K. Su, J. A. Clark, X. Yang, E. Chin, A. J. Paterson, J. E. Kudlow, *Proc Assoc Am Physicians* 1998, 110, 422.
101. Y. Gao, G. J. Parker, G. W. Hart, *Arch Biochem Biophys* 2000, 383, 296.
102. R. Okuyama, M. Yachi, *Biochem Biophys Res Commun* 2001, 287, 366.
103. N. E. Zachara, N, O'Donnell, W. D. Cheung, J. J. Mercer, J. D. Mardi, G. W. Hart, *J Biol Chem* 2004, 279, 30133.
104. J. A. Hanover, Z. Lai, G. Lee, W. A. Lubas, S. M. Sato, *Arch Biochem Biophys* 1999, 362, 38.
105. K. Liu, A. J. Paterson, R. J. Konrad, A. F. Parlow, S. Jimi, M. Roh, E. Chin, Jr., J. E. Kudlow, *Mol Cell Endocrinol* 2002, 194, 135.
106. M. S. Macauley, G. E. Whitworth, A. W. Debowski, D. Chin, D. J. Vocadlo, *J Biol Chem* 2005, 280, 25313.
107. B. L. Mark, D. J. Vocadlo, S. Knapp, B. L. Triggs-Raine, S. G. Withers, M. N. James, *J Biol Chem* 2001, 276, 10330.
108. R. S. Haltiwanger, K. Grove, G. A. Philipsberg, *J Biol Chem* 1998, 273, 3611.
109. D. J. Miller, X. Gong, B. D. Shur, *Development* 1993, 118, 1279.
110. L. Y. Zou, S. L. Yang, S. H. Hu, I. H. Chaudry, R. B. Marchase, J. C. Chatham, *Shock* 2007, 27, 402.
111. J. B. Huang, A. J. Clark, H. R. Petty, *Cellular Immunology* 2007, 245, 1.
112. U. J. G. Conference, in *US/Japan Glyco* 2004 *Conference*, Honolulu, Hi., 2004.
113. L. Y. Zou, S. L. Yang, S. H. Hu, I. H. Chaudry, R. B. Marchase, J. C. Chatham, *Faseb Journal* 2006, 20, A1471.
114. V. Champattanachai, R. B. Marchase, J. C. Chatham, *American Journal of Physiology-Cell Physiology* 2007, 292, C178.
115. J. C. Jochims, A. Seeliger, *Tetrahedron* 1965, 21, 2611.
116. G. T. Brambleft, M. Goedert, R. Jakes, S. E. Merrick, J. Q. Trojanowski, V. M. Lee, *Neuron* 1993, 10, 1089.
117. A. d. C. Alonso, A. Mederlyova, M. Novak, I. Grundke-lqbal, K. Ilbal, *J Biol Chem* 2004, 279, 34873.

All citations are hereby incorporated by reference.

What is claimed is:

1. A compound having the chemical structure:

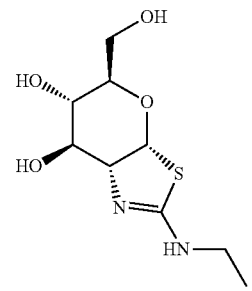

or a pharmaceutically acceptable salt thereof.

2. A compound having the chemical structure:

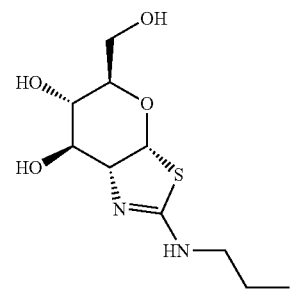

or a pharmaceutically acceptable salt thereof.

3. A pharmaceutical composition comprising the compound of claim 1 or a pharmaceutically acceptable salt thereof, in combination with a pharmaceutically acceptable carrier.

4. A pharmaceutical composition comprising the compound of claim 2, or a pharmaceutically acceptable salt thereof, in combination with a pharmaceutically acceptable carrier.

* * * * *